(12) United States Patent
Hernando et al.

(10) Patent No.: US 9,421,218 B2
(45) Date of Patent: Aug. 23, 2016

(54) COMPOSITIONS AND METHODS FOR TREATMENT OF MELANOMA

(75) Inventors: Eva Hernando, New York, NY (US); Moshe Hoshen, Jerusalem (IL); Iman Osman, Jersey City, NJ (US); Avital Gaziel-Sovran, New York, NY (US); Miguel F. Segura, Barcelona (ES)

(73) Assignee: New York University, New York, NY (US)

( * ) Notice: Subject to any disclaimer, the term of this patent is extended or adjusted under 35 U.S.C. 154(b) by 159 days.

(21) Appl. No.: 13/640,883

(22) PCT Filed: Apr. 13, 2011

(86) PCT No.: PCT/US2011/032347
§ 371 (c)(1),
(2), (4) Date: Oct. 2, 2013

(87) PCT Pub. No.: WO2011/130426
PCT Pub. Date: Oct. 20, 2011

(65) Prior Publication Data
US 2014/0050803 A1    Feb. 20, 2014

Related U.S. Application Data

(60) Provisional application No. 61/323,358, filed on Apr. 13, 2010.

(51) Int. Cl.
*A61K 31/7088* (2006.01)
*C12N 15/113* (2010.01)
*A61K 45/06* (2006.01)

(52) U.S. Cl.
CPC ............ *A61K 31/7088* (2013.01); *A61K 45/06* (2013.01); *C12N 15/1135* (2013.01); *C12N 15/1137* (2013.01); *C12Y 204/01041* (2013.01); *C12N 2310/141* (2013.01); *C12N 2330/51* (2013.01)

(58) Field of Classification Search
USPC ........................................... 514/44; 536/24.5
See application file for complete search history.

(56) References Cited

U.S. PATENT DOCUMENTS

2007/0009530 A1    1/2007  Altaba et al.
2009/0186353 A1    7/2009  Aharonov et al.
2009/0263803 A1    10/2009 Beaudenon et al.

OTHER PUBLICATIONS

An International Preliminary Report on Patentability, mailed Oct. 16, 2012, which issued in corresponding International Application No. PCT/US2011/032347.
Gaziel-Sovran et al., miR-3ob/30d regulation of GaINAc transferases enhances invasion and immunosuppression during metasis Cancer Cell. Jul. 11, 1011, vol. 20, pp. 104-118.
International Search Report mailed Nov. 17, 2011, which issued in corresponding International Application No. PCT/US2011/032347.
Yu, H., Pardoll, D., and Jove, R. (2009). STATs in cancer inflammation and immunity: a leading role for STAT3. Nat Rev Cancer 9, 798-809.

(Continued)

*Primary Examiner* — Terra C Gibbs
(74) *Attorney, Agent, or Firm* — Fish & Richardson P.C.

(57) ABSTRACT

Described herein are compositions and methods for the prognosis, prevention and treatment of melanoma or melanoma associated symptoms. The compositions are microRNA molecules associated with melanoma or with melanoma brain tropism, as well as various nucleic acid molecules relating thereto or derived therefrom.

10 Claims, 51 Drawing Sheets

(56) References Cited

OTHER PUBLICATIONS

Cruz-Munoz, W., Man, S., Xu, P., and Kerbel, R. S. (2008). Development of a preclinical model of spontaneous human melanoma central nervous system metastasis. Cancer Res 68, 4500-4505.
Bettelli, E., Carrier, Y., Gao, W., Korn, T., Strom, T. B., Oukka, M., Weiner, H. L., and Kuchroo, V. K. (2006). Reciprocal developmental pathways for the generation of pathogenic effector THI 7 and regulatory T cells. Nature 441, 235-238.
Bhardwaj, N. (2007). Harnessing the immune system to treat cancer. J Clin Invest 117, 1130-1136.
Bhavanandan, V.P., (1991) Cancer-associated mucins and mucin-type glycoproteins. Glycobiology 1, 493-503.
Bogunovic, D., O'Neill, D. W., Belitskaya-Levy, I., Vacic, V., Yu, Y. L., Adams, S., Darvishian, F., Berman, R., Shapiro, R., Pavlick, A. C., et al. (2009). Immune profile and mitotic index of metastatic melanoma lesions enhance clinical staging in predicting patient survival. Proc Natl Acad Sci US A 106, 20429-20434.
Brockhausen, I. (2006). Mucin-type 0-glycans in human colon and breast cancer: Glycodynamics and functions. EMBO Rep 7, 599-604.
Calin, G. A., and Croce, C. M. (2006). MicroRNA signatures in human cancers. Nat Rev Cancer 6, 857-866.
Croce, C. M., and Calin, G. A. (2005). miRNAs, cancer, and stem cell division. Cell 122, 6-7.
Dennis, J. W., Granovsky, M., and Warren, C. E. (1999). Glycoprotein glycosylation and cancer progression. Biochim Biophys Acta 1473, 21-34.
Ebert, L. M., Tan, B. S., Browning, J., Svobodova, S., Russell, S. E., Kirkpatrick, N., Gedye, C., Moss, D., Ng, S. P., MacGregor, D., et al. (2008). The regulatory T cell associated transcription factor FoxP3 is expressed by tumor cells. Cancer Res 68, 3001-3009.
Ehlers, J. P., Worley, L., Onken, M. D., and Harbour, J. W. (2005). DDEFI is located in an amplified region of chromosome 8q and is overexpressed in uveal melanoma. Clin Cancer Res 11, 3609-3613.
Esquela-Kerscher, A., and Slack, F. J. (2006). Oncomirs—microRNAs with a role in cancer. Nat Rev Cancer 6, 259-269.
Gupta, G. P., and Massague, J. (2006). Cancer metastasis: building a framework. Cell 127, 679-695.
Gupta, P. B., Mani, S., Yang, J., Hartwell, K., and Weinberg, R. A. (2005). The evolving portrait of cancer metastasis. Cold Spring Harb Symp Quant Biol 70, 291-297.
Hinz, S., Pagerols-Raluy, L., Oberg, H. H., Ammerpohl, 0., Grussel, S., Sipos, B., Grutzmann, R., Pilarsky, C., Ungefroren, H., Saeger, H. D., et al. (2007). Foxp3 expression in pancreatic carcinoma cells as a novel mechanism of immune evasion in cancer. Cancer Res 67, 8344-8350.
Hu, Z., Chen, X., Zhao, Y., Tian, T., Jin, G., Shu, Y., Chen, Y., Xu, L., Zen, K., Zhang, C., and Shen, H. (2010). Serum microRNA signatures identified in a genome-wide serum microRNA expression profiling predict survival of non-small-cell lung cancer. J Clin Oncol 28, 1721-1726.
Huang da, W., Sherman, B. T., and Lempicki, R. A. (2009). Systematic and integrative analysis of large gene lists using DAVID bioinformatics resources. Nat Protoc 4, 44-57.
Irizarry, R. A., Bolstad, B. M., Collin, F., Cope, L. M., Hobbs, B., and Speed, T. P. (2003). Summaries of Affymetrix GeneChip probe level data. Nucleic Acids Res 31, el 5.
Kahai, S., Lee, S. C., Lee, D. Y., Yang, J., Li, M., Wang, C. H., Jiang, Z., Zhang, Y., Peng, C., and Yang, B. B. (2009). MicroRNA miR-378 regulates nephronectin expression modulating osteoblast differentiation by targeting GaINT-7. PLoS One 4, e7535.
Kato, K., Takeuchi, H., Kanoh, K., Miyahara, N., Nemoto-Sasaki, Y., Morimoto-Tomita, M., Matsubara, A., Ohashi, Y., Waki, M., Usami, K., et al. (2010). Loss of UDPGaINAc: polypeptide N-acetylgalactosaminyltransferase 3 and reduced 0-glycosylation in colon carcinoma cells selected for hepatic metastasis. Glycoconj J 27, 267-276.
Kudo-Saito, C., Shirako, H., Takeuchi, T., and Kawakami, Y. (2009). Cancer metastasis is accelerated through immunosuppression during Snail-induced EMT of cancer cells. Cancer Cell 15, 195-206.
Lee, J. H., Torisu-Itakara, H., Cochran, A. J., Kadison, A., Huynh, Y., Morton, D. L., and Essner, R. (2005). Quantitative analysis of melanoma-induced cytokine-mediated immunosuppression in melanoma sentinel nodes. Clin Cancer Res 11, 107-112.
Lewis, B. P., Burge, C. B., and Bartel, D. P. (2005). Conserved seed pairing, often flanked by adenosines, indicates that thousands of human genes are microRNA targets. Cell 120, 15-20.
Lu, Y., Ryan, S. L., Elliott, D. J., Bignell, G. R., Futreal, P. A., Ellison, D. W., Bailey, S., and Clifford, S. C. (2009). Amplification and overexpression of Hsa-miR-30b, Hsa-miR-30d and KHDRBS3 at 8q24.22-q24.23 in medulloblastoma. PLoS One 4, e6159.
Ma, L., Teruya-Feldstein, J., and Weinberg, R. A. (2007). Tumour invasion and metastasis initiated by microRNA-IObn breast cancer. Nature 449, 682-688.
Ma, L., Young, J., Prabhala, H., Pan, E., Mestdagh, P., Muth, D., Teruya-Feldstein, J., Reinhardt, F., Onder, T. T., Valastyan, S., et al. miR-9, a MYC/MYCN-activated microRNA, regulates Ecadherin and cancer metastasis. Nat Cell Biol 12, 247-256.
Maione, F., Molla, F., Meda, C., Latini, R., Zentilin, L., Giacca, M., Seano, G., Serini, G., Bussolino, F., and Giraudo, E. (2009). Semaphorin 3A is an endogenous angiogenesis inhibitor that blocks tumor growth and normalizes tumor vasculature in transgenic mouse models. J Clin Invest 119, 3356-3372.
Mandel, U., Hassan, H., Therkildsen, M. H., Rygaard, J., Jakobsen, M. H., Juhl, B. R., Dabelsteen, E., and Clausen, H. (1999). Expression of polypeptide GalNAc-transferases in stratified epithelia and squamous cell carcinomas: immunohistological evaluation using monoclonal antibodies to three members of the GalNAc-transferase family. Glycobiology 9, 43-52.
Martin, F., Ladoire, S., Mignot, G., Apetoh, L., and Ghiringhelli, F. (2010). Human FOXP3 and cancer. Oncogene 29, 4121-4129.
Merlo, A., Casalini, P., Carcangiu, M. L., Malventano, C., Triulzi, T., Menard, S., Tagliabue, E., and Balsari, A. (2009). FOXP3 expression and overall survival in breast cancer. J Clin Oncol 27, 1746-1752.
Palmgren, S., Vartiainen, M., and Lappalainen, P. (2002). Twinfilin, a molecular mailman for actin monomers. J Cell Sci 115, 881-886.
Real, L. M., Jimenez, P., Kirkin, A., Serrano, A., Garcia, A., Canton, J., Zeuthen, J., Garrido, F., and Ruiz-Cabello, F. (2001). Multiple mechanisms of immune evasion can coexist in melanoma tumor cell lines derived from the same patient. Cancer Immunol Immunother 49, 621-628.
Redondo, P., Sanchez-Carpintero, I., Bauza, A., Idoate, M., Solano, T., and Mihm, M. C., Jr. (2003). Immunologic escape and angiogenesis in human malignant melanoma. J Am Acad Dermatol 49, 255-263.
Rozen, S., and Skaletsky, H. (2000). Primer3 on the WWW for general users and for biologist programmers. Methods Mol Biol 132, 365-386.
Scheel, C., Onder, T., Kamoub, A., and Weinberg, R. A. (2007). Adaptation versus selection: the origins of metastatic behavior Cancer Res 67, 11476-11479; discussion 11479-11480.
Segura, M. F., Belitskaya-Levy, I., Rose, A. E., Zakrzewski, J., Gaziel, A., Hanniford, D., Darvishian, F., Berman, R. S., Shapiro, R. L., Pavlick, A. C., et al. (2010). Melanoma MicroRNA Signature Predicts Post-Recurrence Survival. Clin Cancer Res 16, 1577-1586.
Segura, M. F., Hanniford, D., Menendez, S., Reavie, L., Zou, X., Alvarez-Diaz, S., Zakrzewski, J., Blochin, E., Rose, A., Bogunovic, D., et al. (2009). Aberrant miR-182 expression promotes melanoma metastasis by repressing FOX03 and microphthalmia-associated transcription factor. Proc Natl Acad Sci U S A 106, 1814-1819.
Serini, G., Valdembri, D., Zanivan, S., Morterra, G., Burkhardt, C., Caccavari, F., Zammataro, L., Primo, L., Tamagnone, L., Logan, M., et al. (2003). Class 3 semaphorins control vascular morphogenesis by inhibiting integrin function. Nature 424, 391-397.
Sharma, A., Kumar, M., Aich, J., Hariharan, M., Brahmachari, S. K., Agrawal, A., and Ghosh, B. (2009). Posttranscriptional regulation of interleukin-IO expression by hsa-miR-106a. Proc Natl Acad Sci U S A 106, 5761-5766.
Sheedy, F. J., Palsson-McDermott, E., Hennessy, E. J., Martin, C., O'Leary, J. J., Ruan, Q., Johnson, D. S., Chen, Y., and O'Neill, L. A. (2010). Negative regulation of TLR4 via targeting of the proinflammatory tumor suppressor PDCD4 by the microRNA miR-21. Nat Immunol 11, 141-147.

(56) References Cited

OTHER PUBLICATIONS

Subramanian, S., Lui, W. 0., Lee, C. H., Espinosa, I., Nielsen, T. 0., Heinrich, M. C., Corless, C. L., Fire, A. Z., and van de Rijn, M. (2008). MicroRNA expression signature of human sarcomas. Oncogene 27, 2015-2026.

Talmadge, J. E. (2007). Clonal selection of metastasis within the life history of a tumor. Cancer Res 67, 11471-11475.

Tavazoie, S. F., Alarcon, C., Oskarsson, T., Padua, D., Wang, Q., Bos, P. D., Gerald, W. L., and Massague, J. (2008). Endogenous human microRNAs that suppress breast cancer metastasis. Nature 451, 147-152.

Ten Hagen, K. G., Fritz, T. A., and Tabak, L. A. (2003). All in the family: the UDPGalNAc: polypeptide N-acetylgalactosaminyltransferases. Glycobiology 13, 1R-16R.

Tong, A. W., and Nemunaitis, J. (2008). Modulation of miRNA activity in human cancer: a new paradigm for cancer gene therapy? Cancer Gene Ther 15, 341-355.

Valastyan, S., and Weinberg, R. A. (2009). Assaying microRNA loss-of-function phenotypes in mammalian cells: emerging tools and their potential therapeutic utility. RNA Biol 6, 541-545.

Van Den Berg, C., Guan, X. Y., Von Hoff, D., Jenkins, R., Bittner, Griffin, C., Kallioniemi, 0., Visakorpi, McGill, Herath, J., and et al. (1995). DNA sequence amplification in human prostate cancer identified by chromosome microdissection: potential prognostic implications. Clin Cancer Res 1, 11-18.

Visapaa, H., Seligson, D., Eeva, M., Gaber, F., Rao, J., Belldegrun, A., and Palotie, A. (2003). 8q24 amplification in transitional cell carcinoma of bladder. Appl Immunohistochem Mol Morphol 11, 33-36.

Wu, Q., and Maniatis, T. (1999). A striking organization of a large family of human neural cadherin-like cell adhesion genes. Cell 97, 779-790.

Yao, J., Liang, L., Huang, S., Ding, J., Tan, N., Zhao, Y., Yan, M., Ge, C., Zhang, Z., Chen, T., et al. (2009). MicroRNA-30d promotes tumor invasion and metastasis by targeting Galphai2 in hepatocellular carcinoma. Hepatology 51, 846-856.

Yu, F., Deng, H., Yao, H., Liu, Q., Su, F., and Song, E. (2010). Mir-30 reduction maintains selfrenewal and inhibits apoptosis in breast tumor-initiating cells. Oncogene 29, 4194-4204.

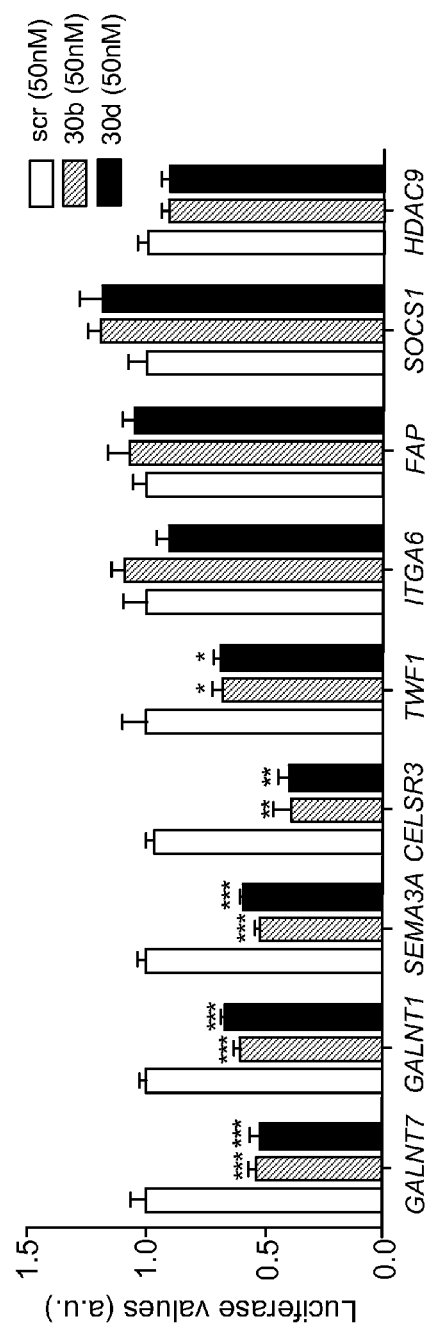
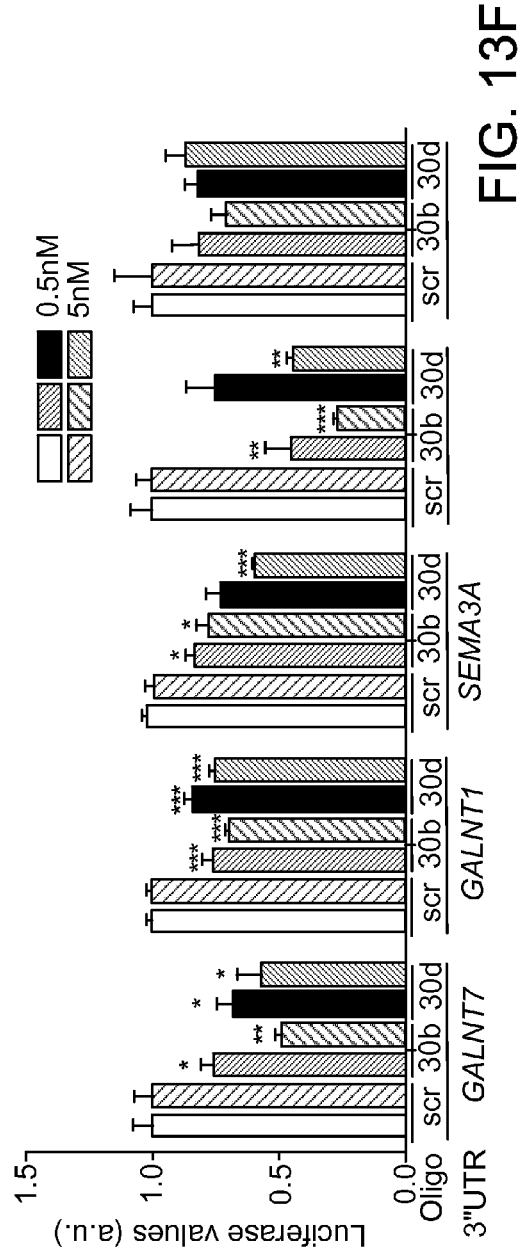
FIG. 13E
FIG. 13F

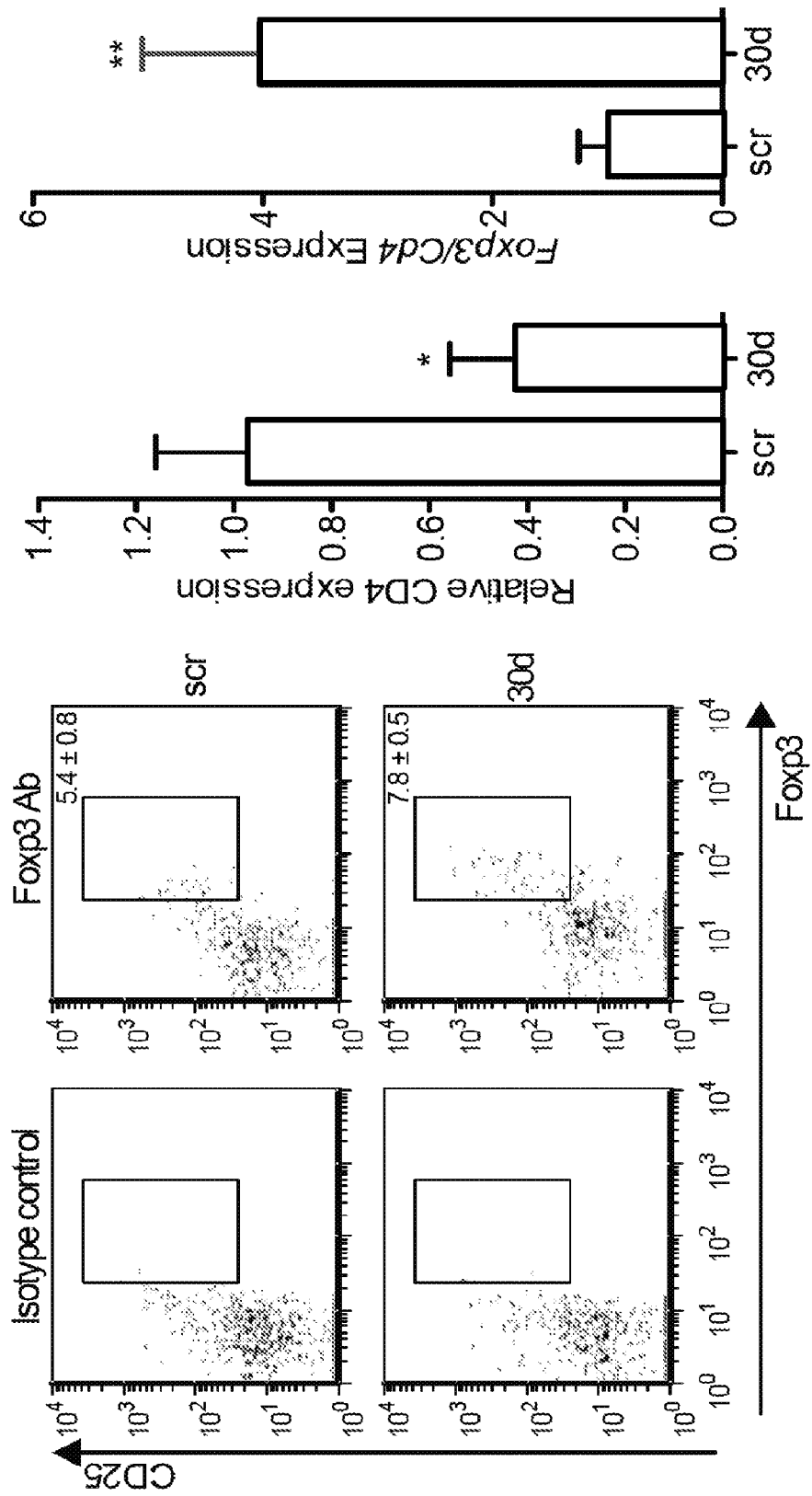

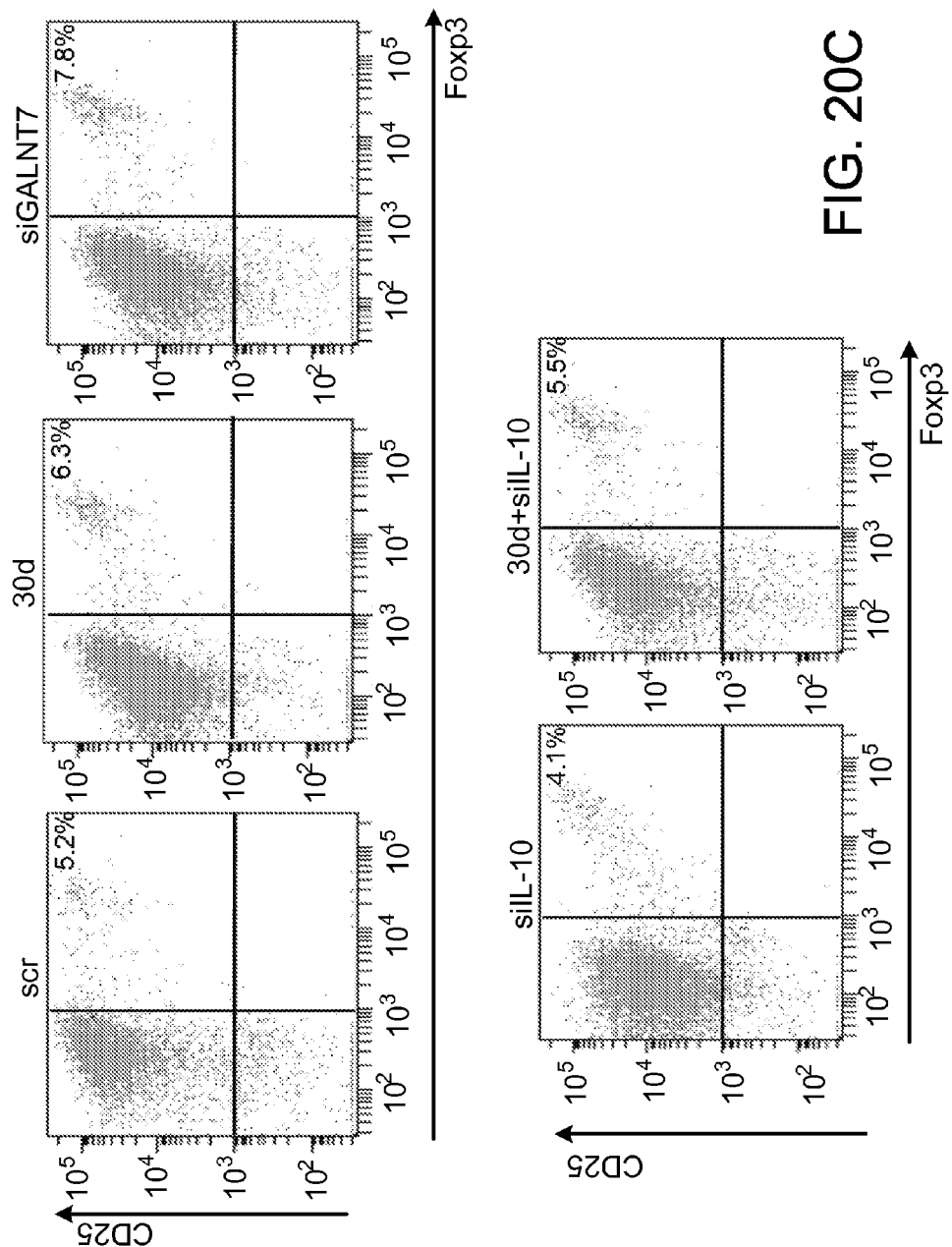

SEQUENCE LISTING

<160> NUMBER OF SEQ ID NOS: 38

<210> SEQ ID NO 1
<211> LENGTH: 21
<212> TYPE: RNA
<213> ORGANISM: Homo sapiens

<400> SEQUENCE: 1
acagcaggca cagacaggca g                                             21

<210> SEQ ID NO 2
<211> LENGTH: 23
<212> TYPE: RNA
<213> ORGANISM: Homo sapiens

<400> SEQUENCE: 2
cccaguguuc agacuaccug uuc                                           23

<210> SEQ ID NO 3
<211> LENGTH: 22
<212> TYPE: RNA
<213> ORGANISM: Homo sapiens

<400> SEQUENCE: 3
ucucccaacc cuuguaccag ug                                            22

<210> SEQ ID NO 4
<211> LENGTH: 22
<212> TYPE: RNA
<213> ORGANISM: Homo sapiens

<400> SEQUENCE: 4
acaguagucu gcacauuggu ua                                            22

<210> SEQ ID NO 5
<211> LENGTH: 23
<212> TYPE: RNA
<213> ORGANISM: Homo sapiens

<400> SEQUENCE: 5
cgggucggag uuagcucaag cgg                                           23

<210> SEQ ID NO 6
<211> LENGTH: 22
<212> TYPE: RNA
<213> ORGANISM: Homo sapiens

<400> SEQUENCE: 6
ugagaugaag cacguagcu ca                                             22

<210> SEQ ID NO 7
<211> LENGTH: 21
<212> TYPE: RNA
<213> ORGANISM: Homo sapiens

<400> SEQUENCE: 7
cagcagcaca cuguggutug u                                             21

<210> SEQ ID NO 8
<211> LENGTH: 24
<212> TYPE: RNA
<213> ORGANISM: Homo sapiens

<400> SEQUENCE: 8

```
guccaguuuu cccaggaauc ccuu                                          24

<210> SEQ ID NO 9
<211> LENGTH: 22
<212> TYPE: RNA
<213> ORGANISM: Homo sapiens

<400> SEQUENCE: 9
uguaaacauc cccgacugga ag                                            22

<210> SEQ ID NO 10
<211> LENGTH: 23
<212> TYPE: RNA
<213> ORGANISM: Homo sapiens

<400> SEQUENCE: 10
aaaccguuac cauuacugag uuu                                           23

<210> SEQ ID NO 11
<211> LENGTH: 22
<212> TYPE: RNA
<213> ORGANISM: Homo sapiens

<400> SEQUENCE: 11
uguaaacauc cuacacucag cu                                            22

<210> SEQ ID NO 12
<211> LENGTH: 21
<212> TYPE: RNA
<213> ORGANISM: Homo sapiens

<400> SEQUENCE: 12
ucgaggagcu cacagucuag u                                             21

<210> SEQ ID NO 13
<211> LENGTH: 23
<212> TYPE: RNA
<213> ORGANISM: Homo sapiens

<400> SEQUENCE: 13
aaugacacga ucacucccgu uga                                           23

<210> SEQ ID NO 14
<211> LENGTH: 23
<212> TYPE: RNA
<213> ORGANISM: Homo sapiens

<400> SEQUENCE: 14
uguaaacauc cuacacucuc agc                                           23

<210> SEQ ID NO 15
<211> LENGTH: 23
<212> TYPE: RNA
<213> ORGANISM: Homo sapiens

<400> SEQUENCE: 15
caaagugcuu acagugcagg uag                                           23

<210> SEQ ID NO 16
<211> LENGTH: 110
<212> TYPE: RNA
<213> ORGANISM: Homo sapiens
<220> FEATURE:
```

```
<221> NAME/KEY: misc_feature
<222> LOCATION: 36
<223> OTHER INFORMATION: n = A,T,C or G

<400> SEQUENCE: 16
ggccuggcug  gacagaguug  ucauguguau  gccugncuac  acuugcugug  cagaacaucc     60
gcucaccugu  acagcaggca  cagacaggca  gucacaugac  aacccagccu                110

<210> SEQ ID NO 17
<211> LENGTH: 71
<212> TYPE: RNA
<213> ORGANISM: Homo sapiens

<400> SEQUENCE: 17
gccaacccag  uguucagacu  accguucag   gaggcucuca  auguguacag  uagucugcac     60
auugguuagg  c                                                              71

<210> SEQ ID NO 18
<211> LENGTH: 110
<212> TYPE: RNA
<213> ORGANISM: Homo sapiens

<400> SEQUENCE: 18
aggaagcuuc  uggagauccu  gcuccgucgc  cccaguguuc  agacuaccug  uucaggacaa     60
ugccguugua  caguagucug  cacauugguu  agacugggca  agggagagca                110

<210> SEQ ID NO 19
<211> LENGTH: 84
<212> TYPE: RNA
<213> ORGANISM: Homo sapiens

<400> SEQUENCE: 19
cuccccaugg  cccugucucc  caacccuugu  accagcucug  ggcucagacc  cugguacagg     60 ccuggggac  agggaccugg  ggac                                                84

<210> SEQ ID NO 20
<211> LENGTH: 121
<212> TYPE: RNA
<213> ORGANISM: Homo sapiens

<400> SEQUENCE: 20
cacuccuacc  cggucggag   uuagcucaag  cgguuaccuc  cucaugccgg  acuuucuauc     60
uguccaucuc  ugucugggg   uucgagaccc  gcgggugcuu  acugacccuu  uuaugcaaua    120
a                                                                         121

<210> SEQ ID NO 21
<211> LENGTH: 106
<212> TYPE: RNA
<213> ORGANISM: Homo sapiens

<400> SEQUENCE: 21
gcgcagcgcc  cugucuccca  gccugaggug  cagugcugca  ucucugguca  guugggaguc     60
ugagaugaag  cacuguagcu  caggaagaga  gaaguuguuc  ugcagc                    106

<210> SEQ ID NO 22
<211> LENGTH: 112
<212> TYPE: RNA
<213> ORGANISM: Homo sapiens

<400> SEQUENCE: 22
```

```
ccaccccggu ccugcucccg ccccagcagc acacuguggu uuguacggca cuguggccac    60
guccaaacca cacuguggug uuagagcgag gguggggggag gcaccgccga gg           112

<210> SEQ ID NO 23
<211> LENGTH: 88
<212> TYPE: RNA
<213> ORGANISM: Homo sapiens

<400> SEQUENCE: 23
caccuugucc ucacggucca guuucccag gaaucccuua gaugcuaaga uggggauucc     60
uggaaauacu guucuugagg ucaugguu                                      88

<210> SEQ ID NO 24
<211> LENGTH: 70
<212> TYPE: RNA
<213> ORGANISM: Homo sapiens

<400> SEQUENCE: 24
guuguuguaa acauccccga cuggaagcug uaagacacag cuaagcuuuc agucagaugu   60
uugcugcuac                                                          70

<210> SEQ ID NO 25
<211> LENGTH: 73
<212> TYPE: RNA
<213> ORGANISM: Homo sapiens

<400> SEQUENCE: 25
cuugggaaug gcaaggaaac cguuaccauu acugaguuua guaaugguaa gguucucru    60 ugcuauaccc aga                                                      73

<210> SEQ ID NO 26
<211> LENGTH: 89
<212> TYPE: RNA
<213> ORGANISM: Homo sapiens

<400> SEQUENCE: 26
accaaguuuc aguucaugua aacauccuac acucagcugu aauacaugga uuggcuggga   60
gguggauguu uacuucacgc ugacuugga                                     89

<210> SEQ ID NO 27
<211> LENGTH: 90
<212> TYPE: RNA
<213> ORGANISM: Homo sapiens

<400> SEQUENCE: 27
uuuccugccc ucgaggagcu cacagucuag uaugucucau ccccuacuag acugaagcuc   60
cuugaggaca gggauggucu uacucaccuc                                    90

<210> SEQ ID NO 28
<211> LENGTH: 87
<212> TYPE: RNA
<213> ORGANISM: Homo sapiens

<400> SEQUENCE: 28
gaaagcgcuu uggaaugaca cgaucacucc cguugagugg gcacccgaga agccaucggg   60
aaugucgugu ccgcccagug cucuuuc                                       87

<210> SEQ ID NO 29
```

```
<211> LENGTH: 89
<212> TYPE: RNA
<213> ORGANISM: Homo sapiens

<400> SEQUENCE: 29
accaugcugu agugugugua aacauccuac acucucagcu gugagcucaa gguggcuggg    60
agaggguugu uuacuccuuc ugccaugga                                     89

<210> SEQ ID NO 30
<211> LENGTH: 72
<212> TYPE: RNA
<213> ORGANISM: Homo sapiens

<400> SEQUENCE: 30
agauacugua aacauccuac acucucagcu guggaaagua agaaagcugg gagaaggcug    60
uuuacucuuu cu                                                       72

<210> SEQ ID NO 31
<211> LENGTH: 84
<212> TYPE: RNA
<213> ORGANISM: Homo sapiens

<400> SEQUENCE: 31
gucagaauaa ugucaaagug cuuacagugc agguagugau augugcaucu acugcaguga    60
aggcacuugu agcauuaugg ugac                                          84

<210> SEQ ID NO 32
<211> LENGTH: 43
<212> TYPE: RNA
<213> ORGANISM: Homo sapiens

<400> SEQUENCE: 32
ucaucugcag uuacuguuua cauaaacuuu guagauguuu aca                     43

<210> SEQ ID NO 33
<211> LENGTH: 43
<212> TYPE: RNA
<213> ORGANISM: Homo sapiens

<400> SEQUENCE: 33
ucaucugcag uuacugauau cauaaacuuu guagauguuu aca                     43

<210> SEQ ID NO 34
<211> LENGTH: 43
<212> TYPE: RNA
<213> ORGANISM: Homo sapiens

<400> SEQUENCE: 34
ucaucugcag uuacuguuua cauaaacuuu guagaugggc cca                     43

<210> SEQ ID NO 35
<211> LENGTH: 22
<212> TYPE: RNA
<213> ORGANISM: Homo sapiens

<400> SEQUENCE: 35
acugugcaca cugauguuua ca                                            22

<210> SEQ ID NO 36
<211> LENGTH: 22
<212> TYPE: RNA
<213> ORGANISM: Homo sapiens
```

```
<400> SEQUENCE: 36
acugugcaca cugaugauau ca                                          22

<210> SEQ ID NO 37
<211> LENGTH: 21
<212> TYPE: RNA
<213> ORGANISM: Homo sapiens

<400> SEQUENCE: 37
ggcauuaugu ggauguuuac a                                           21

<210> SEQ ID NO 38
<211> LENGTH: 22
<212> TYPE: RNA
<213> ORGANISM: Homo sapiens

<400> SEQUENCE: 38
ggcauuaugg uggaugauau ca                                          22
```

COMPOSITIONS AND METHODS FOR TREATMENT OF MELANOMA

CROSS REFERENCE TO PRIOR APPLICATIONS

This is a U.S. National Phase application under 35 U.S.C. §371 of International Patent Application No. PCT/US2011/032347, filed Apr. 13, 2011, and claims the benefit of U.S. Provisional Patent Application No. 61/323,358, filed Apr. 13, 2010 both of which are incorporated by reference herein in their entirety. The International Application published in English on Oct. 20, 2011 as WO 2011/130426 under PCT Article 21(2).

FIELD OF THE INVENTION

The invention relates to compositions and methods for the prognosis, prevention and treatment of melanoma or melanoma associated symptoms. Specifically the invention relates to microRNA molecules associated with melanoma or with melanoma brain tropism, as well as various nucleic acid molecules relating thereto or derived therefrom.

BACKGROUND OF THE INVENTION

In recent years, microRNAs (miRNAs, miRs) have emerged as an important novel class of regulatory RNA, which have a profound impact on a wide array of biological processes.

These small (typically 18-24 nucleotides in length) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. The expression of many miRs was found to be altered in numerous types of human cancer, and in some cases strong evidence has been put forward in support of the conjecture that such alterations may play a causative role in tumor progression. There are currently about 900 known human miRs.

Malignant melanoma (MM) is one of the fastest growing malignancies in the United States (Benjamin et al., 2007, Mol Carcinog 46, 671-678), and its associated mortality that continues to rise throughout the world. In addition to well defined genetic lesions, melanomas are characterized by frequent chromosomal aberrations associated with tumor progression (Jonsson et al., 2007, Cell 120, 635-647). In particular, melanomas display a characteristic pattern of genomic alterations involving miRNA genes.

Melanoma patients with brain metastases have short survival and are excluded from most clinical trials. With a median survival of less than 6 months, the development of brain metastases (B-Met) portends a dismal prognosis for melanoma patients (Raizer et al. 2008, Neuro-oncology 10(2):199-207). Clinical trials open to melanoma patients with B-Met are limited, as their poor prognosis precludes entry into most trials of novel agents. In terms of absolute risk, melanoma has a high predilection to metastasize to the brain (Maher et al., 2009, Cancer research 69(15):6015-6020). Compared to other solid malignancies, a higher proportion of melanoma brain metastases represent the only site of metastatic involvement, suggesting a specific CNS-tropism (Thompson J F, Morton D, & Kroon B (2004) Textbook of Melanoma (Martin Dunitz, London) p. 465). This high rate of CNS involvement may be due to a "homing" effect given that melanocytes and neuronal subpopulations such as glial cells share a common neural crest progenitor (Herlyn et al., 2000, Melanoma Res 10(4):303-312). The molecular mechanism responsible for this predilection is unknown, thus one is unable to accurately predict which primary melanoma patients will ultimately develop B-Met. There remains a need for the identification of prognostic variables present early in the melanoma course that can identify patients at highest risk for B-Met who may benefit from increased surveillance and/or prophylactic interventions that target the CNS.

SUMMARY OF THE INVENTION

The present invention is based in part on the finding that specific miRNAs are important mediators of melanoma dissemination to the brain. A miRNA microarray analysis of metastatic melanoma tissues was conducted and revealed a subset of miRNAs differentially expressed in brain metastases relative to other sites. A brain-specific signature comprised of seven miRNAs was further validated in an independent cohort of metastatic melanoma samples. Then, the trend of expression of those miRNAs was analyzed during tumor progression by comparing their levels in primary tumors and their paired metastasis from patients with or without recurrence in the brain. Differential expression of some miRNAs was already evident at diagnosis in primary tumors that recurred in the brain, while for others it was acquired in the transition from primary to metastasis, suggesting that it may be a later event in tumor progression. Furthermore, in vitro modulation of specific signature miRNAs significantly altered the ability of melanoma cells to execute processes such as adhesion and transmigration through human brain endothelial cells and proliferation in brain conditioned media. Additionally, using an in vivo model of melanoma brain metastasis it was confirmed the capacity of specific miRNA alterations to promote melanoma cells' competence to reach the brain. The analysis of potential downstream mediators of select miRNAs revealed the involvement of the immune response, as well as inflammatory and chemotactic mediators in this process. These results expand the understanding of the mechanisms that control melanoma brain metastasis, potentially revealing novel therapeutic avenues for patients for whom no viable approaches are currently available.

The present invention provides specific nucleic acid sequences and variants thereof for use in the treatment, prognosis of melanoma and predicting melanoma brain metastasis.

According to a first aspect, the present invention provides a method of treating or preventing melanoma in a subject in need thereof comprising administering to the subject an effective amount of a composition comprising an isolated nucleic acid comprising a nucleic acid sequence selected from the group consisting of: SEQ ID NOS: 1-8 and 16-23 and a pharmaceutically acceptable carrier.

According to some embodiments the nucleic acid is a modified oligonucleotide. According to some embodiments the melanoma is metastatic melanoma. According to some embodiments the metastatic melanoma is melanoma brain metastases. According to some embodiments the subject is a human.

According to some embodiments, the administration comprises intratumoral administration, chemoemobilization, subcutaneous administration or intravenous administration. According to some embodiments the intratumoral administration is delivered through the blood brain barrier by a method selected from disruption of the blood brain barrier by osmotic means, use of vasoactive substances selected from the group comprising bradykinin, exposure to high intensity focused ultrasound, use of endogenous transport systems selected from the group comprising carrier-mediated glucose transporters and carrier-mediated amino acid carriers, use of receptor-mediated transcytosis selected from the group comprising receptor-mediated transcytosis of insulin and receptor-mediated transcytosis of transferrin, blocking of active efflux transporters selected from the group comprising p-glycoprotein, intracerebral implantation, convection-enhanced distribution, and use of an infusion pump.

According to some embodiments, the administered composition further comprises a pharmaceutically acceptable carrier. According to some embodiments the method further comprises administration of at least one additional therapy. According to some embodiments the at least one additional therapy is a chemotherapeutic agent. The chemotherapeutic agent may be selected from dacarbazine (DTIC), hydroxylurea, temozolomide, cisplatin, carboplatin, camptothecins, doxorubicin, cyclophosphamide, etoposide, vinblastine, Actinomycin D and cloposide. The additional therapy may be administered at the same time, less frequently, or more frequently than the composition of the invention.

In certain embodiments, the modified oligonucleotide is administered at a dose selected from 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, and 800 mg. The modified oligonucleotide may be administered one per day, once per week, once per two weeks, once per three weeks, or once per four weeks.

In certain embodiments, the administration of the composition of the invention results in inhibition of melanoma metastases, reduction of melanoma metastases size and/or melanoma metastases number. In certain embodiments, the administration of the composition of the invention prevents, slows, and/or stops metastatic progression. In certain embodiments, the administration of the composition of the invention results in cellular apoptosis of melanoma cells. In certain embodiments, the administration of the composition of the invention extends the overall survival time of the subject. In certain embodiments, the administration of the composition of the invention extends the progression-free survival of the subject. In certain embodiments, administration of the composition of the invention prevents the recurrence of melanoma. In certain embodiments, administration of the composition of the invention prevents recurrence of melanoma metastases.

The use of a nucleic acid comprising a nucleic acid sequence selected from the group consisting of:
  (a) SEQ ID NOS: 1-8 and 16-23, and
  (b) a sequence that is complementary to SEQ ID NOS: 9-15, and 24-31 for the manufacture of a medicament for the treatment or prevention of melanoma, is also provided.

According to other aspects, a method is provided for inhibiting the growth or viability of melanoma cells comprising increasing, in said cells, the expression level of a nucleic acid sequence selected from the group consisting of SEQ ID NOs: 1-8 and 16-24 to the expression levels of normal, i.e. non-transformed cells.

According to some aspects, a method is provided for inhibiting the growth or viability of melanoma cells comprising inhibiting, in said cells, the expression level of a nucleic acid sequence selected from the group consisting of SEQ ID NOS: 9, 11 and 9+11 and a pharmaceutically acceptable carrier. "Inhibiting" is defined herein as more than 50% inhibition of expression.

According to another aspect, a method is provided for determining the prognosis of melanoma in a subject comprising obtaining a biological sample from said subject, providing an expression profile of a nucleic acid sequence selected from the group consisting of SEQ ID NOS: 1-31 and from said sample; and comparing said obtained expression profile to a threshold expression level, wherein a differential expression of said nucleic acids as compared to said threshold expression level is predictive of the prognosis of said subject.

According to some embodiments, said prognosis is the risk of developing metastases. According to other embodiments, said prognosis is the risk of developing brain metastases.

According to one embodiment, a relative high expression profile of SEQ ID NOS: 9, 11 and 9+11 sequences in said biological sample is indicative of poor prognosis. "Relatively high" is defined herein as above the median value.

According to another embodiment, a relative high expression profile of SEQ ID NOS: 1-8, 16-23 and in said biological sample is indicative of good prognosis. "Relatively high" is defined herein as above the median value In some aspects the method is used to determine a course of treatment for the subject.

In some embodiments of the invention the biological sample is selected from the group consisting of bodily fluid, a cell line and a tissue sample. In some embodiments the tissue is a fresh, frozen, fixed, wax-embedded or formalin fixed paraffin-embedded (FFPE) tissue.

In additional embodiments the expression levels of the invention are determined by a method selected from the group consisting of nucleic acid hybridization, nucleic acid amplification, and a combination thereof. In some embodiments the nucleic acid hybridization is performed using a solid-phase nucleic acid biochip array or in situ hybridization. In some embodiments, the nucleic acid amplification is a real-time PCR method. In some embodiments, the real-time PCR method comprises forward and reverse primers, and may further comprise hybridization with a probe comprising a nucleic acid sequence that is complementary to a sequence selected from SEQ ID NOS:1-31.

According to other aspects, also provided is a kit for determining the prognosis of melanoma in a subject, comprising a probe comprising a nucleic acid sequence that is complementary to a sequence selected from SEQ ID NOS: 1-31 and instructions for use thereof.

A method of modulating the expression level of a cytokine is also provided. The method may comprise introducing to a subject in need thereof an effective amount of a composition comprising a nucleic acid sequence selected from the group consisting of (a) SEQ ID NOS: 9, 24; and (b) fully complementary sequence of (a).

According to some embodiments, said cytokine is IL-10.

These and other embodiments of the present invention will become apparent to those of ordinary skill in the art in conjunction with the figures, description and claims that follow.

BRIEF DESCRIPTION OF THE DRAWINGS

FIG. 1A Expression is also significantly lower in the primary melanoma from B-Met compared to the primary from other sites of metastasis (checkered boxes). The Y-axis shows the relative expression in log scale. *p<0.05, I—benign nevi, II—primary of brain mets, III—brain mets, IV—primary of other mets, V—other mets.

FIG. 1B demonstrates that miR-199a-5p (SEQ ID NO: 2) has lower expression in B-Met compared to other sites of metastasis (solid boxes). Expression is also significantly lower in the primary melanoma from B-Met compared to the primary from other sites of metastasis (checkered boxes). The Y-axis shows the relative expression in log scale. *p<0.05, I—benign nevi, II—primary of brain mets, III—brain mets, IV—primary of other mets, V—other mets.

FIG. 1C demonstrates that miR-214 (SEQ ID NO: 1) has lower expression in B-Met compared to other sites of metastasis (solid boxes). Expression is also significantly lower in the primary melanoma from B-Met compared to the primary from other sites of metastasis (checkered boxes). The Y-axis shows the relative expression in log scale. *p<0.05, I—benign nevi, II—primary of brain mets, III—brain mets, IV—primary of other mets, V—other mets.

FIG. 1D demonstrates that miR-30b (SEQ ID NO: 11) has higher expression in metastasis compared to primary tumors. The Y-axis shows the relative expression in log scale.*p<0.05, I—benign nevi, II—primary of brain mets, III—brain mets, IV—primary of other mets, V—other mets.

FIG. 1E demonstrates that miR-30d (SEQ ID NO: 9) has higher expression in metastasis compared to primary tumors. The Y-axis shows the relative expression in log scale.*p<0.05, I—benign nevi, II—primary of brain mets, III—brain mets, IV—primary of other mets, V—other mets.

FIG. 3A shows the Melanoma cell lines (4L, 5B1 and 5B2 stably transduced with GFP-expressing lentivirus), transduced with scrambled (I) or miR-199a-3p (II), were plated on tissue culture inserts overlaid with a confluent layer of HCMEC/D3 brain endothelial cells. After 15 h, the trans-migrated cells on the bottom of the insert were counted using a fluorescent microscope. The Y-axis shows the average number of trans-migrated cells/field.

FIG. 3B demonstrates the results of adhesion experiment in miR-199a-3p-transduced melanoma cells. Melanoma cell lines (4L, 5B1 and 5B2, stably transduced with GFP-expressing lentivirus) were adhered to a monolayer of human brain endothelial cells, after transient transfection with scramble oligonucleotides (I) or miR-199a-3p mimic oligonucleotides (II). The Y-axis shows the average number of adhered cells/field.

FIG. 4A shows the relative expression of miR-199a-3p (Y-axis) in xenografts of 131/4-5B1 melanoma cells stably transduced with lentiviral vector miRZIP-199a-3p (containing the antisense sequence of miR-199a-3p-II) or with lentiviral vector control (I), as measured by quantitative RT-PCR FIG. 4B shows brain metastasis-free survival (Y-axis) of NOD/SCID mice injected with 131/4-5B1 melanoma cells stably transduced with scramble (solid line) or miRZIP-199a-3p lentivirus (dashed line), after surgical removal of the post primary xenograft in the flank (weeks, X-axis). P=0.045.

FIG. 4C shows fluorescent images of brain metastases in whole brains of mice transduced with miR-Zip-199a-3p lentivirus.

FIG. 5B demonstrates that miR-30d (SEQ ID NO: 9) is upregulated from primary (I) to metastatic melanoma (II) as detected by qRT-PCR of human samples (n=17) obtained from paired primary-met cases. The Y-axis shows relative expression of miR-30d in log scale.

FIGS. 13A-13H. MiR-30b/30d directly targets SEMA3A, TWF1, CESLR3, GALNT7 and GALNT1. 13A-13C Microarray analysis performed in independent biological duplicate for each indicated cell line. 13A. Heatmap showing the average normalized relative expression levels of genes involved in cell-cell/ECM contacts, motility, metastasis, immune response, or angiogenesis in the indicated cell lines transfected with either scr or miR-30d mimics (50 nM for both). 13B. Venn diagram depicting the overlap between predicted miR-30d targets (TargetScan) and genes significantly downregulated in response to miR-30d overexpression in two cell lines. 13C. Venn diagram illustrating the overlap between predicted targets of an unrelated miRNA (miR-199a-3p) and genes significantly downregulated in response to miR-30d overexpression in two cell lines. 13D. Heatmap depicting the expression levels of selected predicted targets in 18 human metastatic melanoma tissues with increasing levels of miR-30d. Note the inverse correlation between target expression and miR-30d levels. Each column represents an average expression of 4-8 samples with similar miR-30d levels. 13E. Reporter assay in 293T cells transfected with miR-30b or miR-30d (50 nM) and constructs carrying the luciferase cDNA fused to the 3'UTR of selected predicted targets. GALNT7, GALNT1, SEMA3A, CELSR3 and TWF1 3'UTR were found to be potential direct targets of mir-30d and miR30b. 13F. Reporter assay in 293T cells transfected with luciferase constructs fused to the 3'UTR of GALNT7, GALNT1, SEMA3A, CESLR3 and TWF1 and significantly lower concentrations (0.5 nM, 5 nM) of miR-30b/30d. GALNT7, GALNT1, SEMA3A, CELSR3 were found to be direct targets of miR-30b/30b. 13G-13H. Reporter assay in 293T cells transfected with luciferase constructs carrying GALNT7, GALNT1 and SEMA3A 3'UTRs mutated in miR-30b/30d binding sites. Luciferase activity was re-constituted when miR-30b/30b binding sites were mutated (13G). DM=double mutant (*p<0.05; p<0.01; *p<0.001).

FIGS. 17A-17E. MiR-30d associates with enhanced immunosuppressive features at the metastatic site. 17A. Representative flow cytometry of regulatory T cells (CD4$^+$ CD25$^+$ Foxp3$^+$) isolated from whole lungs of mice injected with B16F10/scr or B16F10/miR-30d (mean±SEM, n=4 mice per group). Isotype controls are shown on the left for each treatment group. Note the increased percentage of regulatory T cells in the B16F10/miR-30d-transduced lungs. 17B. Lower CD4 mRNA levels in macrometastases dissected from B16F10/miR-30d relative to B16F10/scr injected mice (n=3 lungs per group). 17C. Increased Foxp3 mRNA expression in macro-dissected metastases extracted from lungs of mice injected with B16F10/miR-30d relative to B16F10/scr injected mice (n=3 per group). 17D. CD3 immunofluorescence staining of metastases of B16F10/mir-30d and B16F10/scr-injected mice shows reduced recruitment of T cells to scr-transfected compared to B16F10/miR-30d transfected metastasis. Corresponding H&E staining on consecutive sections are shown in upper panels and metastatic foci are circled. Scatter plot depicts the number of recruited CD3+ T cells to the metastasis in several mice per group. The number of cells was normalized to the area of metastasis. 17E. FoxP3 immunofluorescence staining shows increased recruitment of regulatory T lymphocytes to B16F10/miR-30d compared to B16F10/scr metastases. Corresponding H&E staining on consecutive sections are shown in upper panels and metastatic foci are circled. Scatter plot depicts the number of recruited CD3+ T cells to the metastasis in several different mice for each group. Scale bars represent 100 µm (*p<0.05; **p<0.01).

FIGS. 20A-20C. MiR-30d levels associate with FOXP3 induction. A. Immunohistochemistry staining for FOXP3 in human melanoma cells (n=45). The fraction of patient samples with higher miR-30d expression includes a larger portion of FOXP3 expressing. B. FoxP3 and HMBA45 immunohistochemistry stainings in consecutive sections of melanoma specimens. C. Flow cytometry plots of CD25+ FoxP3+ cells derived from CD4+ splenocytes isolated from FoxP3-GFP mice after activation with CD28 and CD3 antibodies and incubated in the presence of supernatants from scramble (scr), miR-30d, siGALNT7, siIL10, miR-30d+ siIL10-transduced A375 melanoma cells. (*p<0.05)

DETAILED DESCRIPTION OF THE INVENTION

Figure 1A:
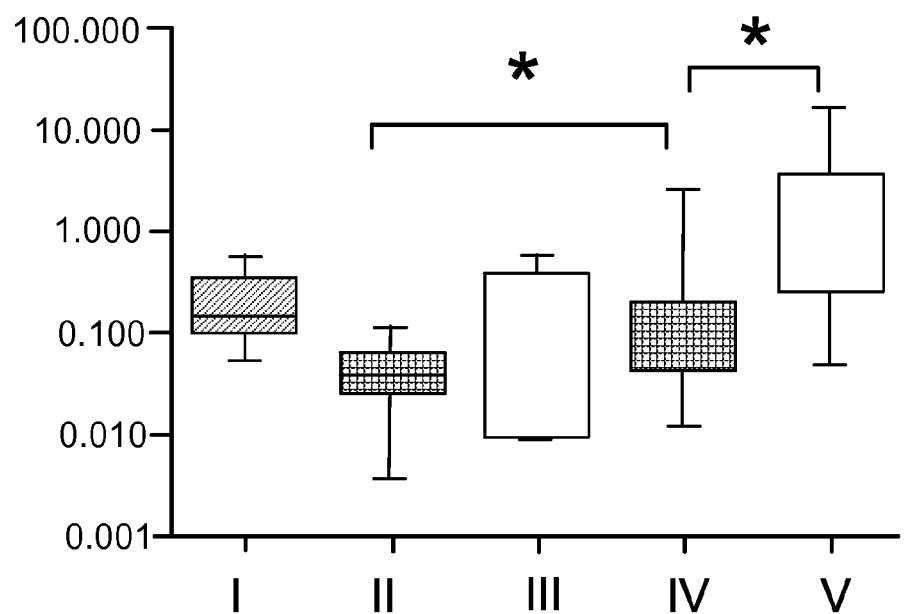
FIGS. 1A-1E demonstrate that miR-199a-3p (SEQ ID NO: 4) has lower expression in B-Met compared to other sites of metastasis (solid boxes).
Figure 1B:
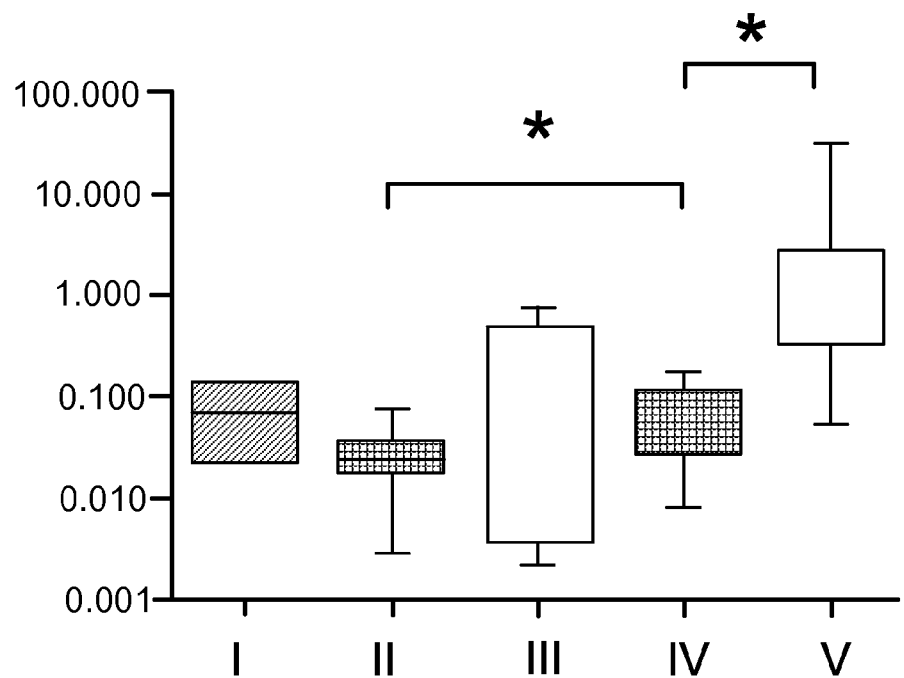
Figure 1C:
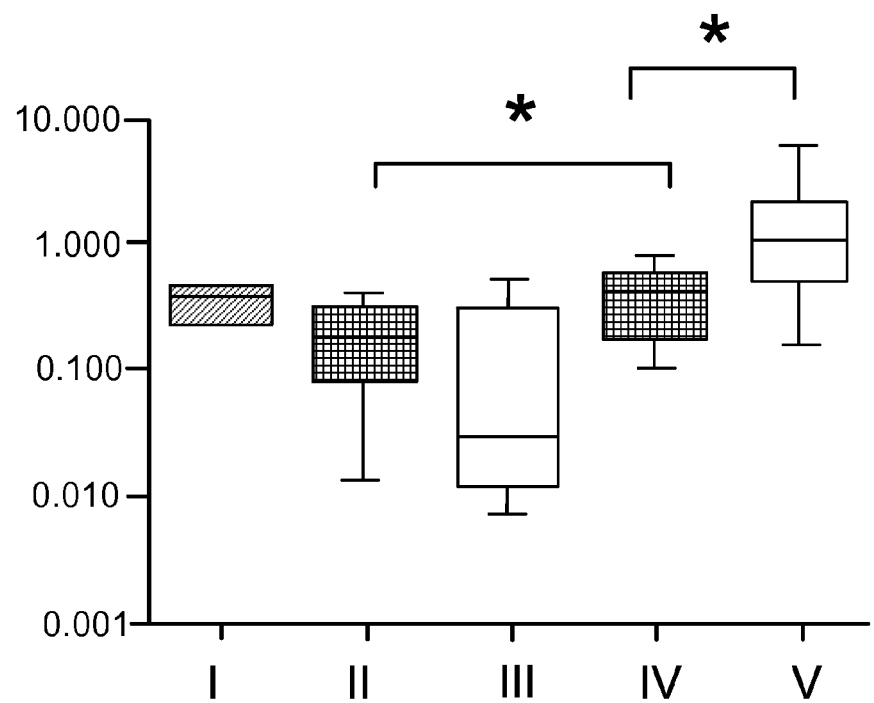
Figure 1D:
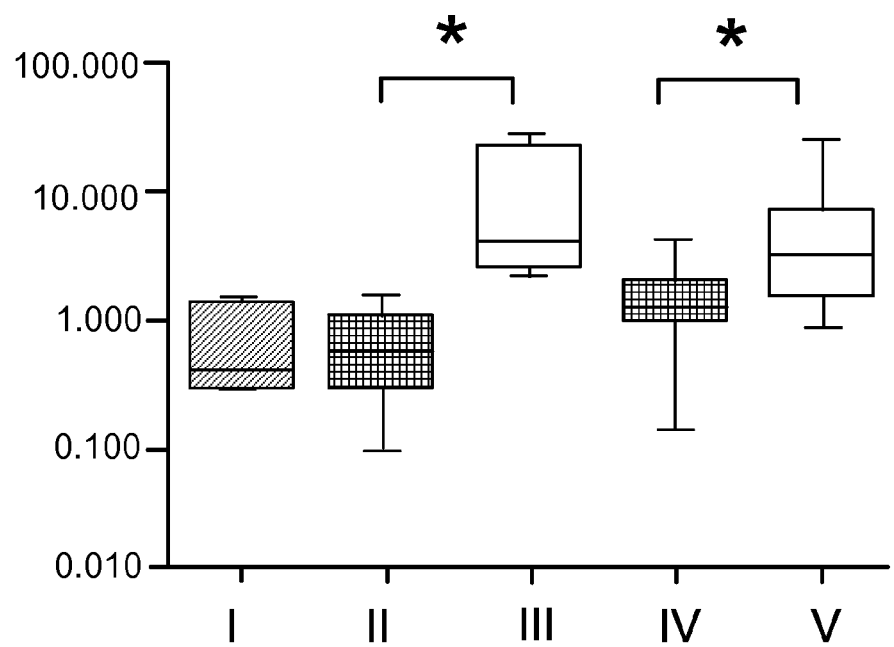

The invention is based in part on the discovery that specific nucleic acid sequences (SEQ ID NOs:1-31) or variants thereof can be used for the treatment and prognosis of melanoma.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

1. DEFINITIONS

Aberrant Proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant.

About

As used herein, the term "about" refers to +/−10%.

Administering

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Chemoembolization" means a procedure in which the blood supply to a tumor is blocked surgically or mechanically and chemotherapeutic agents are administered directly into the tumor.

Amelioration

Amelioration as used herein, refers to a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

Attached

"Attached" or "immobilized" as used herein refer to a probe and a solid support and may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe, or both. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Blood-Brain Barrier

The blood-brain barrier is a metabolic or cellular structure in the central nervous system that restricts the passage of various chemical substances and microscopic objects between the bloodstream and the neural tissue itself, while still allowing the passage of substances essential to metabolic function.

Blood Tumor Marker

Blood tumor marker as used herein means a biomarker that increases or decreases in the blood of a subject having a tumor.

Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, hair, and skin. Biological samples also include explants and primary and/or transformed cell cultures derived from animal or patient tissues.

Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, cellular content of fine needle aspiration (FNA) or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: melanoma, glioblastoma, apudoma, choristoma, branchioma, malignant carcinoid syndrome, carcinoid heart disease, carcinoma (e.g., Walker, basal cell, basosquamous, Brown-Pearce, ductal, Ehrlich tumor, small cell lung, non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Cancer Prognosis

A forecast or prediction of the probable course or outcome of the cancer and response to its treatment. As used herein, cancer prognosis includes distinguishing between cancer stages and subtypes, and the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer.

Chemotherapeutic Agent

A drug used to treat a disease, especially cancer. In relation to cancer the drugs typically target rapidly dividing cells, such as cancer cells. Non-limiting examples of chemotherapeutic agents include cisplatin, carboplatin, camptothecins, doxorubicin, cyclophosphamide, paclitaxel, etoposide, vinblastine, Actinomycin D and cloposide.

Classification

"Classification" as used herein refers to a procedure and/or algorithm in which individual items are placed into groups or classes based on quantitative information on one or more characteristics inherent in the items (referred to as traits, variables, characters, features, etc) and based on a statistical model and/or a training set of previously labeled items. According to one embodiment, classification means determination of the type of cancer.

Coadministration

The term "coadministration" or "combination therapy" is used to describe a therapy in which at least two active compounds (one of which is a compound according to the present invention) in effective amounts are used to treat melanoma, including metastatic melanoma as otherwise described herein at the same time. Although the term coadministration preferably includes the administration of two active compounds to the patient at the same time, it is not necessary that the compounds be administered-to-the patient at the same time, although effective amounts of the individual compounds will be present in the patient at the same time. Compounds according to the present invention may be administered with one or more compound including a chemotherapeutic agent such as dacarbazine (DTIC) and/or and immunotherapeutic agent such as IL-2 and/or a-interferon, among other compounds.

Complement

"Complement" or "complementary" as used herein means Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules. In some embodiments, the complementary sequence has a reverse orientation (5'-3').

Ct

Ct signals represent the first cycle of PCR where amplification crosses a threshold (cycle threshold) of fluorescence. Accordingly, low values of Ct represent high abundance or expression levels of the microRNA.

In some embodiments the PCR Ct signal is normalized such that the normalized Ct remains inversed from the expression level. In other embodiments the PCR Ct signal may be normalized and then inverted such that low normalized-inverted Ct represents low abundance or expression levels of the microRNA.

Detection

"Detection" means detecting the presence of a component in a sample. Detection also means detecting the absence of a component. Detection also means measuring the level of a component, either quantitatively or qualitatively.

Differential Expression

"Differential expression" means qualitative or quantitative differences in the temporal and/or cellular gene expression patterns within and among cells and tissue. Thus, a differentially expressed gene may qualitatively have its expression altered, including an activation or inactivation, in, e.g., normal versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated-resulting in an increased amount of transcript, or down-regulated-resulting in a decreased amount of transcript. The degree to which expression differs need only be large enough to quantify via standard characterization techniques such as expression arrays, quantitative reverse transcriptase PCR, northern analysis, real-time PCR, in situ hybridization and RNase protection.

Dose

"Dose" as used herein means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

Dosage Unit

"Dosage unit" as used herein means a form in which a pharmaceutical agent is provided. In certain embodiments, a dosage unit is a vial containing lyophilized oligonucleotide. In certain embodiments, a dosage unit is a vial containing reconstituted oligonucleotide.

Effective Amount

The term "effective amount" is used, to describe an amount of a composition, compound, or component, which produces an intended effect when used within the context of its use, which may be a diagnostic method, a therapeutic method, a method to monitor the progression of therapy or other method pursuant to the present invention. In the case of therapeutic methods, an effective amount for treating melanoma, including metastatic melanoma, is that amount which shrinks cancerous tissue (e.g., tumor), produces a remission, prevents further growth of the tumor and/or reduces the likelihood that the cancer in its early stages (in situ or invasive) does not progress further to metastatic melanoma.

Expression Profile

"Expression profile" as used herein may mean a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. The term "expression profile" may also mean measuring the abundance of the nucleic acid sequences in the measured samples.

Expression Ratio

"Expression ratio" as used herein refers to relative expression levels of two or more nucleic acids as determined by detecting the relative expression levels of the corresponding nucleic acids in a biological sample.

FDR

When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment

"Fragment" is used herein to indicate a non-full length part of a nucleic acid or polypeptide. Thus, a fragment is itself also a nucleic acid or polypeptide, respectively. Generally, fragments will be ten or more nucleotides in length.

Gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic antitumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

Host Cell

"Host cell" as used herein may be a naturally occurring cell or a transformed cell that may contain a vector and may support replication of the vector.

Identity

"Identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

In Situ Detection

"In situ detection" as used herein means the detection of expression or expression levels in the original site hereby meaning in a tissue sample such as biopsy.

"Inhibit" as used herein may mean prevent, suppress, repress, reduce or eliminate.

Label

"Label" as used herein means a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Melanoma

The term "melanoma" is used to describe a malignant tumor of melanocytes which are found predominantly in skin but also in the bowel and the eye (uveal melanoma), even though melanoma can be found in any part of the body. Melanoma is a form of cancer that begins in melanocytes, the cells that make skin pigment, or melanin. It may begin in a mole (skin melanoma), but can also begin in other pigmented tissues. There are several types of melanoma, defined by where they first appear, including skin and eye melanoma and in rare instances in the GI tract or lymph nodes. Melanoma is one of the rarer types of skin cancer but causes the majority of skin cancer related deaths. Malignant melanoma is a serious type of skin cancer. It is due to uncontrolled growth of pigment cells, called melanocytes. Despite many years of intensive laboratory and clinical research, the sole effective cure is surgical resection of the primary tumor before it achieves a Breslow thickness greater than 1 mm. Around 160,000 new cases of melanoma are diagnosed worldwide each year. About 48,000 melanoma related deaths occur worldwide per year. Malignant melanoma accounts for 75 percent of all deaths associated with skin cancer. The treatment includes surgical removal of the tumor; adjuvant treatment; chemo- and immunotherapy, or radiation therapy. The severity of melanoma is often characterized by the Clark level, which are for thin tumors and describe how deeply the cancer has spread into the skin, and the Breslow depth, which refers to the microscopic depth of tumor invasion. The following stages are identified in the progression of the melanoma disease state. Melanoma progresses from an early stage (in situ) through an invasive stage, a high risk melanoma stage, a regional metastatic stage and a distant metastatic stage with varying degrees of survivability, as set forth below. Tradition therapy of melanoma involves a number of treatment options. These generally include surgery, chemotherapy, radiation therapy and immunotherapy (IL-2, other). In the case of surgery, treatment can vary and can include local excision, wide local excision, lymphadenectomy, sentinel lymph node biopsy and skin grafting. In the case of chemotherapy, a standard chemotherapeutic agent dacarbazine (DTIC) is administered to the patient in order to treat the cancer, generally through cancer cell death. In the case of radiation therapy, radiation is used as a palliative rather than a cure for melanoma. Radiation relieves bone pain and other symptoms caused by metastases to the bones, brain, and organs such as the liver. Although not curative, radiation treatment is being investigated for more widespread use in controlling other symptoms of skin cancer. In the case of immunotherapy (biologic treatment), a patient's natural immune system is raised or other immune compositions (IL-2) are administered to the patient against the cancer.

Metastatic Melanoma

"Metastatic melanoma" refers to a progressed form of melanoma wherein the original cancer has metastasized to another area of the skin (regional or distant) or to other non-skin tissue (e.g., lungs, liver, brain, lymph system). Metastatic melanoma describes when melanoma has spread into surrounding healthy tissue and through the bloodstream, or lymphatic system, to other parts of the body. If melanoma spreads to these other areas, the cancer cells in the new tumor are still melanoma cells but the disease is called metastatic melanoma. Unlike early stages of melanoma, which can be treated successfully with early diagnosis, the prognosis for patients diagnosed with metastatic melanoma is poor, with survival rates of six to nine months. In the past 35 years, the FDA has only approved two types of therapies for metastatic melanoma-interleukin 2 (IL-2) and DTIC. The methods of treatment for metastatic melanoma include radiation, immunotherapy, chemotherapy and palliative surgery. Currently, there are no approved therapies that significantly improve survival for patients with metastatic melanoma.

Mismatch

"Mismatch" means a nucleobase of a first nucleic acid that is not capable of pairing with a nucleobase at a corresponding position of a second nucleic acid.

Modified Oligonucleotide

"Modified oligonucleotide" as used herein means an oligonucleotide having one or more modifications relative to a naturally occurring terminus, sugar, nucleobase, and/or internucleoside linkage. According to one embodiment, the modified oligonucleotide is a miRNA comprising a modification (e.g. labeled). According to another embodiment, the modified oligonucleotide is complementary to a miRNA.

Modulation

"Modulation" as used herein means a perturbation of function or activity. In certain embodiments, modulation means an increase in gene expression. In certain embodiments, modulation means a decrease in gene expression. As such, the modulation can be an increase of a cytokine level, for instance said increase of a cytokine level is at least 1.5, 2, 3 times or more relative to before said induction. Alternatively, said modulation is a decrease of the level of a particular cytokine level, for instance said decrease of the cytokine level is at least 1.5, 2, 3 times or more relative to before said induction. The cytokines may be chosen from any relevant cytokines, preferably said cytokines are chosen from the group consisting of IL-10, IL-2, IL-4, IL-6 and IL-12.

Nucleic Acid

"Nucleic acid" or "oligonucleotide" or "polynucleotide" as used herein mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005) and Soutschek et al., Nature 432:173-178 (2004), which are incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver. Mixtures of naturally occurring nucleic acids and analogs may be made; alternatively, mixtures of different nucleic acid analogs, and mixtures of naturally occurring nucleic acids and analogs may be made.

Overall Survival Time

"Overall survival time" or "survival time", as used herein means the time period for which a subject survives after diagnosis of or treatment for a disease. In certain embodiments, the disease is melanoma.

Pharmaceutical Agent

Pharmaceutical agent as used herein means a substance that provides a therapeutic effect when administered to a subject. "Pharmaceutical composition" means a mixture of substances suitable for administering to an individual that includes a pharmaceutical agent. For example, a pharmaceutical composition may comprise a modified oligonucleotide and a sterile aqueous solution. "Active pharmaceutical ingredient" means the substance in a pharmaceutical composition that provides a desired effect.

Prevention

Prevention as used herein means delaying or forestalling the onset or development or progression or lowering the incidence of a condition or disease for a period of time, including weeks, months, or years.

Progression-Free Survival

"Progression-free survival" means the time period for which a subject having a disease survives, without the disease getting worse. In certain embodiments, progression-free survival is assessed by staging or scoring the disease. In certain embodiments, progression-free survival of a subject having cancer is assessed by evaluating tumor size, tumor number, and/or metastasis.

Probe

"Probe" as used herein means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Promoter

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

Reduced Tumorigenicity

"Reduced tumorigenicity" as used herein refers to the conversion of hyperproliferative (e.g., neoplastic) cells to a less proliferative state. In the case of tumor cells, "reduced tumorigenicity" is intended to mean tumor cells that have become less tumorigenic or non-tumorigenic or non-tumor cells whose ability to convert into tumor cells is reduced or eliminated. Cells with reduced tumorigenicity either form no tumors in vivo or have an extended lag time of weeks to months before the appearance of in vivo tumor growth. Cells with reduced tumorigenicity may also result in slower growing three dimensional tumor mass compared to the same type of cells having fully inactivated or non-functional tumor suppressor gene growing in the same physiological milieu (e.g., tissue, organism age, organism sex, time in menstrual cycle, etc.).

Side Effect

Side effect as used herein means a physiological response attributable to a treatment other than desired effects.

Selectable Marker

"Selectable marker" as used herein means any gene which confers a phenotype on a host cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene.

Stringent Hybridization Conditions

"Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium).

Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" as used herein means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a human or non-human animal selected for treatment or therapy. The methods of the present invention are preferably applied to human subjects. "Subject in need thereof" refers to a subject identified as in need of a therapy or treatment. In certain embodiments, a subject is in need of treatment for melanoma. In such embodiments, a subject has one or more clinical indications of melanoma or is at risk for developing melanoma.

Target Nucleic Acid

"Target nucleic acid" as used herein means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pre-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

Therapy

"Therapy" as used herein means a disease treatment method. In certain embodiments, therapy includes, but is not limited to, modified oligonucleotide therapy, tyrosine kinase inhibition therapy, chemotherapy, surgical resection, transplant, and/or chemoembolization. "Therapeutic agent" means a pharmaceutical agent used for the cure, amelioration or prevention of a disease. "Recommended therapy" means a treatment recommended by a medical professional for the treatment, amelioration, or prevention of a disease.

Therapeutically Effective Amount

"Therapeutically effective amount" or "therapeutically efficient" used herein as to a drug dosage, refer to dosage that provides the specific pharmacological response for which the drug is administered in a significant number of subjects in need of such treatment. The "therapeutically effective amount" may vary according, for example, the physical condition of the patient, the age of the patient and the severity of the disease.

Threshold Expression Level

As used herein, the phrase "threshold expression level" refers to a reference expression value. Measured values are compared to a corresponding threshold expression level to determine the prognosis of a subject.

Tissue Sample

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Transcription Factor

As used herein, a transcription factor (sometimes called a sequence-specific DNA binding factor) is a protein that binds to specific DNA sequences and thereby controls the transfer (or transcription) of genetic information. Transcription factors perform this function alone, or with other proteins in a complex, by promoting, or blocking the recruitment of RNA polymerase to specific genes.

A defining feature of transcription factors is that they contain one or more DNA binding site (or binding domains) which attach to specific sequences of DNA adjacent to the genes that they regulate.

Treating

The term "treating" or "successfully treating" when used in the context of treating melanoma, including metastatic melanoma, shall include shrinking a tumor, curing melanoma, including melanoma which has metastazied (by causing a remission of the cancer in the patient) or reducing the likelihood or preventing the spread of the melanoma into other organs. Melanoma, including metastatic melanoma, may be treated using compounds according to the present invention alone, or in combination with other methods and/or compounds including surgery, chemotherapy (e.g., the use of the chemotherapeutic agent dacarbazine or DTIC), radiation therapy and immunotherapy (IL-2 and/or α-interferon).

Unit Dosage Form

"Unit dosage form" used herein may refer to a physically discrete unit suitable as a unitary dosage for a human or animal subject. Each unit may contain a predetermined quantity of a composition described herein, calculated in an amount sufficient to produce a desired effect in association with a pharmaceutically acceptable diluent, carrier or vehicle. The specifications for a unit dosage form may depend on the particular composition employed and the effect to be achieved, and the pharmacodynamics associated with the composition in the host.

Variant "Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Vector

"Vector" as used herein means a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

Wild Type

As used herein, the term "wild type" sequence refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

2. MICRORNAS AND THEIR PROCESSING

A gene coding for a microRNA (miRNA) may be transcribed leading to production of an miRNA precursor known as the pri-miRNA. The pri-miRNA may be part of a polycistronic RNA comprising multiple pri-miRNAs. The pri-miRNA may form a hairpin structure with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nucleotide precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of the stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repression or activation), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have studied the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 Genes-Dev 2004-504). However, other parts of the microRNA may also participate in mRNA binding. Moreover, sufficient base pairing at the 3' can compensate for insufficient pairing at the 5' (Brennecke et al, 2005 PLoS 3-e85).

Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet. 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and the binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

3. NUCLEIC ACIDS

Nucleic acids are provided herein. The nucleic acids comprise the sequence of SEQ ID NOS: 1-31 detailed below in table 1, or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

3a. Nucleic Acid Complexes

The nucleic acid may further comprise one or more of the following: a peptide, a protein, a RNA-DNA hybrid, an antibody, an antibody fragment, a Fab fragment, and an aptamer.

3b. Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof.

The pri-miRNA may form a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole, as calculated by the Vienna algorithm, with default parameters as described in Hofacker et al., Monatshefte f Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

3c. Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-31 or variants thereof 3d. miRNA The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-15 or variants thereof.

3e. Anti-miRNA

The nucleic acid may also comprise a sequence of an anti-miRNA capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA.

3f. microRNA Binding Site of Target

The nucleic acid may also comprise a sequence of a target binding site or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides.

4. SYNTHETIC GENE

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

5. VECTOR

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

6. HOST CELL

A host cell is also provided comprising a vector, synthetic gene or nucleic acid described herein. The cell may be a bacterial, fungal, plant, insect or animal cell. For example, the host cell line may be DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3×63-Ag3.653 (mouse myeloma), BFA-1c1BPT (bovine endothelial cells), RAJI (human lymphocyte) and 293 (human kidney). Host cell lines may be available from commercial services, the American Tissue Culture Collection or from published literature.

7. PROBES

A probe is provided herein. A probe may comprise a nucleic acid. The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may comprise a nucleic acid of 18-25 nucleotides.

A probe may be capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. A probe may be single stranded or partially single and partially double stranded. The strandedness of the probe is dictated by the structure, composition, and properties of the target sequence. Probes may be directly labeled or indirectly labeled.

The probe may be a test probe. The test probe may comprise a nucleic acid sequence that is complementary to a miRNA, a miRNA*, a pre-miRNA, or a pri-miRNA. The probe may further comprise a linker. The linker may be 10-60 nucleotides in length. The linker may be 20-27 nucleotides in length. The linker may be of sufficient length to allow the probe to be a total length of 45-60 nucleotides. The linker may not be capable of forming a stable secondary structure, or may not be capable of folding on itself, or may not be capable of folding on a non-linker portion of a nucleic acid contained in the probe. The sequence of the linker may not appear in the genome of the animal from which the probe non-linker nucleic acid is derived.

8. REVERSE TRANSCRIPTION

Target sequences of a cDNA may be generated by reverse transcription of the target RNA. Methods for generating cDNA may be reverse transcribing polyadenylated RNA or alternatively, RNA with a ligated adaptor sequence.

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Polyadenylated RNA may be used in a reverse transcription (RT) reaction using a poly(T) primer comprising a 5' adaptor sequence. The poly(T) sequence may comprise 8, 9, 10, 11, 12, 13, or 14 consecutive thymines The reverse transcript of the RNA may be amplified by real time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

The PCR reaction may comprise a forward primer. The forward primer may comprise 15, 16, 17, 18, 19, 20, or 21 nucleotides identical to the target nucleic acid.

The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides.

The PCR reaction may comprise a reverse primer. The reverse primer may be complementary to a target nucleic acid. The reverse primer may also comprise a sequence complementary to an adaptor sequence. The sequence complementary to an adaptor sequence may comprise 12-24 nucleotides.

9. BIOCHIP

A biochip is also provided. The biochip may comprise a solid substrate comprising an attached probe or plurality of probes described herein. The probes may be capable of hybridizing to a target sequence under stringent hybridization conditions. The probes may be attached at spatially defined locations on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrate materials include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The substrate of the biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker.

The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

10. DIAGNOSTICS

A method of diagnosis is also provided. The method comprises detecting a differential expression level of melanoma-associated nucleic acids in a biological sample. The sample may be derived from a patient. Diagnosis of a cancer state, and its histological type, in a patient may allow for prognosis and selection of therapeutic strategy. Further, the developmental stage of cells may be classified by determining temporarily expressed cancer-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

11. KITS

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials for using the kit containing directions (e.g., protocols) for the practice of the methods described herein.

For example, the kit may be used for the amplification, detection, identification or quantification of a target nucleic acid sequence. The kit may comprise a poly(T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, components for in situ hybridization and components for isolating miRNA. Other kits of the invention may include components for making a nucleic acid array comprising miRNA, and thus, may include, for example, a solid support.

12. COMPOSITIONS

A pharmaceutical composition is also provided. The composition may comprise a nucleic acid described herein and optionally a pharmaceutically acceptable carrier. The composition may encompass modified oligonucleotides that are identical, substantially identical, substantially complementary or complementary to any nucleobase sequence version of the miRNAs described herein or a precursor thereof.

In certain embodiments, a nucleobase sequence of a modified oligonucleotide is fully identical or complementary to a miRNA nucleobase sequence listed herein, or a precursor thereof. In certain embodiments, a modified oligonucleotide has a nucleobase sequence having one mismatch with respect to the nucleobase sequence of the mature miRNA, or a precursor thereof. In certain embodiments, a modified oligonucleotide has a nucleobase sequence having two mismatches with respect to the nucleobase sequence of the miRNA, or a precursor thereof. In certain such embodiments, a modified oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, a modified oligonucleotide consists of a number of linked nucleosides that is equal to the length of the mature miRNA.

In certain embodiments, the number of linked nucleosides of a modified oligonucleotide is less than the length of the mature miRNA. In certain such embodiments, the number of linked nucleosides of a modified oligonucleotide is one less than the length of the mature miRNA. In certain such embodiments, a modified oligonucleotide has one less nucleoside at the 5' terminus. In certain such embodiments, a modified oligonucleotide has one less nucleoside at the 3' terminus. In certain such embodiments, a modified oligonucleotide has two fewer nucleosides at the 5' terminus. In certain such embodiments, a modified oligonucleotide has two fewer nucleosides at the 3' terminus. A modified oligonucleotide having a number of linked nucleosides that is less than the length of the miRNA, wherein each nucleobase of a modified oligonucleotide is complementary to each nucleobase at a corresponding position in a miRNA, is considered to be a modified oligonucleotide having a nucleobase sequence that is fully complementary to a portion of a miRNA sequence.

In certain embodiments, a modified oligonucleotide consists of 15 to 30 linked nucleosides. In certain embodiments, a modified oligonucleotide consists of 19 to 24 linked nucleosides. In certain embodiments, a modified oligonucleotide consists of 21 to 24 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides. In certain embodiments, a modified oligonucleotide consists of 26 linked nucleosides. In certain embodiments, a modified oligonucleotide consists of 27 linked nucleosides. In certain embodiments, a modified oligonucleotide consists of 28 linked nucleosides. In certain embodiments, a modified oligonucleotide consists of 29 linked nucleosides. In certain embodiments, a modified oligonucleotide consists of 30 linked nucleosides.

Modified oligonucleotides of the present invention may comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide of the present invention comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose. In certain embodiments, 2'-O-methyl group is present in the sugar residue.

The modified oligonucleotides designed according to the teachings of the present invention can be generated according to any oligonucleotide synthesis method known in the art, including both enzymatic syntheses or solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC. It will be appreciated that an oligonucleotide comprising an RNA molecule can be also generated using an expression vector as is further described hereinbelow.

The compositions may be used for therapeutic applications. The pharmaceutical composition may be administered by known methods, including wherein a nucleic acid is introduced into a desired target cell in vitro or in vivo.

Methods for the delivery of nucleic acid molecules are described in Akhtar et al., (Trends Cell Bio. 2, 139, 1992). WO 94/02595 describes general methods for delivery of RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819.

The nucleic acids can be introduced into tissues or host cells by any number of routes, including viral infection, microinjection, or fusion of vesicles. Jet injection may also be used for intra-muscular administration, as described by Furth et al. (Anal Biochem 115 205:365-368, 1992). The nucleic acids can be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

The compositions of the present invention can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc.

13. TREATMENTS

A method of treatment is also provided. A subject may be diagnosed with melanoma following the administration of medical tests well-known to those in the medical profession. In certain embodiments, the present invention provides methods for the treatment of melanoma comprising administering to a subject in need thereof a pharmaceutical composition. Administration of a pharmaceutical composition of the present invention to a subject having melanoma may result in one or more clinically desirable outcomes. Such clinically desirable outcomes include reduction of tumor number or reduction of tumor size. Additional clinically desirable outcomes include the extension of overall survival time of the subject, and/or extension of progression-free survival time of the subject. In certain embodiments, administration of a pharmaceutical composition of the invention prevents an increase in tumor size and/or tumor number. In certain embodiments, administration of a pharmaceutical composition of the invention prevents the recurrence of tumors. Administration of a pharmaceutical composition of the present invention results in desirable phenotypic effects. A subject's response to treatment may be evaluated by tests similar to those used to diagnosis the melanoma. Response to treatment may also be assessed by measuring biomarkers in blood, for comparison to pre-treatment levels of biomarkers.

The compounds provided herein may be useful for the treatment of melanoma.

Tumor treatments often comprise more than one therapy. As such, in certain embodiments the present invention provides methods for treating melanoma comprising administering to a subject in need thereof a pharmaceutical composition of the present invention, and further comprising administering at least one additional therapy.

In certain embodiments, an additional therapy may also be designed to treat melanoma. An additional therapy may be a chemotherapeutic agent. An additional therapy may be surgery.

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain such embodiments, the additional therapy is selected to treat or ameliorate a side effect of one or more pharmaceutical compositions of the present invention. Such side effects include, without limitation, injection site reactions, liver function test abnormalities, renal function abnormalities, liver toxicity, renal toxicity and central nervous system abnormalities.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, suitable administration routes of a pharmaceutical composition for the treatment of melanoma include, but are not limited to, oral, rectal, transmucosal, intestinal, enteral, topical, suppository, through inhalation, intrathecal, intraventricular, intraperitoneal, intranasal, intraocular, intratumoral, and parenteral (e.g., intravenous, intramuscular, intramedullary, and subcutaneous). An additional suitable administration route includes chemoembolization. In certain embodiments, pharmaceutical intrathecals are administered to achieve local rather than systemic exposures. For example, pharmaceutical compositions may be injected directly in the area of desired effect (e.g., into a tumor).

In certain embodiments, a pharmaceutical composition of the present invention is administered in the form of a dosage unit (e.g., tablet, capsule, bolus, etc.). In certain embodiments, such pharmaceutical compositions comprise a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the formulation.

In certain embodiments, pharmaceutical compositions of the present invention comprise one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulosem and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., crosslinked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like.

Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount of the pharmaceutical composition of the present invention is sufficient to prevent, alleviate or ameliorate symptoms of a disease or to prolong the survival of the subject being treated. Determination of a therapeutically effective amount is well within the capability of those skilled in the art.

In certain embodiments, the pharmaceutical composition of the present invention is formulated as a prodrug. In certain embodiments, upon in vivo administration, a prodrug is chemically converted to the biologically, pharmaceutically or therapeutically more active form of the composition. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Mechanisms for drug targeting in the brain involve going either "through" or "behind" the blood-brain barrier. Modalities for drug delivery through the blood-brain barrier entail its disruption by osmotic means, biochemically by the use of vasoactive substances such as bradykinin, or even by localized exposure to high intensity focused ultrasound (HIFU). Other strategies to go through the blood brain barrier may entail the use of endogenous transport systems, including carrier-mediated transporters such as glucose and amino acid carriers; receptor-mediated transcytosis for insulin or transferrin; and blocking of active efflux transporters such as p-glycoprotein. Strategies for drug delivery behind the blood-brain barrier include intracerebral implantation and convection-enhanced distribution. In some embodiments the compounds may be administered by infusion pump to be delivered to the blood brain barrier.

The following examples are presented in order to more fully illustrate some embodiments of the invention. They should, in no way be construed, however, as limiting the broad scope of the invention.

EXAMPLES

Example 1

Materials and Methods

RNA Extraction:
Total RNA was isolated from seven to ten 10-μm-thick tissue sections using the microRNA extraction protocol developed at Rosetta Genomics. Briefly, the sample was incubated repeatedly in Xylene at 57° C. to remove paraffin excess, followed by repeated ethanol washes. Proteins were degraded by proteinase K solution at 45° C. for a few hours. The RNA was extracted with acid phenol:chloroform, followed by ethanol precipitation and DNAse digestion. Total RNA quantity and quality was checked by spectrophotometer (Nanodrop ND-1000).

microRNA Array Platform:
Custom microarrays were produced by printing DNA oligonucleotide probes representing 911 human microRNAs. Each probe, printed in triplicate, carries a linker up to 22 nt long at the 3' end of the complement sequence of the microRNA, in addition to an amine group used to couple the probes to coated glass slides. 20 μM of each probe were dissolved in 2×SSC+0.0035% SDS and spotted in triplicate on Schott Nexterion® Slide E-coated microarray slides using a Genomic Solutions®BioRobotics MicroGrid II, according to the MicroGrid manufacturer's directions. Fifty-four negative control probes were designed using the sense sequences of different microRNAs. Two groups of positive control probes were designed to hybridize to a miRNArray: (i) synthetic small RNA were spiked to the RNA before labeling to verify the labeling efficiency and (ii) probes for abundant small RNA (e.g., small nuclear RNAs (U43, U49, U24, Z30, U6, U48, U44), 5.8 s and 5 s ribosomal RNA) were spotted on the array to verify RNA quality. The slides were blocked in a solution containing 50 mM ethanolamine, 1 M Tris (pH 9.0) and 0.1% SDS for 20 min at 50° C., then thoroughly rinsed with water and spun dry.

Cy-Dye Labeling of microRNA for microRNA Array:

Five μg of total RNA were labeled by ligation (Thomson et al., Nature Methods 2004; 1:47-53) of an RNA-linker, p-rCrU-Cy/dye (Dharmacon), to the 3' end with Cy3 or Cy5. The labeling reaction contained total RNA, spikes (0.1-20 fmoles), 300 ng RNA-linker-dye, 15% DMSO, 1× ligase buffer and 20 units of T4 RNA ligase (NEB) and proceeded at 4° C. for 1 h, followed by 1 h at 37° C. The labeled RNA was mixed with 3× hybridization buffer (Ambion), heated to 95° C. for 3 min and then added on top of the microarray. Slides were hybridized 12-16 h in 42° C., followed by two washes in room temperature with 1×SSC and 0.2% SDS and a final wash with 0.1×SSC. Arrays were scanned using an Agilent Microarray Scanner Bundle G2565BA (resolution of 10 μm at 100% power). Array images were analyzed using SpotReader software (Niles Scientific).

Statistical Analyses:

Differential expression was performed in log-space, comparing logs of readings of the microarray data. Differentially expressed miRNAs were identified by using the t-test based procedure called significance analysis of microarrays ("SAM". Tibshirani, R., Hastie, T., Narasimhan, B. & Chu, G., journal 2002). SAM produces a score for each gene on the basis of the expression change relative to the standard deviation of all expression levels. This procedure allows the control of false discovery rate (FDR). FDR analysis was performed using the Benjamini & Hochberg process, using an FDR rate of 0.15.

Quantitative Real-Time PCR (qRT-PCR):

Total RNA was extracted using the miRNeasy Mini Kit (Qiagen). qRT-PCR analysis was performed by using miRNA-specific TaqMan MicroRNA Assay Kit (Applied Biosystems). 12.5 ng of total RNA was reversed transcribed using the corresponding RT Primer and the TaqMan MicroRNA Reverse Transcription Kit (Applied Biosystems). PCR was performed on 1.33 ul of RT products by adding the TaqMan PCR primers and the TaqMan Universal PCR Master Mix (Applied Biosystems). U6 and RNU44 small RNAs were used for normalization of input RNA/cDNA levels.

Oligonucleotide Transfection:

miRIDIAN oligonucleotides (Dharmacon) were transfected using Lipofectamine 2000 (Invitrogen) according to suggested manufacturer procedures. Transfection efficiency was monitored using BLOCK-iT Fluorescent Oligo (Invitrogen).

Lentiviral-Mediated Gene Transduction:

Lentiviruses were propagated using previously described methods (Naldini et al., Science 272:263-267). Briefly, 293T cells were cotransfected with the vector of interest and helper plasmids. Melanoma cells were transduced with the supernatant of 293T cells supplemented with polybrene (2 ug/ml). Pools of cells stably transduced were selected by adding puromycin (2 μg/ml) to the culture medium (Gibco/Invitrogen).

Preclinical Model of Melanoma B-Met:

A new preclinical model of melanoma B-Met was utilized as described by Cruz-Munoz et al., (Cancer research 2008, 68(12):4500-4505). This model seems to recapitulate all the steps involved in the metastatic cascade and enables a more relevant investigation of the mechanisms governing the tropism of melanoma cells to the brain. A highly metastatic variant of the WM239A human melanoma cell line (113/6-4L) was selected and used to generate metastatic disease in NOD/SCID mice. Mice were then subjected to a long-term, low-dose metronomic chemotherapy that resulted in advanced systemic disease with prolonged survival. 20% of surviving mice developed spontaneous B-Met and two cell lines (131/4-5B1 and 131/4-5B2) were established from such metastases. These cell lines were then proven to spontaneously metastasize to brain parenchyma after orthotopic transplantation and removal of the primary tumor (Cruz-Munoz et al., Cancer Res. 2008 Jun. 15; 68(12):4500-5).

Cell Lines.

Cell lines were cultured as previously described (Segura et al., 2009). HEK293T and A375 cells were purchased from American Type Culture Collection (ATCC). The B16F10 mouse melanoma cell line and the human WM35 and WM98 cell lines were acquired from the Wistar Institute. Cell lines 113/6-4L (4L) and 131/4-5B1 (5B1) were isolated and cultured as previously described (Cruz-Munoz et al., 2008). 4L, 5B1, A375 and B16F10 are metastatic melanoma cell lines whereas WM35 and WM98 were derived from primary melanomas.

FFPE DNA Isolation.

Sections containing ≥80% tumor cells were used. Melanoma cells were identified by inspection of the H&E staining or by immunostaining using a cocktail of antibodies directed against the melanoma markers Melan-A, S100, and HMB45. Depending on tumor size, 3 to 7 sections, each 10 μm thick, were used per DNA purification. DNA was purified using the QIAamp DNA FFPE Tissue Kit (Qiagen), with small variations of the manufacturer's protocol.

Gene Copy Number Analysis.

2 ng of DNA isolated from FFPE tissues were used for the qPCR reaction: an initial step of 95° C. for 15 min followed by 40 cycles of 95° C. for 10 s, 63.3° C. for 30 s and 72° C. for 30 s, followed by 71 steps of 0.5° C. increments from 60 to 95° C. Human genomic DNA (Promega, Madison Wis., cat #G304A) was used as control. All the primers, except those for UBE2E1, were designed using NCBI primer blast (Rozen and Skaletsky, 2000). Data were normalized to 2 control genomic loci (GNS and UBE2E1).

Plasmids.

Plasmids containing the luciferase cDNA conjugated to the 3'UTR of HDAC9, FAP, TWF1, GALNT7, ITGA6 and BCL6 were purchased from SwitchGear. A plasmid containing the luciferase cDNA conjugated to the 3'UTR of CESLR3 was purchased from Genecoopia. Plasmids containing the 3'UTR of SEMA3A and GALNT1 were generated by cloning 3'UTR fragments of 440 bp and 1839 bp, respectively, into the psiCHECK™-2 plasmid (Promega). Human GALNT7 expression vector was purchased from Open Biosystems and the cDNA sequence with truncated 3'UTR (no miR-30b/d sites) was sub-cloned into pEIGW lentiviral vector. A fragment of 2213 bp, containing the coding sequence of mmu-GALNT7 with truncated 3'UTR (no miR-30b/d sites), was subcloned from pYX-Asc-mmuGALNT7 (Open Biosystems) using NotI/SalI, and inserted in pEIGW. A lentiviral vector expressing miR-30d was generated by cloning the pre-miR sequence (and spanning sequence approximately 200 bp up/downstream) into the pGIPZ plasmid (Open Biosystems). Scrambled control vector was purchased from Open Biosystems. Plasmid mutagenesis. 25-90 ng of plasmid containing the 3'UTR of SEMA3A, GALNT1 or GALNT7 was mutated using the QuickChange XL Site-Directed mutagenesis Kit (Stratagene). PCR cycle onsisted of an initial step of 95° C. for 5 min., followed by 18 cycles of 95° C. for 1 min., 60° C.-64° C. for 50 s, and 68° C. for 8 minutes, followed by an elongation step of 68° C. for 7 minutes.

Oligonucleotide Transfection.

MiRIDIAN oligonucleotide mimics and anti-miRNAs (Dharmacon) were transfected using Lipofectamine 2000 (Invitrogen) according to the manufacturer's procedures. Transfection efficiency was monitored using BLOCK-iT Fluorescent Oligo (Invitrogen). For rescue experiments, 5 µg/ml of either GALNT7 or empty expression vectors were co-transfected with either miR-30b/30d or scr control using Lipofectamin 2000 (Invitrogen).

Viral-Mediated Gene Transduction.

Lentiviruses were produced using described methods. Melanoma cells were transduced with lentiviral supernatants supplemented with polybrene (2 µg/mL). Pools of stably transduced cells were selected by adding puromycin (2 µg/mL) to the culture medium (Gibco/Invitrogen).

Luciferase Assays.

HEK293T were seeded into 96-well plates and co-transfected with 3'UTR vectors and indicated amounts of miR-30b or -30d mimics or miRIDIAN mimic negative control (Dharmacon). Luciferase activity was measured using the Dual-Glo™ Luciferase Assay System (Promega). Renilla luciferase activity was normalized to corresponding firefly luciferase activity and plotted as a percentage of the control.

Fibronectin Transwell Invasion Assay.

A suspension of $2-4\times10^4$ was added to cell culture inserts (Falcon) containing a polycarbonate filter with 8 µm diameter pores coated with fibronectin (10 µg/ml) and blocked with 2.5% BSA. Cells were incubated for 14-17 hours under standard culture conditions. Tumor cells remaining on the topside of the membrane were removed, and cells that had migrated to the underside were fixed and stained with crystal violet. Five fields per insert were photographed and scored.

In Vivo Metastasis Assays.

Model of Murine Lung Metastasis.

Subconfluent B16F10 cells (transfected with scrambled, anti-miR30d oligonucleotides, miR-30d mimic, both miR-30d and miR-30b mimics or siGALNT7 (to a final concentration of 150 nM) were injected intravenously ($1.0\times10^5$/ 100 µl/mouse for all experiments except the siGALNT7 experiment (FIG. 14C) in which $2.5\times10^5$/1000/mouse) into 8-12 weeks old C57BL/6J mice. After 10 to 14 days (or 8 days for siGALNT7 experiment), mice were sacrificed, their lungs removed and fixed, and the number of isolated and discrete pigmented lung surface lesions counted on each lobe of every specimen. Tissues were paraffin-embedded, and 5 µm sections were H&E-stained. The same procedure was performed for GALNT7 rescue experiments with the following alterations: B16F10 cells were stably transduced with PEIGW-empty or PEIGW-mmuGALNT7. 24 h prior to injection cells were transfected with scrambled or miR-30d mimic (150 nM). $2.0\times10^5$/100 µl/mouse were injected.

Model of Lung Metastasis Using Human Primary Melanoma Cells.

$0.75\times10^6$ WM98 cells stably transduced with either pGIPZ-scr or pGIPZ-miR-30d were injected intravenously ($1.0\times10^6$/100 µl/mouse) into 8-12 weeks old NOD/Shi-scid/ IL-2R $\gamma_{nul}$; (NOG/SCID; Jackson Labs) mice (n=14 mice/scr group and 17 mice/30d group). 40 days post inoculation mice were sacrificed, and their lungs and liver removed and fixed. Tissues were paraffin-embedded, and 5 µm sections were H&E-stained. The number and size of metastatic foci were evaluated by a pathologist Pre-Clinical Model of Human Melanoma Metastasis.

$0.7\times10^6$/100 µl of 5B1 cells stably transduced with either pGIPZ-scr or pGIPZ-miR-30d were mixed with 100 µl of matrigel (BD Biosciences). Cells were injected subcutaneously into the flanks of 8-12 weeks old NOD/Shi-scid/IL-2R$\gamma_{nul}$ (NOG/SCID; Jackson Labs) mice (n=20 mice/group). 80 days post inoculation, tumors, lungs and livers of mice were harvested and paraffin-embedded. Sum sections were H&E-stained; the number and size of metastatic foci were scored by a pathologist.

Ex Vivo T Cell Activation, Followed by FACS Analysis

CD4+ splenocytes were isolated from the spleens of Foxp3-GFP mice using a CD4+ T Cell Isolation Kit (Miltenyi Biotec). $1\times10^6$ cells were then incubated in a 24 well with conditioned media of melanoma cells supplemented with 25 µl of CD3/CD28 Tactivators beads (Invitrogen). FACS analysis was performed after 72 h on cells stained for CD4 (APCCy7-conjugated; BioLegend), CD25 (APC-conjugated; e bioscience) and CD69 (PE-conjugated; BD Biosciences) as described in the following FACS analysis section.

FACS Analysis of Mouse Tissue.

One lobe of lung from each mouse was minced and digested for 30 minutes at 37° C. in the presence of 30 µg/ml collagenase mix (blenzyme) in HBSS. Completely digested lungs were then spun down at 800 g and pellets were resuspended in FACS buffer (PBS, 1% BSA, 0.1% EDTA). Cells were pretreated with the FcγR-blocking mAb 2.4 G2 and analyzed with a 3-laser 10-color BD LSRII cytometer (BD Biosciences) and FACS Express software (De Novo Software). After an initial gating on forward-versus-side scatter plots, lung cell populations were gated on all viable leukocytes using the nucleic acid dye 7-aminoactinomycin D (7-AAD; BD Biosciences) and Pacific Orange—conjugated anti-CD45 antibodies (clone 30-F11; Invitrogen). Subsets of populations were defined using antibodies against MHCII (M5), Ly-6C (AL21, HK1.4), F4/80 (BM8, C1:A3-1), CD11c (HL3), CD11b (M1/70), CD86 (GL-1), GR1 and Foxp3 (purchased from BD Biosciences, BioLegend, eBioscience, or AbD Serotec and variously conjugated to Pacific Blue, FITC, PE, PE-Cy7, APC, APC-Cy7, or Alexa Fluor 700). Foxp3-labeled cells were pretreated for intracellular staining using a Foxp3 staining buffer kit(eBioscience).

Cytokine Arrays.

Cytokine antibody array (Raybiotech) was performed with 1 ml of low serum (0.5%) conditioned media of 4L and 5B1 melanoma cell lines according to the manufacturer's protocol.

ELISA.

IL-10 detection in conditioned media was performed using a Human IL-10 ELISA Set (BD Bioscience) according to the manufacturer's protocol. pSTAT3 (Tyr-705), p38 and pNF-IB levels were measured by a PathScan solid phase sandwich ELISA kit (Cell Signaling) following the manufacturer's protocol.

Western Blotting.

Cell lysates were harvested with 2% sodium dodecyl sulfate (SDS)-125 mM Tris/HClpH 7.4 or for non-denaturing conditions using commercial cell lysis buffer (Cell Signaling) supplemented with protease and phosphatase inhibitors (Roche). Cell lysates (25-30 μg of protein) were resolved in Tris/glycine SDS/PAGE gels (Invitrogen) and transferred to PVDF membranes (Invitrogen). Membranes were probed with primary antibodies overnight at 4° C. [pTyr705-STAT3, STAT3 (Cell Signaling), Tubulin (Sigma)]. Membranes were developed with the ECL Plus Western blotting detection kit (GE Healthcare) or the Lycor Odissey.

Immunohistochemistry.

Immunohistochemistry was performed on formalin fixed, paraffin embedded tissue using FOXP3 (EBiosciences) and HMBA-45 (Ventana, catalog#790-4366) antibodies in human samples. The complex was visualized with Naphthol-AS-MX phosphatase and Fast Red complex, and nuclei counterstained with hematoxylin Immunoreactivity was scored by the percentage of positive cells.

Immunofluorescence.

Tissues were fixed overnight in 10% formalin, embedded in paraffin, and sectioned at 5 υm. Immunostaining was performed with biotin-tyramide amplification (Perkin Elmer) essentially as described previously (Collins et al., 2009). FoxP3 immunostaining was performed using biotin-conjugated rat anti-mouse FoxP3 antibodies (clone FJK-16s, eBioscience; 1/1000 dilution), HRP conjugated streptavidin (Jackson ImmunoResearch), and streptavidin-conjugated Alexafluor 594 (Invitrogen). Antigen retrieval was achieved by microwaving the sections in citrate buffer. CD3 immunostaining was performed using rabbit anti-mouse CD3 antibodies (Dako, 1/3000 dilution), HRPconjugated donkey anti-rabbit antibodies (Jackson ImmunoResearch), and streptavidin-conjugated Alexafluor 594. Antigen retrieval was achieved using trypsin. Sections were counterstained with DAPI. Microscopy was performed with an AxioImager M1 microscope and AxioVision software (Carl Zeiss Microlmaging).

Clinical Specimens.

Human melanoma specimens (primary, metastatic) were collected at the time of surgery. Approval to collect specimens was granted by IRB protocol number #10362, "Development of an NYU interdisciplinary melanoma cooperative group: A clinicopathological database".

Array Profiling and Bioinformatics.

Expression profiling of the duplicate experimental sample groups (4L and 5B1 cells 60 h post-transfection with scramble and miR-30d oligonucleotides) was performed using Affymetrix Genechip system. Total RNA was extracted using the miRNeasy Mini Kit (Qiagen). Total RNA quality and quantity was determined using Agilent 2100 Bioanalyzer and Nanodrop ND-1000. 100 ng of total RNA were used to prepare cRNA following the Affymetrix 3'IVT Express Kit labeling protocol. Standardized array processing procedures recommended by Affymetrix included hybridization, fluidics processing and scanning of the Affymetrix HG-U133 Plus 2.0 arrays. GeneSpring GX11 software (Agilent Technologies, Santa Clara, Calif.) was used to normalize the raw data (Affymetrix CEL files) by Robust Multichip Average algorithm (RMA) (Irizarry et al., 2003), to filter and to perform differential abundance analyses using T-test statistics ($p<0.05$ alpha level) and fold-change thresholding (>33% reproducible change). The functional annotations of resulting gene lists were performed using the NIH web based tool DAVID (Database for Annotation, Visualization and Integrated Discovery) (Huang da et al., 2009) and/or Gene Set Enrichment Analysis (GSEA, http://www.broadinstitute.org/gsea/) (Subramanian et al., 2008).

Lectin Microarrays.

Samples processing and hybridization were carried out as previously described (Krishnamoorthy et al., 2009). Briefly, 5B1 cells were transiently transfected with scr; miR-30d; siGALNT7 or miR-30d+GALNT7, grown to 80-90% confluency and lysed using 0.5 M EDTA. Membranes were isolated after sonication as "cellular micellae." These cellular micellae were then labeled by coupling of either Cy3-NHS or Cy5-NHS on protein lysines. Two ng of protein for the appropriate Cy3- and Cy5-labeled samples were hybridized (for single color analysis) or mixed and hybridized (for dual color analysis) to each lectin microarray. Lectin microarrays were printed with a Nano-Plotter 2.1 (GeSiM, Groberkmannsdorf, Germany) using Nano-Tip-A piezoelectric printing tips with print buffers as described in previous literature with the exception that BSA is omitted and 0.01% Tween-20 is added. After washing, the arrays were scanned using a GenePix Pro 4300A scanner. Data were extracted by using GenePix Pro 7.1, analyzed, and annotated by using known lectin specificities.

Statistical Methodologies.

Figure 1E:
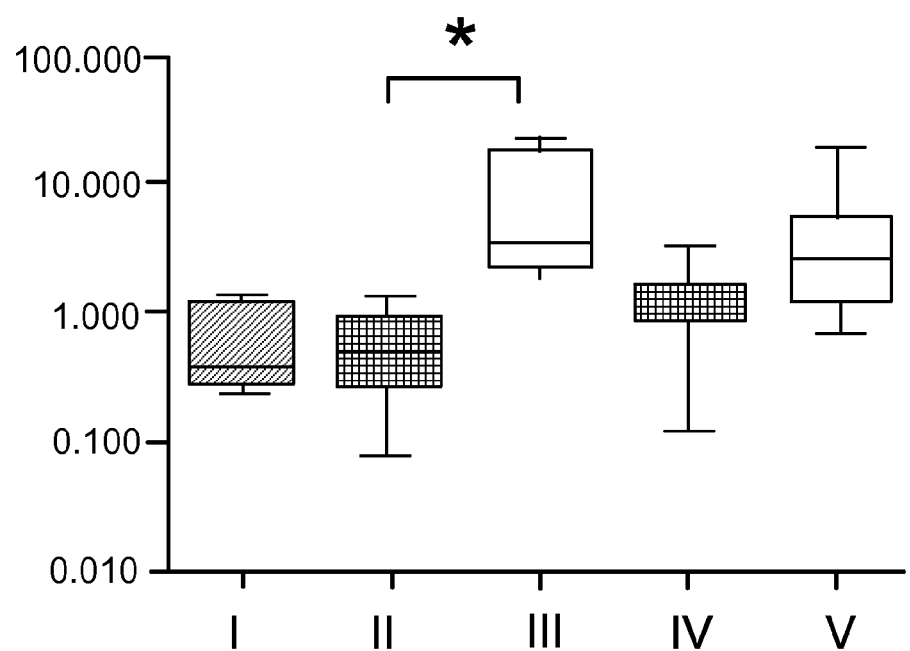
Figure 1F:
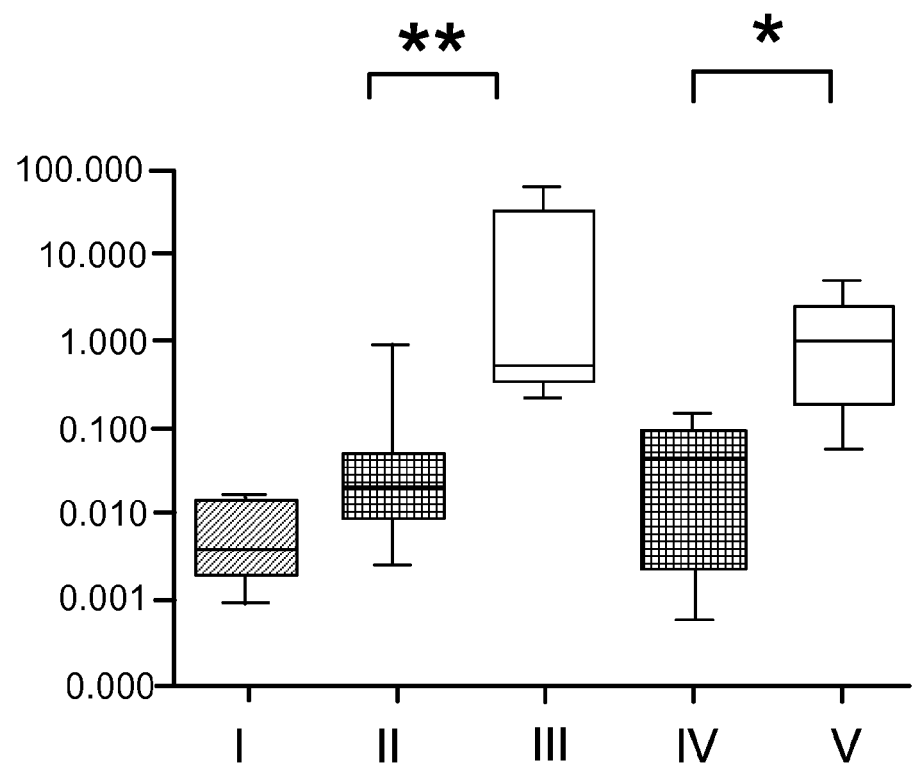
FIG. 1F demonstrates that miR-451 (SEQ ID NO: 10) has higher expression in metastasis compared to primary tumors. The Y-axis shows the relative expression in log scale.*p<0.05, I—benign nevi, II—primary of brain mets., III—brain mets., IV—primary of other mets., V—other mets.
Figure 20A:
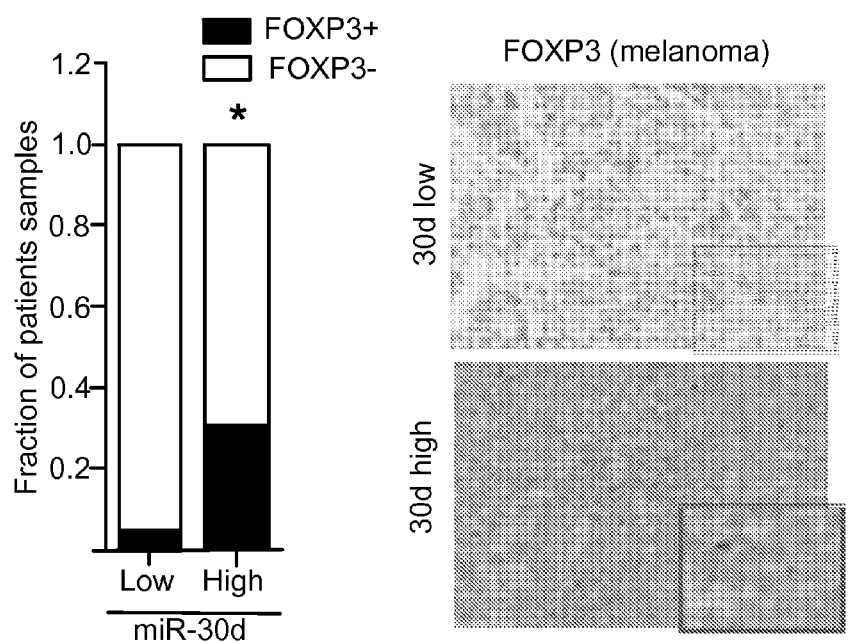

Statistical significance was determined by paired or unpaired t-test in cases of standardized expression data. One-way ANOVA was performed for multiple group comparisons (GraphPad Prism Software). Wilcoxon matched pairs test and Mann-Whitney tests for nonparametric analyses of non-Gaussian data. Chi-square test and McNemar's test was used for testing association among unmatched and matched categorical variables. In particular, chi-square test and Fisher's exact test were used to assess association of miR-30d with FOXP3 staining in T-cells and in melanoma cells as displayed in FIG. 20A. Analysis using multivariable COX PH models indicated that overexpression of miR-30b/d was a statistically significant independent predictor of shorter time-to-recurrence and lower overall survival when adjusted for primary tumor thickness and ulceration status. Log rank test was used to show the statistically significant difference in survival profiles between the group with miRNA expression levels lower than the sample median and group higher than the median, and the Kaplan-Meier survival curves were presented in FIGS. 1E and 1F.

Example 2

A Robust miRNA Signature Associates with Melanoma Brain Metastasis in Two Separate Cohorts miRNA microarrays were used to identify a "signature" of miRNAs differentially altered in melanoma brain metastasis compared to other sites of metastasis. RNA was extracted from 59 metastatic melanoma tissue specimens provided by the Biospecimen Core of the NYU interdisciplinary Melanoma Cooperative Group (IMCG, PI Osman) and hybridized to a microRNA array platform (Rosetta Genomics, Israel) containing 911 human miRNA oligonucleotide probes in triplicate. Raw intensity values were obtained from the arrays and normalized values were calculated. The preliminary cohort consisted of 11 tissues from melanoma brain metastasis and 48 tissues from other sites of distant metastatic (e.g., liver, lung, lymph node). Analysis revealed a set of 15 miRNAs differentially expressed between brain metastatic tissue and tissue from other metastatic sites ($p<0.01$).

The expression of the majority of differentially expressed miRNAs was validated in an independent cohort of 9 tissues from melanoma brain metastasis and 27 tissues from other sites of distant metastatic. These miRNAs are indicated in Table 1.

The array results were confirmed for 7 miRNAs using quantitative RT-PCR (qRT-PCR) analyses.

The primary melanomas from a subset of patients (n=20) with distant metastases were assessed to determine if the pattern of differential miRNA expression seen in the metastatic tissue was also present in the primary melanoma. It was observed that some of these differentially expressed miRNAs (e.g. miR-199a-5p (SEQ ID NO: 2), miR-199a-3p (SEQ ID NO: 4) and miR-214 (SEQ ID NO: 1)) were also differentially expressed in the corresponding primary tumors from the same patient (FIGS. 1A-1F). This finding may allow identifying melanoma patients at higher risk of developing brain metastases at the time of diagnosis.

Several miRNAs, indicated in Table 1 (bold), were selected for further study because they are the most likely to represent a unique molecular profile of melanoma brain-Met.

Seven of the miRNAs comprising the melanoma brain-Met signature may be responsible for modulating some of the critical cellular processes required for the development of melanoma brain-Mets. It is important to note that some of these altered miRNAs cluster together in the genome and are processed from the same transcript (miR-214 and miR199a on chromosome 1, and miR-30b and miR-30d on chromosome 8). This observation further supports the idea that these alterations in miRNAs are not merely random, passenger events but might play a significant role in driving the melanoma cells' tropism to the brain.

TABLE 1 miRs differentially expressed in melanoma brain-Met vs. other sites of distant metastases

| miR name | p-value | Up (+)/ down (−) | Fold-change | Median values | | miR SEQ ID NO. | Hairpin SEQ ID NO. |
|---|---|---|---|---|---|---|---|
| hsa-miR-214 | 1.1e−006 | − | 11.81 | 1.4e+003 | 1.2e+002 | 1 | 16 |
| hsa-miR-199a-5p | 1.6e−006 | − | 5.66 | 3.9e+003 | 7.0e+002 | 2 | 17, 18 |
| hsa-miR-150 | 1.7e−003 | − | 4.64 | 6.0e+002 | 1.3e+002 | 3 | 19 |
| hsa-miR-199a-3p | 2.2e−004 | − | 4.27 | 1.1e+003 | 2.5e+002 | 4 | 17, 18 |
| hsa-miR-886-5p | 3.3e−003 | − | 4.15 | 5.2e+002 | 1.2e+002 | 5 | 20 |
| hsa-miR-143 | 1.5e−005 | − | 3.23 | 3.2e+003 | 1.0e+003 | 6 | 21 |
| hsa-miR-497 | 1.2e−003 | − | 3.17 | 5.8e+002 | 1.8e+002 | 7 | 22 |
| hsa-miR-30d | 2.4e−005 | + | 2.95 | 3.3e+003 | 9.8e+003 | 9 | 24 |
| hsa-miR-145 | 2.5e−006 | − | 2.85 | 7.3e+003 | 2.6e+003 | 8 | 23 |
| hsa-miR-451 | 1.1e−003 | + | 2.78 | 5.9e+002 | 1.6e+003 | 10 | 25 |
| hsa-miR-30b | 9.5e−005 | + | 2.42 | 1.4e+003 | 3.4e+003 | 11 | 26 |
| hsa-miR-151-5p | 2.5e−003 | + | 1.62 | 1.6e+003 | 2.6e+003 | 12 | 27 |
| hsa-miR-425 | 4.1e−003 | + | 1.49 | 4.1e+002 | 6.1e+002 | 13 | 28 |
| hsa-miR-30c | 6.6e−003 | + | 1.41 | 1.5e+003 | 2.1e+003 | 14 | 29, 30 |
| hsa-miR-17 | 5.0e−003 | + | 1.33 | 9.6e+002 | 1.3e+003 | 15 | 31 |

The miR name is the miRBase registry name (release 9.1 or 10). Up-regulated (+) means higher expression in brain mets.

Example 3

Modulation of B-Met-Associated miRNAs Confers Metastatic Melanoma Cells with Increased Ability to Reach and Inhabit the Brain Environment In Vitro There are several possible mechanisms that may be responsible for melanoma's predilection to metastasize to the brain: i) primary tumor cells may be chemo-attracted to the brain by a gradient of chemokines secreted by brain cells; ii) melanoma cells may acquire increased ability to adhere to and trans-migrate through the blood brain barrier (BBB); iii) melanoma cells may have an increased capability to populate a brain-specific microenvironment. To test whether modulation of specific miRNAs produces an effect on any of these processes, melanoma cell lines were utilized of varying metastatic potential in a xenograft mouse model (Cruz-Munoz, 2008, *Cancer research* 68(12):4500-4505). The 113/6-4L (4L) cell line is an aggressive, highly metastatic melanoma cell line that does not metastasize to the brain even if survival is prolonged using metronomic chemotherapy. Conversely, cell lines 131/4-5B1 (5B1) and 131/4-5B2 (5B2), derivates of 4L, have an increased ability to colonize the brain in a shorter period of time.

One of the biggest impediments to malignant colonization of the brain is the successful penetration of the BBB. To evaluate whether modulation of B-Met-specific miRNAs can affect that process, an in vitro system of primary immortalized human brain endothelial cells (HCMEC/D3) was established that successfully recapitulate the structural and molecular features of the BBB (Weksler, 2005, *Faseb J* 19(13):1872-1874). A monolayer of HCMEC/D3 cells is plated on a 6-well plate (for adhesion experiments) or on tissue culture trans-well inserts (for trans-migration experiments). When these cells reach confluency, equal numbers of transduced or control melanoma cells are added. The number of cells that firmly adhere to HCMEC/D3 monolayer (for adhesion experiments) or trans-migrate through the monolayer (for trans-migration experiments) is determined (protocols adapted from (Cruz-Munoz, 2008, *Cancer research* 68(12):4500-4505; Bos, 2009, *Nature* 459(7249): 1005-1009).

Figure 2:
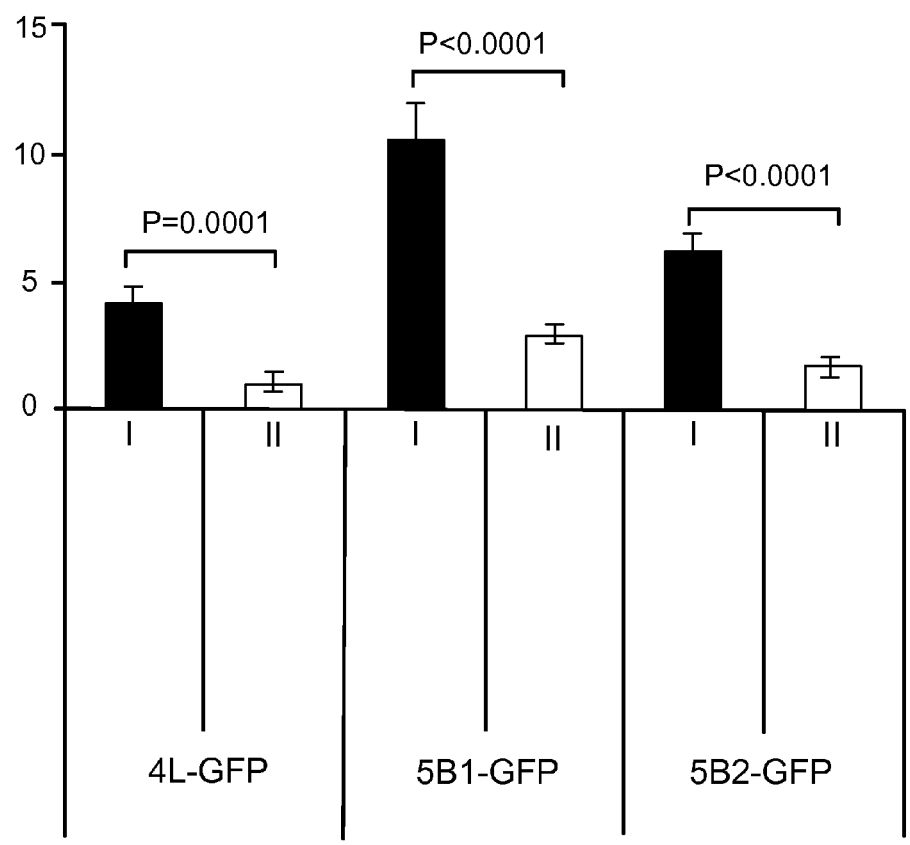
FIG. 2 demonstrates that miR-30d (SEQ ID NO: 9) silencing impairs melanoma cell adhesion. Adhesion experiment on scrambled (I) or anti-miR-30d (II) transduced melanoma cell lines (4L, 5B1 and 5B2 stably transduced with GFP-expressing lentivirus). 72 h post transduction, the cells were plated on top of HCMEC/D3 brain endothelial cells for 15 min. Plates were then washed and adhered GFP positive cells/field were counted. The Y-axis shows the average number of adhered cells/field.
Figure 3A:
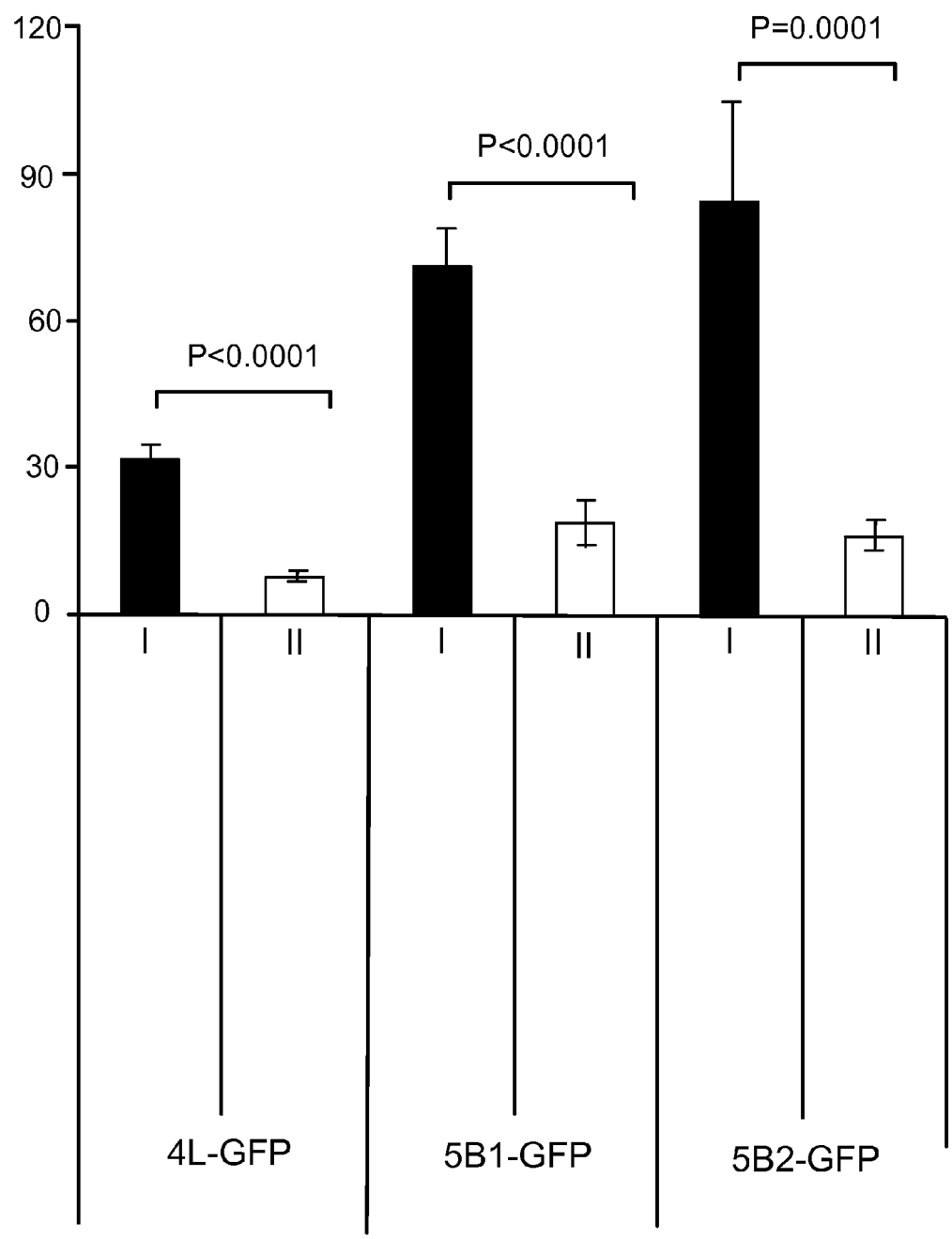
FIGS. 3A-3B demonstrate the results of trans-migration experiment in miR-199a-3p (SEQ ID NO: 4)-transduced melanoma cells.
Figure 3B:
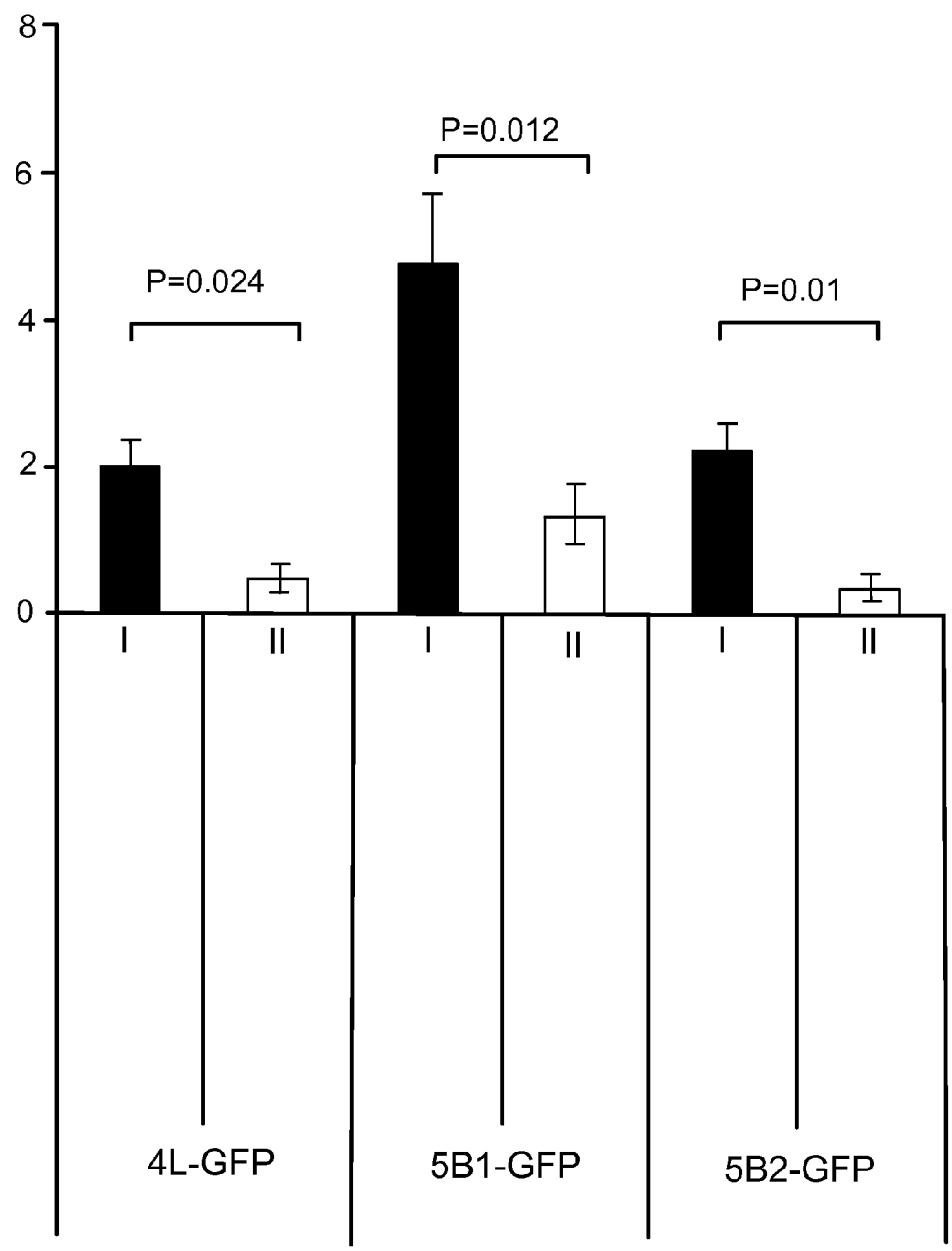

The ability of the parental model cell lines to adhere to a monolayer of HCMEC/D3 cells was examined. The 5B1 and 5B2 cell lines have greater (baseline) adhesion properties to HCMEC/D3 cells than the 4L cell line. Next, it was assessed whether manipulation of the levels of B-Met-specific miRNAs would alter the adhesion capacity of the cells. Cells transduced with anti-miR30d (found up-regulated in B-Met) oligonucleotides showed remarkably decreased adhesion to brain endothelial cells, suggesting that the up-regulation of this miRNA in B-Met may provide an advantage to melanoma cells (FIG. 2). Conversely, overexpression of miR-199a-3p (found down-regulated in B-Met) repressed the invasive capacity of melanoma cells (FIGS. 3A-3B). These results encourage further investigating the specific roles of the B-Met-associated miRNAs in mediating the various biological properties that confer increased brain tropism to melanoma cells.

Figure 4A:
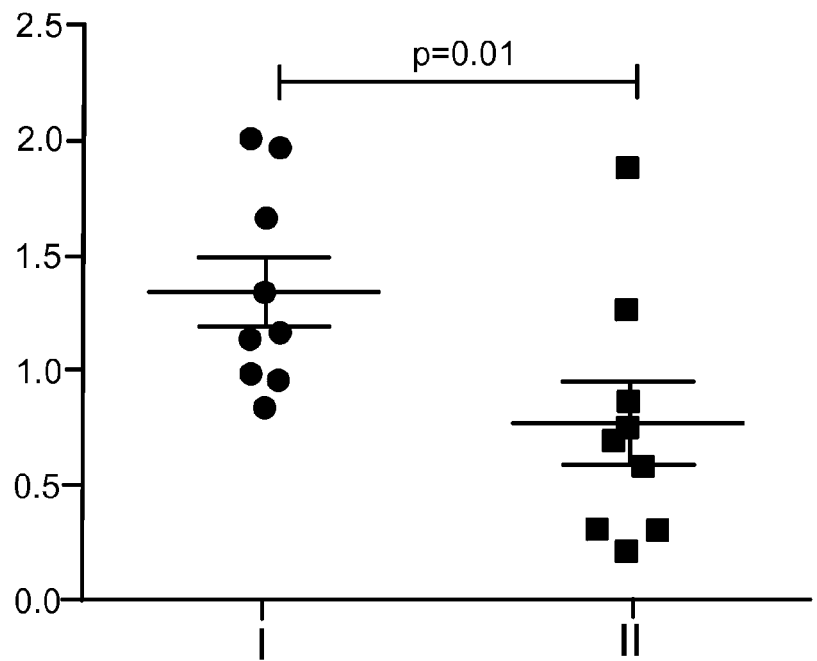
FIGS. 4A-4C demonstrate that repression of miR-199a-3p (SEQ ID NO: 4) accelerates melanoma brain metastasis in a pre-clinical model.
Figure 4B:
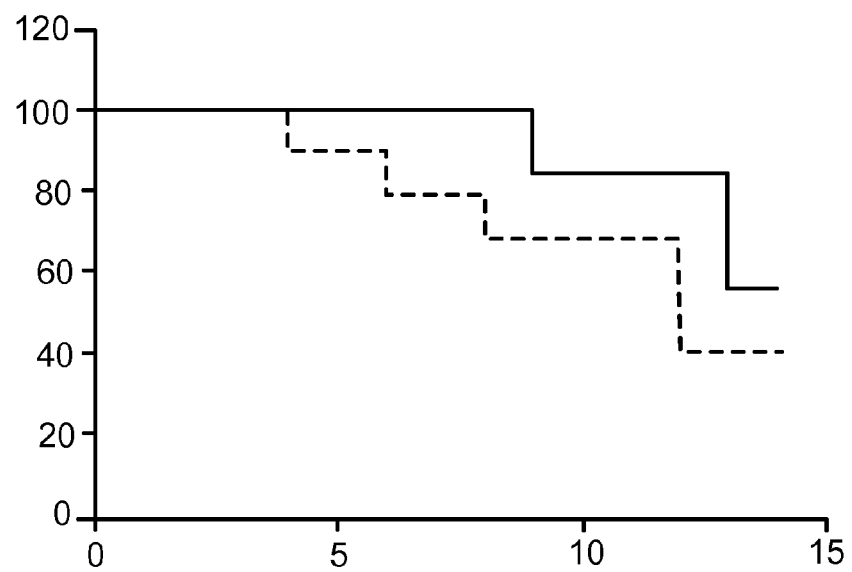
Figure 4C:
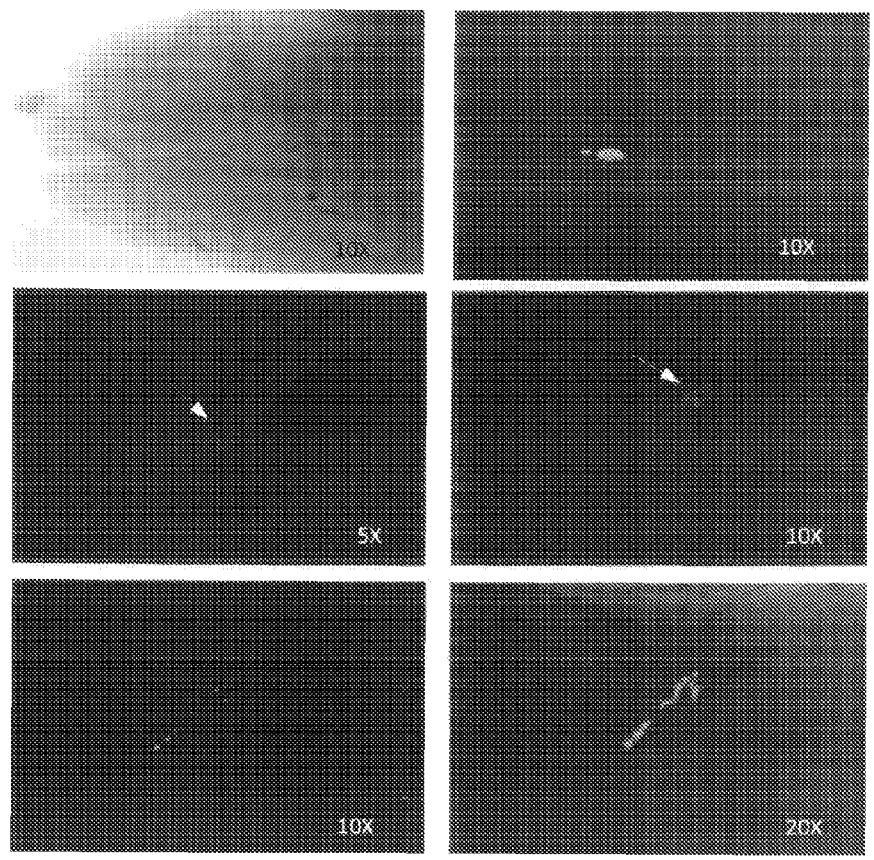

Example 4 miR-199a-3p Silencing Increases the Melanoma Brain Tropism in an In Vivo Preclinical Model 5B1 melanoma cells, a highly metastatic clone with ability to reach the brain was stably transduced with lentivirus miRZIP-199a-3p (containing a sequence complementary to the mature 199a-3p miRNA) or a scramble sequence. Remarkably, low 199a-3p levels were able to accelerate the arrival of melanoma cells to the brain (FIGS. 4A-4C).

Figure 5A:
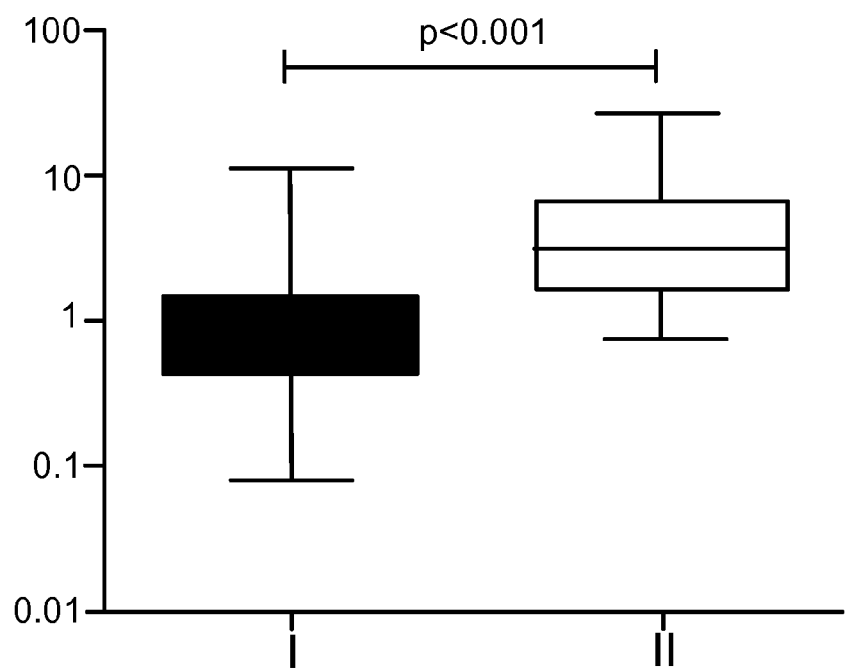
FIGS. 5A-5B demonstrate that miR-30b (SEQ ID NO: 11) is upregulated from primary (I) to metastatic melanoma (II) as detected by qRT-PCR of human samples (n=17) obtained from paired primary-met cases. The Y-axis shows relative expression of miR-30b in log scale.
Figure 5B:
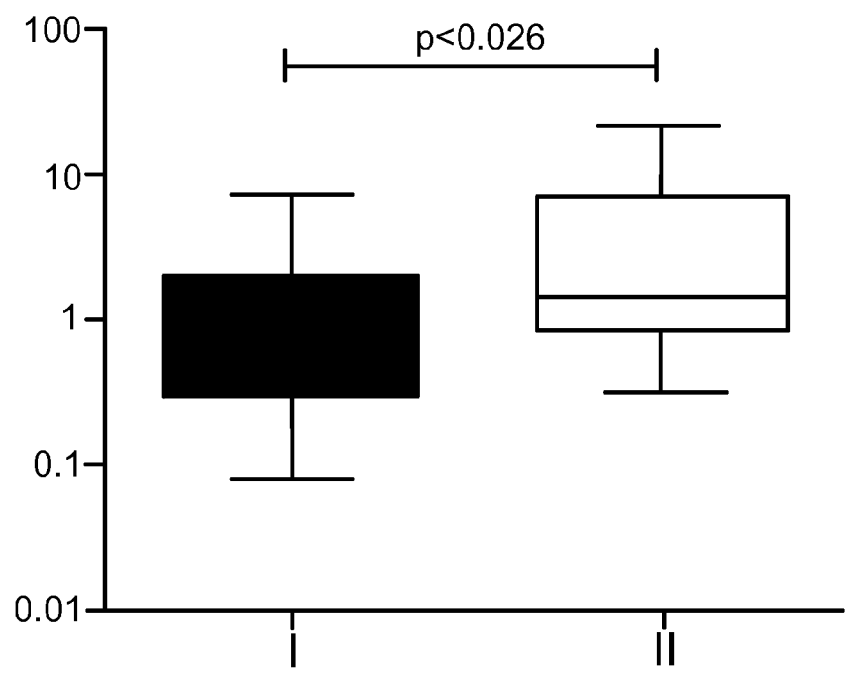
Figure 6A:
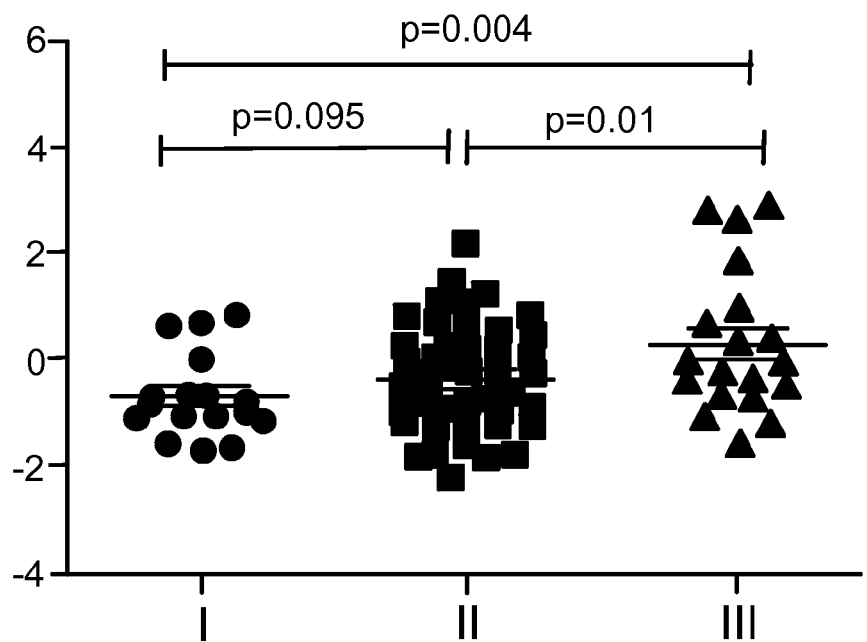
FIG. 6A demonstrates that the relative expression level of miR-30b (SEQ ID NO: 11) (Y-axis), as detected by miRNA array, is increased with the primary melanoma stage at resection (I-III).
Figure 6B:
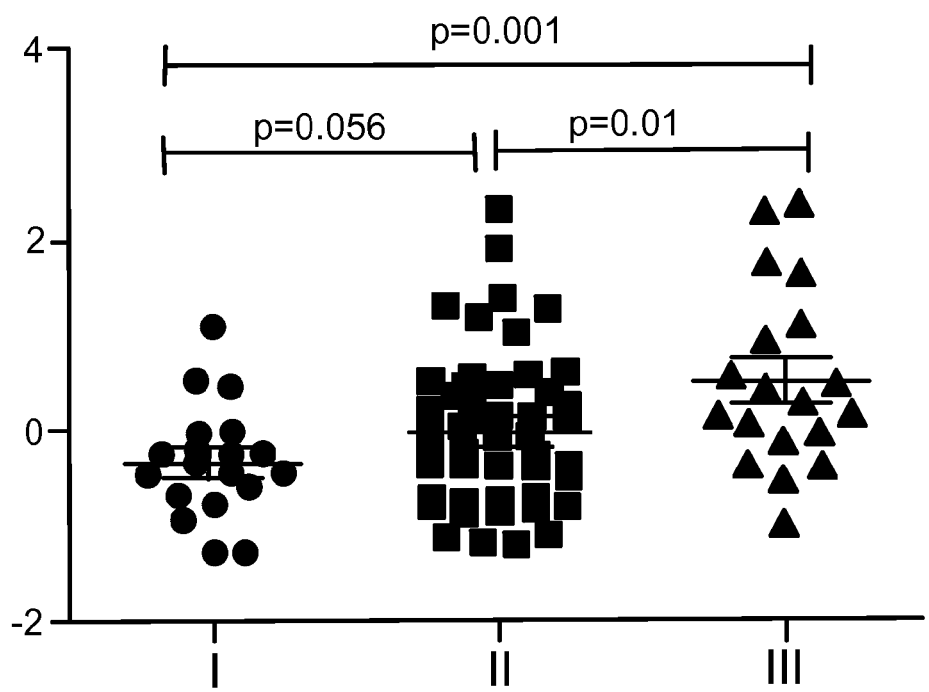
FIG. 6B demonstrates that the relative expression level of miR-30d (SEQ ID NO: 9) (Y-axis), as detected by miRNA array, is increased with the primary melanoma stage at resection (I-III).

Example 5 miR-30b and 30d Levels are Associated with Stage and Increased from Primary to Metastatic Melanoma When comparing miR30b and 30d levels in 17 paired samples (primary and metastatic melanoma from the same patient), a statistically significant increase from primary to the metastatic stage was found (p<0.01 for miR-30b, p=0.026 for miR-30d) (FIGS. 5A-5B). Moreover, a large miRNA profile of primary melanomas (n=93) revealed increased levels of miR-30b and 30d with increasing Stage (I to III) (p=0.004 for miR-30b, p=0.001 for 30d) (FIGS. 6A-6B). These data supports miR-30d/30b upregulation during melanoma progression, irrespective of the site of metastasis.

Figure 7A:
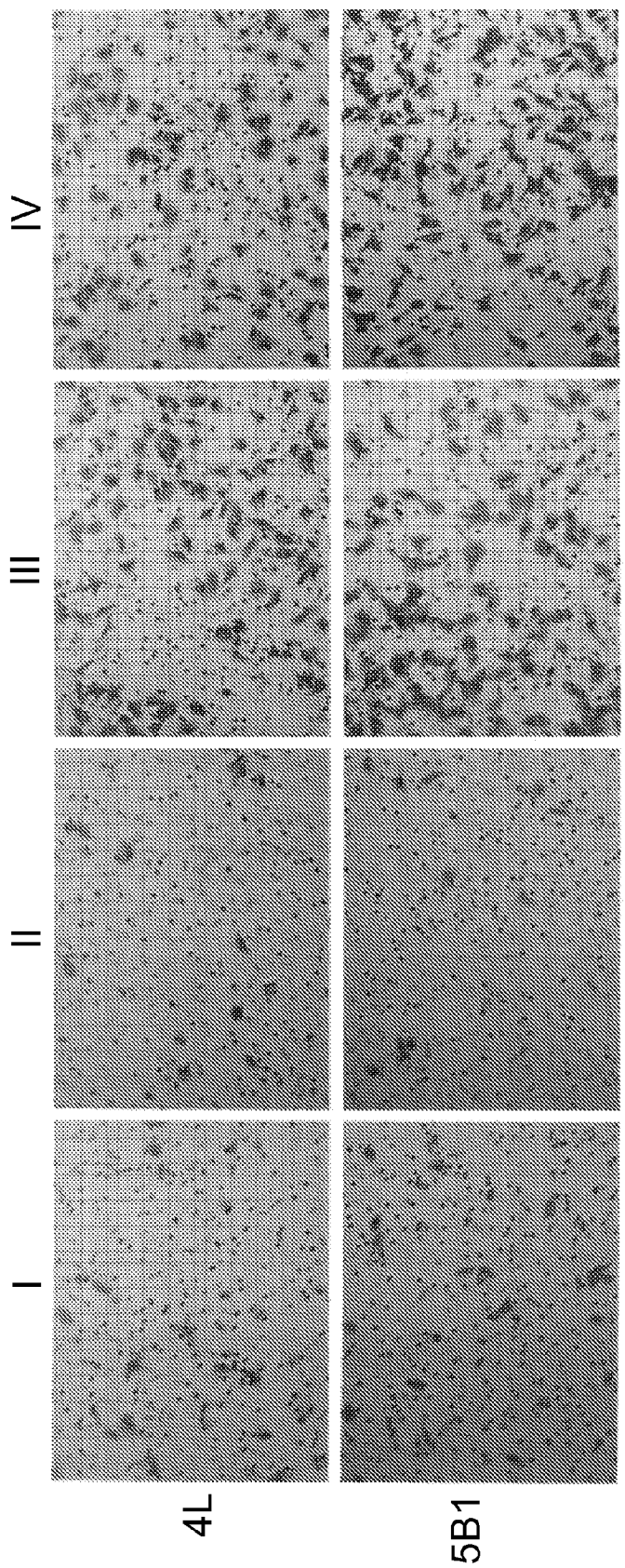
FIG. 7A demonstrates that overexpression of miR-30d (SEQ ID NO: 9, III) and miR-30b (SEQ ID NO: 11, IV) in human melanoma cell lines 113/6-4L and 113/4-5B1 enhance melanoma cell invasion, as compared to cells transduced with a scrambled sequence (I) or with Anti-miR30d (II).
Figure 7B:
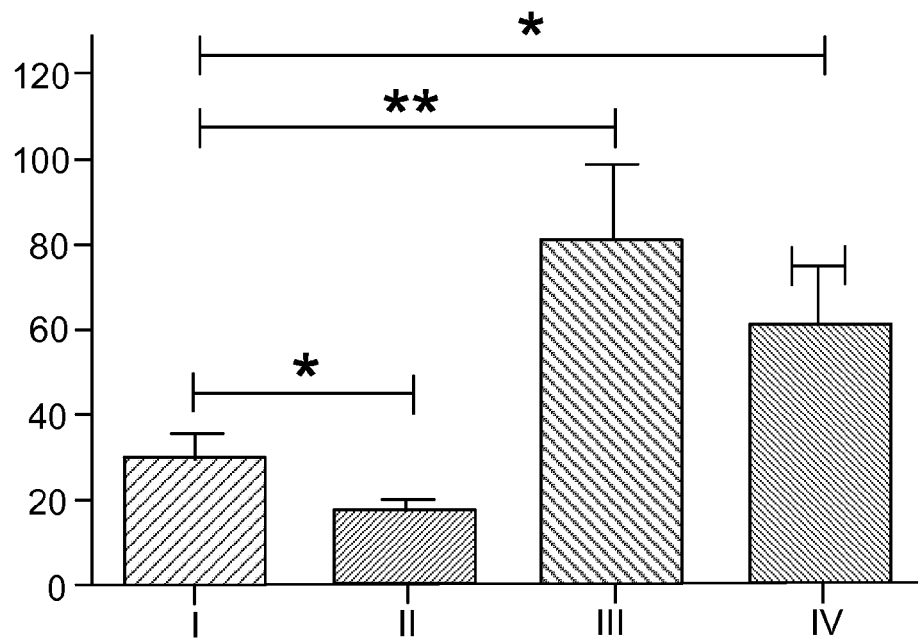
FIG. 7B shows the average number of invasive 113/6-4L cells/field (Y-axis) following transduction with a scrambled sequence (I), Anti-miR-30d (II), miR-30d mimic (III) or miR-30b mimic (IV).
Figure 7C:
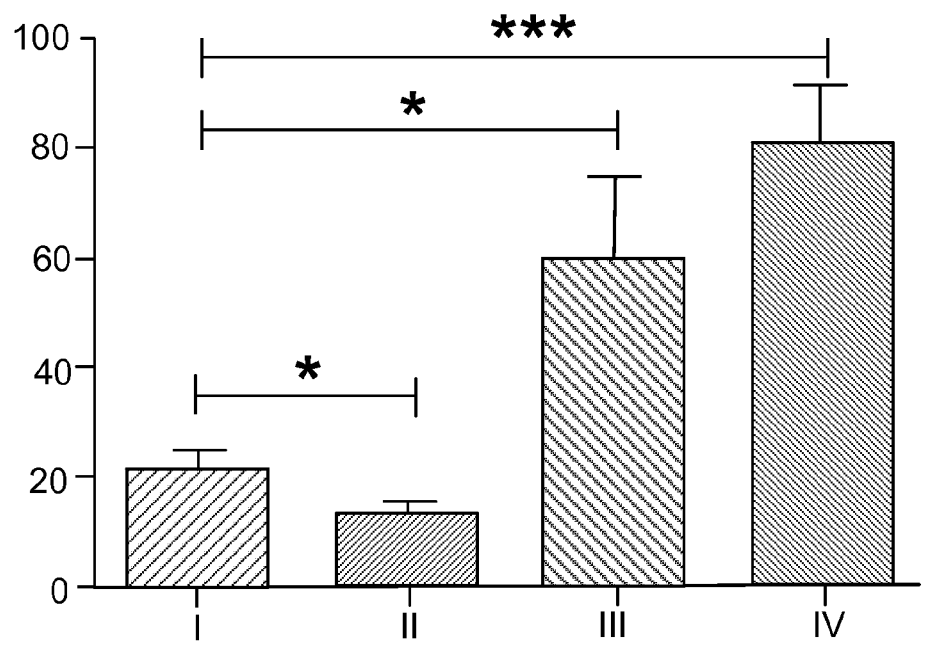
FIG. 7C shows the average number of invasive 113/4-5B1 cells/field (Y-axis) following transduction with a scrambled sequence (I), Anti-miR-30d (II), miR-30d mimic (III) or miR-30b mimic (IV).

Example 6 miR-30b and miR-30d Silencing Impairs the Invasive Potential of Melanoma Cell Lines Whereas their Ectopic Expression Enhances Invasion without Affecting Proliferation Since miR-30b/30d are associated to progression from primary to metastatic melanoma, the effect of miR-30b/30d on the migratory and invasive behavior of melanoma cell lines was further analyzed. Notably, miR-30b and 30d over-expression strongly stimulated the invasive potential of established melanoma cells whereas effective miR-30b and miR-30d silencing suppressed the invasive behavior of 4L and 5B1 cells in fibronectin invasion assays (FIGS. 7A-7C).

To determine whether this augmented invasive behavior could be explained, at least in part, by increased cell proliferation, the growth rates of miR-30b/30d and vector-transduced cells were compared. No statistically significant differences were found by means of trypan-blue exclusion, crystal violet staining or WST-1 proliferation assays (data not shown). It was concluded that miR-30b/30d expression confers on melanoma cells the ability, necessary for metastasis, to move through an extracellular matrix.

Next, since miR-30b and miR-30d are co-expressed from the same cluster, we tested the effect of inducing both simultaneously. Neither additive nor synergistic effects were detected in the Boyden chamber assay (FIG. 12A), indicating that the two miRNAs have redundant pro-invasive functions. This is not surprising, since they share the same seed region and thus likely operate through common targets.

Figure 8A:
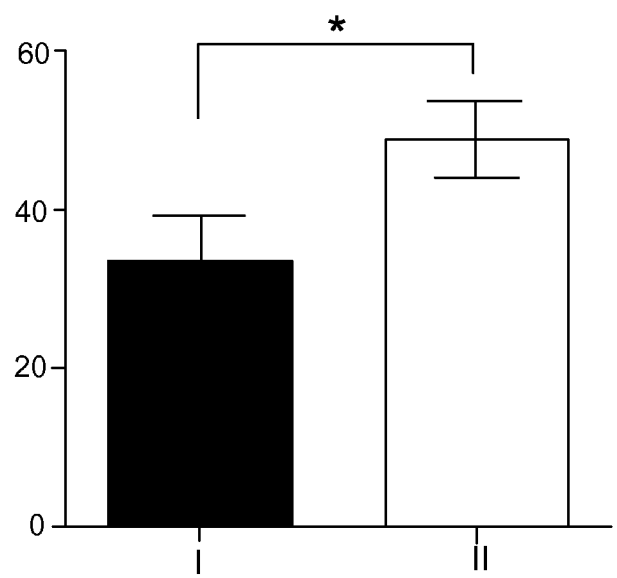
FIG. 8A demonstrates the number of macrometastasis in mice after tail vein injection of 1E05 B16F10 cells transiently transduced with scramble oligonucleotides (I) or miR-30d mimic oligonucleotides (SEQ ID NO: 9, II). The Y-axis shows the average number of metastasis/filed.
Figure 8B:
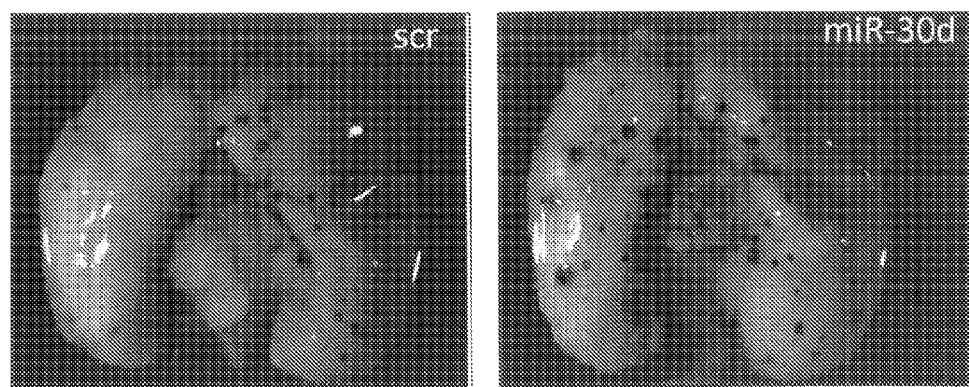
FIG. 8B shows representative pictures of whole lungs of mice injected with B16F10/scramble (scr) or B16F10/mimic miR30d oligonucleotides.
Figure 8C:
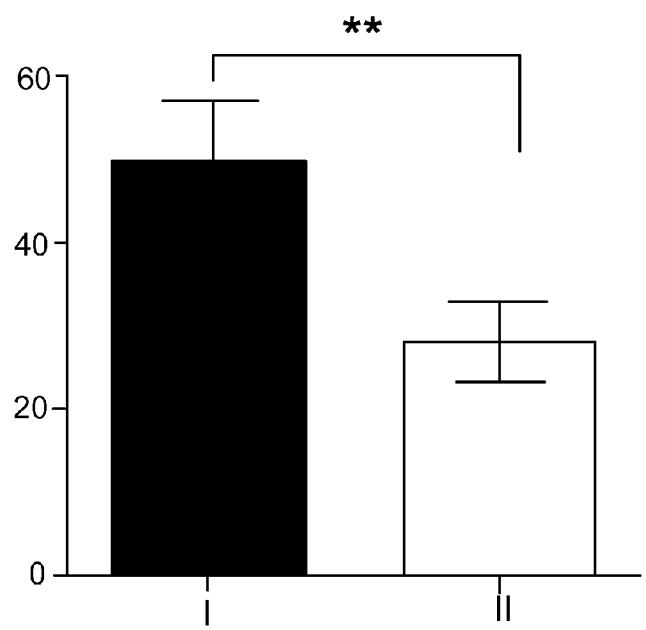
FIG. 8C demonstrates the number of macrometastasis in mice after tail vein injection of B16F10 cells transiently transduced with scramble oligonucleotides (I) or anti-miR-30d oligonucleotides (II). The Y-axis shows the average number of metastasis/filed.
Figure 8D:
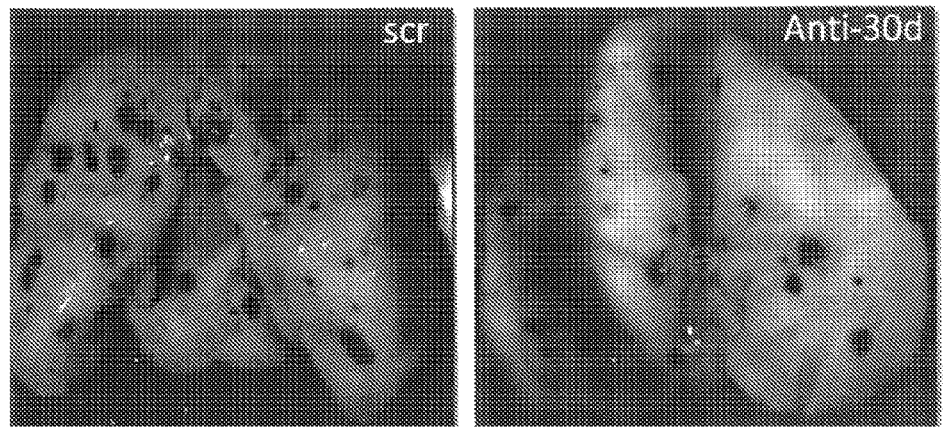
FIG. 8D shows representative pictures of whole lungs of mice injected with B16F10/scramble or B16F10/anti-miR30d oligonucleotides.
Figure 9A:
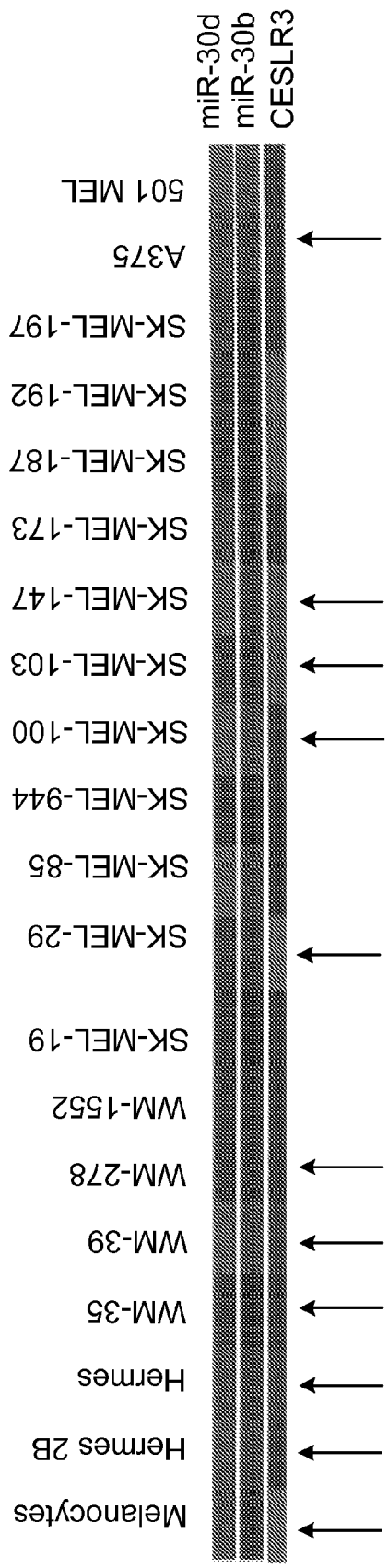
FIG. 9A is a heatmap representation of the relative levels of miR-30b/30d and its target CESLR3 (mammalian transmembrane cadherin) in a panel of melanoma cell lines, obtained by array analyses.
Figure 9B:
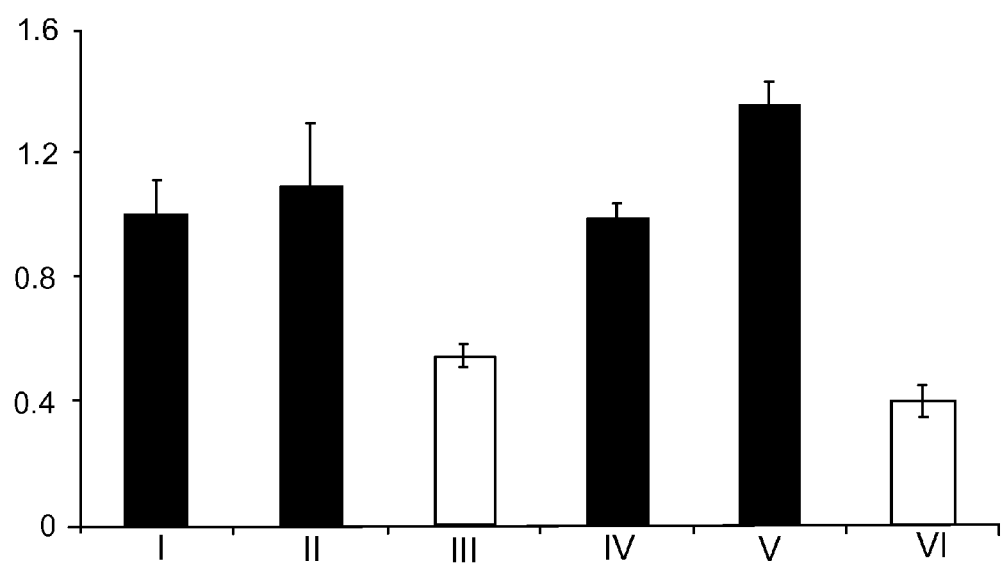
FIG. 9B shows the relative mRNA expression of CESLR3 (Y-axis) in 113/4-5B1 cells following transient transduction with a scrambled sequence (I), Anti-miR-30d (II), miR-30d mimic (III), or in 113/6-4L cells following transduction with a scrambled sequence (IV), Anti-miR-30d (V) and miR-30d mimic (VI) as measured by real time PCR.
Figure 10A:
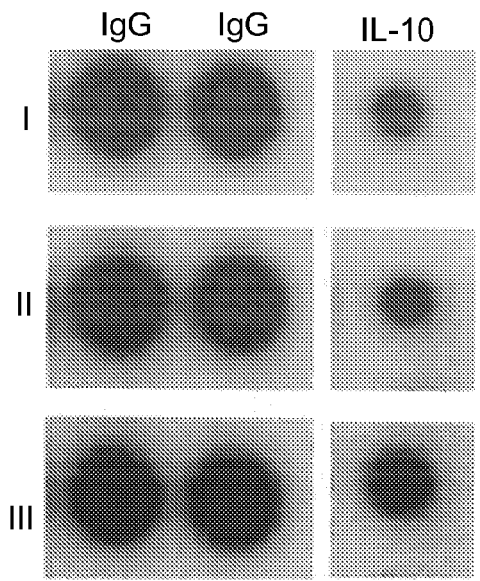
FIGS. 10A-10D demonstrate that overexpression of miR-30d enhances IL10 secretion. Cytokine antibody arrays (Raybiotech) were probed with conditioned media of 113/6-4L (FIGS. 10A-10B) and 113/4-5B1 (FIG. 10C-10D) cells transduced with scramble (I, black column), miR-30d mimic (III, white column) or anti-miR-30 (II, grey column) oligonucleotides. IL-10 and IgG relative signal density was quantified using ImageJ software. The Y-axis shows the relative signal density (FIGS. 10B,10D).
Figure 10B:
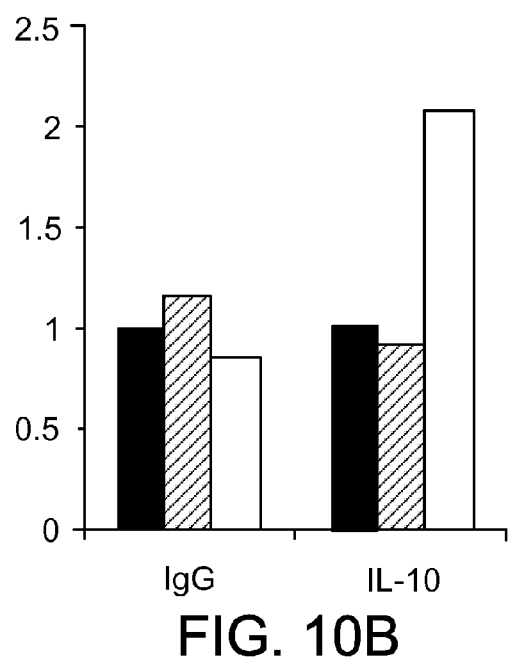
Figure 10C:
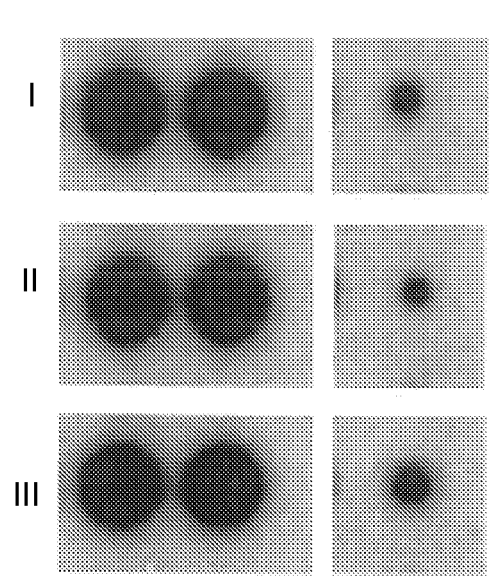
Figure 10D:
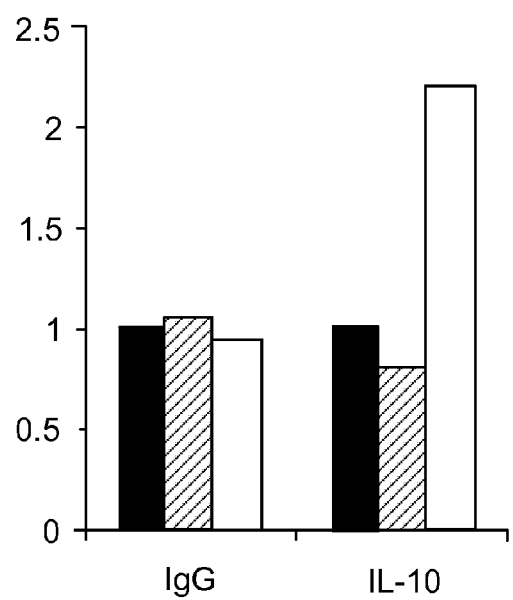

Example 7 miR-30d Overexpression Enhances In Vivo Metastasis Whereas miR-30d Silencing Represses the Metastatic Potential of Melanoma Cells The influence of miR-30d downregulation in a classic in vivo model of melanoma lung metastasis: B16F10 mouse melanoma cells, was studied. B16F10 cells were transiently transduced with scramble or anti-miR-30d oligonucleotides and injected them into the tail veins of 6-week old immunocompetent mice. Ten days post-injection the mice were sacrificed and dissected the lungs for macro- and microscopic histology. Lungs of B16F10-anti-miR-30d injected mice harbored half the number of macroscopic metastases (FIGS. 8C, 8D), demonstrating that miR-30d augments the ability of melanoma cells to extravasate and/or seed at a distant site (P<0.01). Conversely, B16F10 cells transiently transduced with miR-30d mimic oligo induced more and larger metastatic foci after tail vein injection of B16 transduced with scramble oligo (p<0.01) (FIGS. 8A, 8B).

Example 8 miR-30d levels modulate the expression of chemokines and chemokine receptors.

In order to define potential downstream mediators of the miRNA's ability to enhance melanoma brain tropism, the effect of their modulation in the expression of chemokines and their receptors was evaluated using PCR Arrays (SA Biosciences). These analyses revealed that miR-30d silencing results in altered mRNA expression of several chemokines (CCL5, CXCL2) and chemokine receptors (CCR5, CCRL1). Moreover, the use of human cytokine antibody arrays (RayBio) confirmed that melanoma cells transduced with miR-30d mimics secrete higher levels of inflammatory and chemotactic mediators (IL10) (FIGS. 10A-10D). The immunosuppressive effects of IL-10 might promote melanoma spread.

CESLR3 Levels are Modulated by miR-30d Expression.

4L and 5B1 cells transduced with anti-miR-30d oligonucleotides express slightly higher levels of CESLR3 compared to scramble-transfected cells, as measured by quantitative RT-PCR. Conversely, CESLR3 levels in 4L and 5B1 cells transduced with miR-30d mimics are significantly lower than in the corresponding scramble transduced cells.

Example 9 miR-451 Overexpression in Primary Melanoma Associates with the Capacity to Develop Brain Metastasis A miRNA array profile of 93 primary melanomas (n=49 non metastatic, n=44 metastatic of which n=24 develop brain metastasis) has been conducted using Exiqon arrays. This analysis revealed that miR-451 overexpression correlates with the ability to develop brain metastasis even at the primary stage (p=0.03). These findings offer the possibility of identifying patients at higher risk of developing B-Met at the time of diagnosis.

Example 10

Figure 11A:
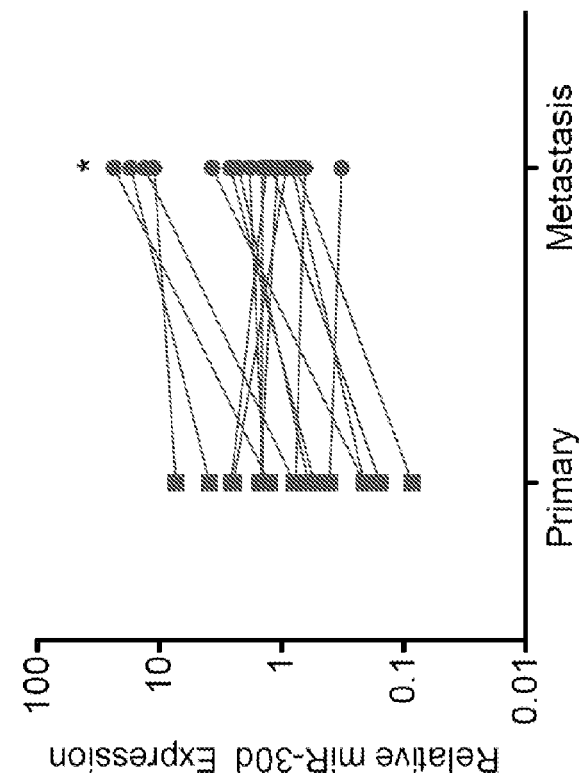
FIGS. 11A-11F miR-30b and miR-30d overexpression is associated with metastatic behavior in melanoma, shorter time to recurrence, and lower overall survival. 11A. Increased relative levels of miR-30b and miR-30d in 17 metastatic cases compared to the levels in their matched primary tumors, as measured by quantitative RT-PCR. 11B-11C. MiR-30b and miR-30d normalized array levels in 92 primary cases with (11B) increased thickness and (11C) increased stage. ANOVA test was applied in B. 11D. MiR-30b and miR-30d normalized array levels were significantly lower in superficial spreading melanomas (SSM; n=28) than in nodular melanoma (NM; n=56). 11E-11F. Graphs show shorter time to recurrence (11E) and lower overall survival (F; n=92) in patients with high (above median value) as opposed to low (below median value) miR-30b/30d levels. (*p<0.05; p<0.01; *p<0.001).
Figure 11A:
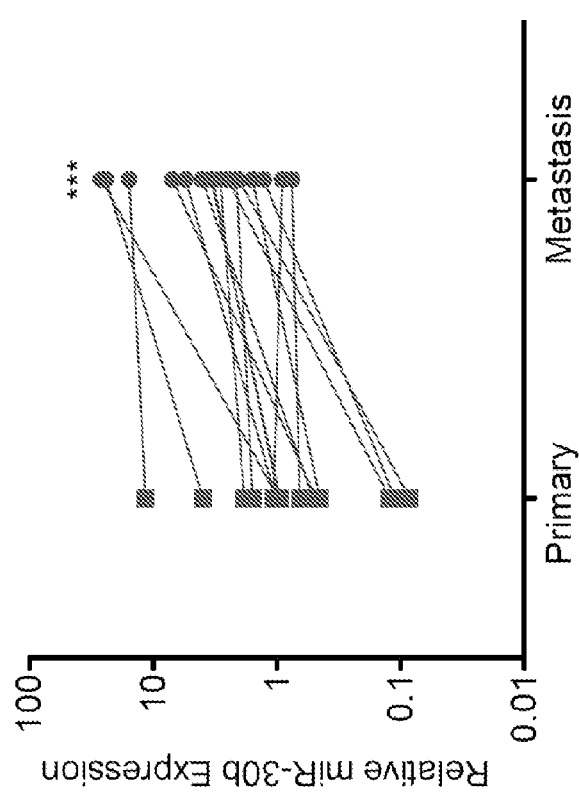
Figure 11B:
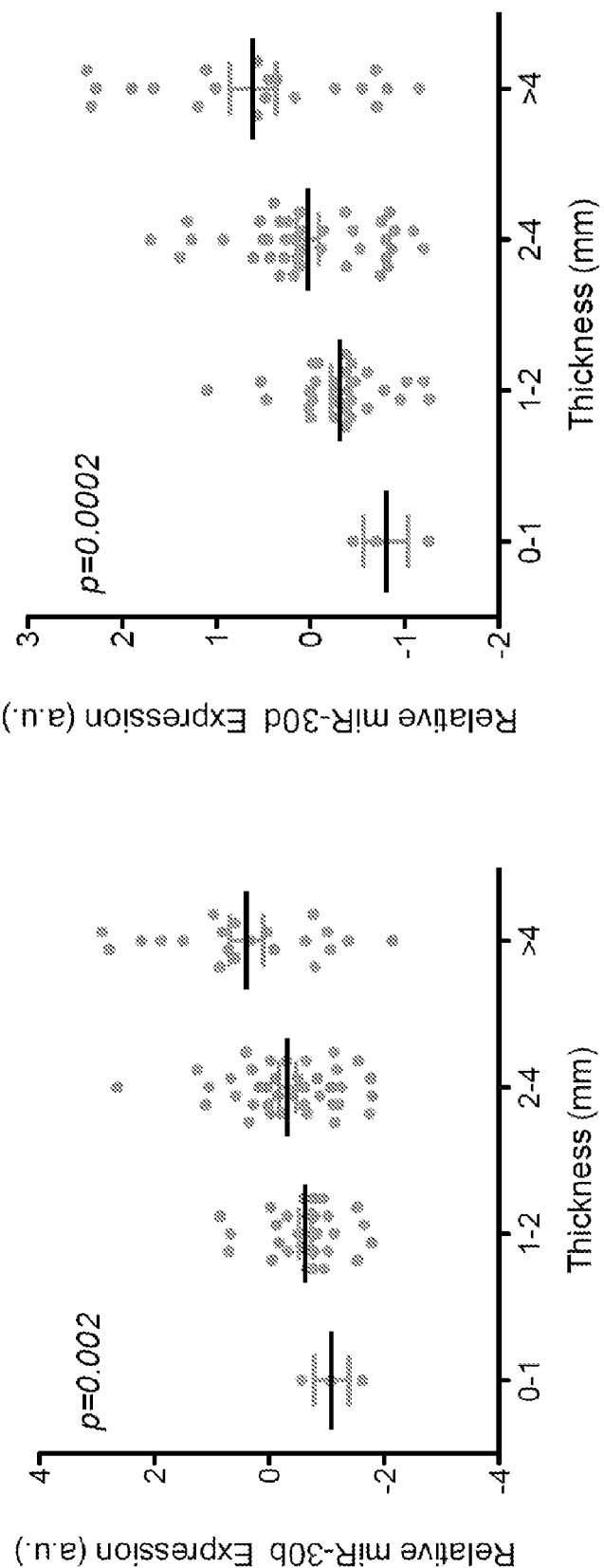
Figure 11C:
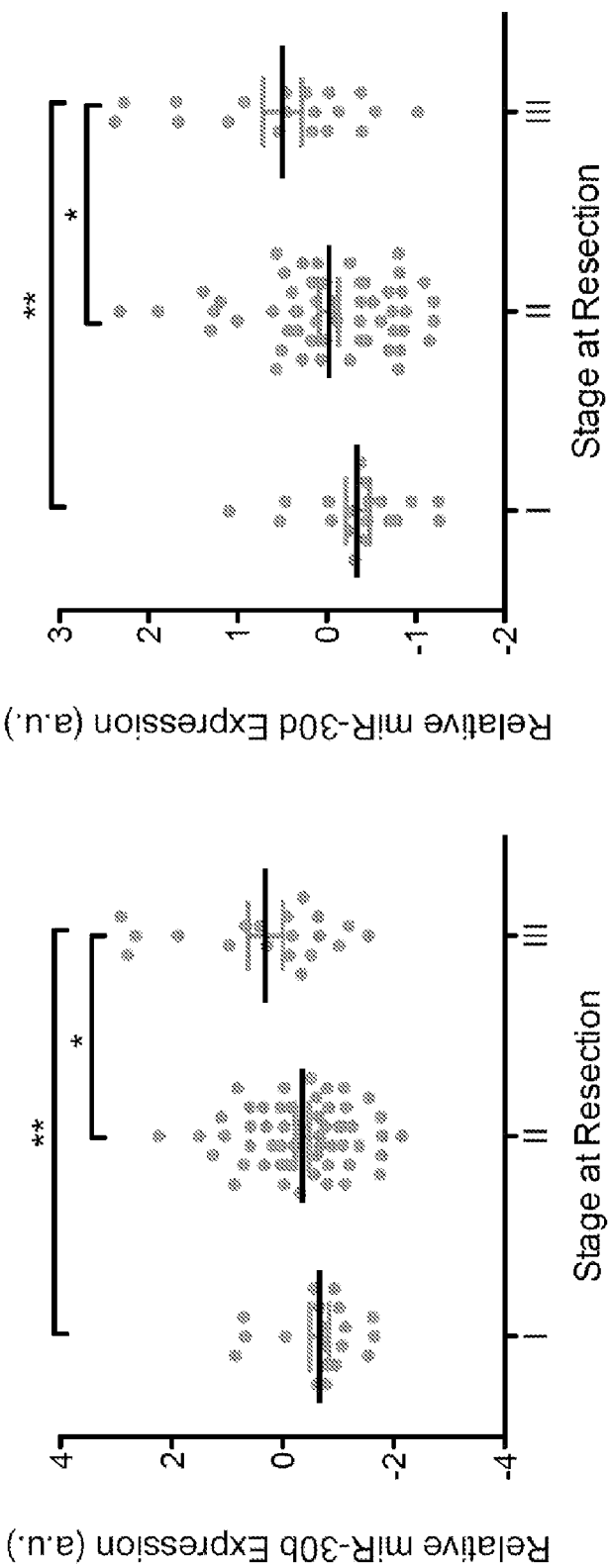
Figure 11D:
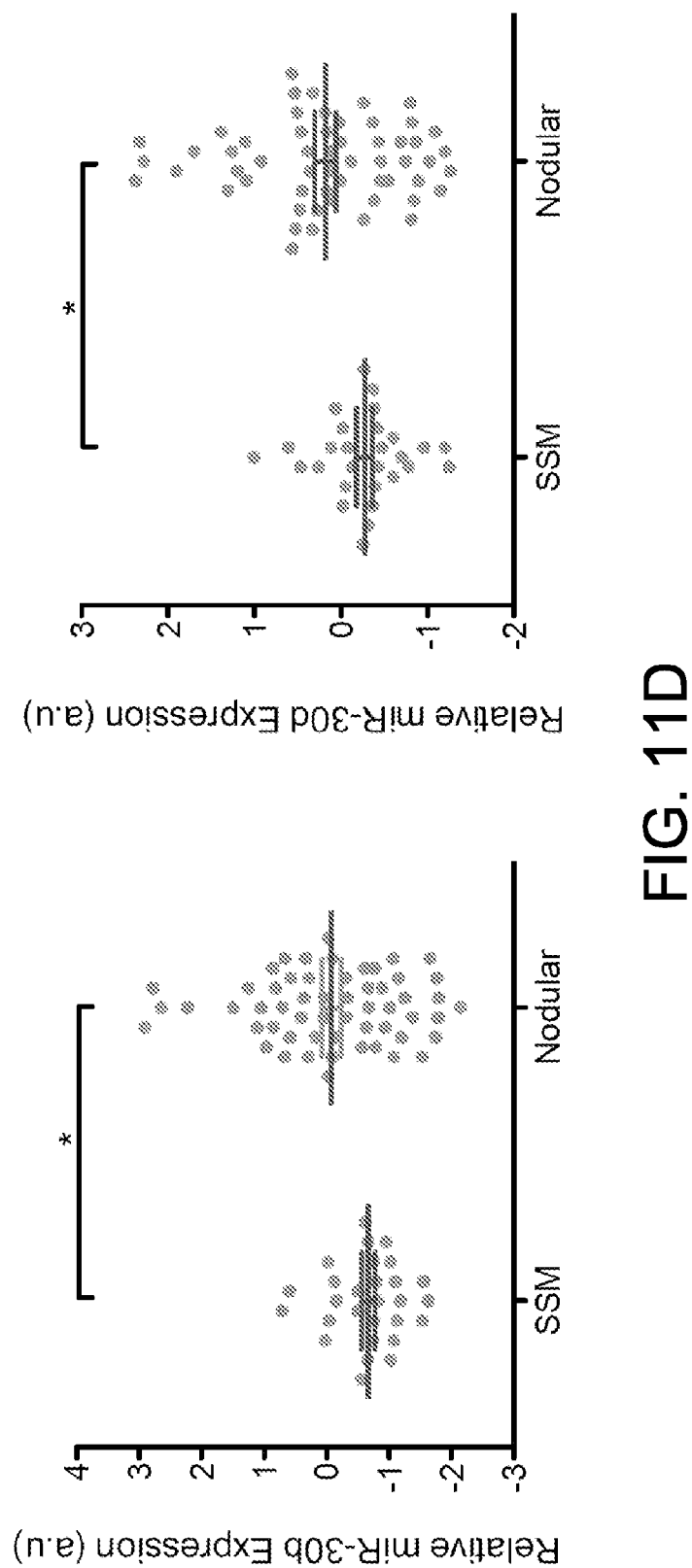
Figure 11E:
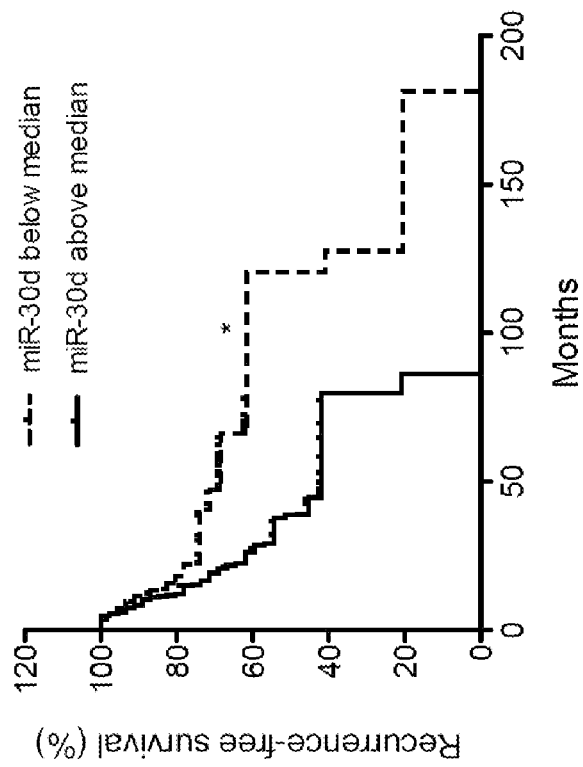
Figure 11E:
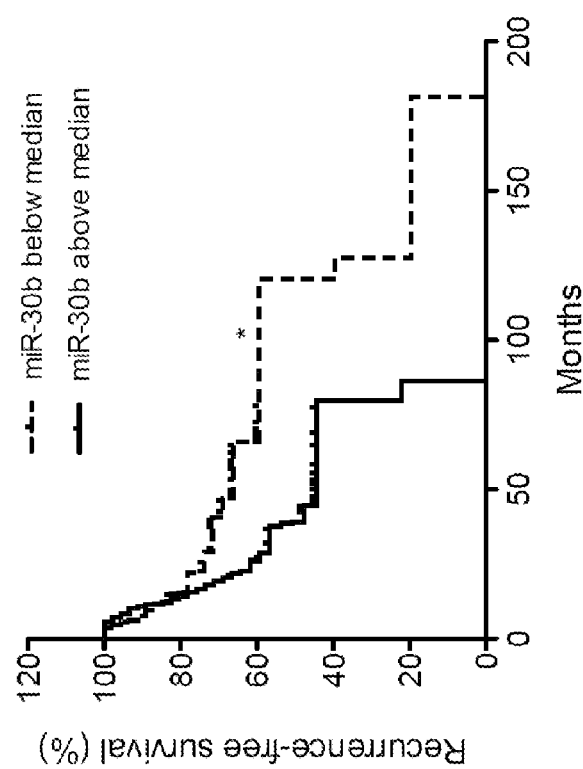
Figure 11F:
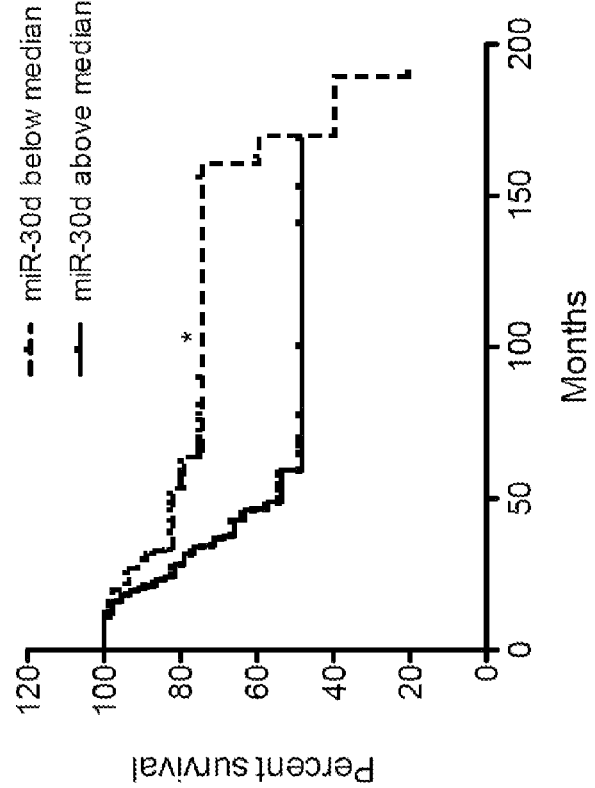
Figure 11F:
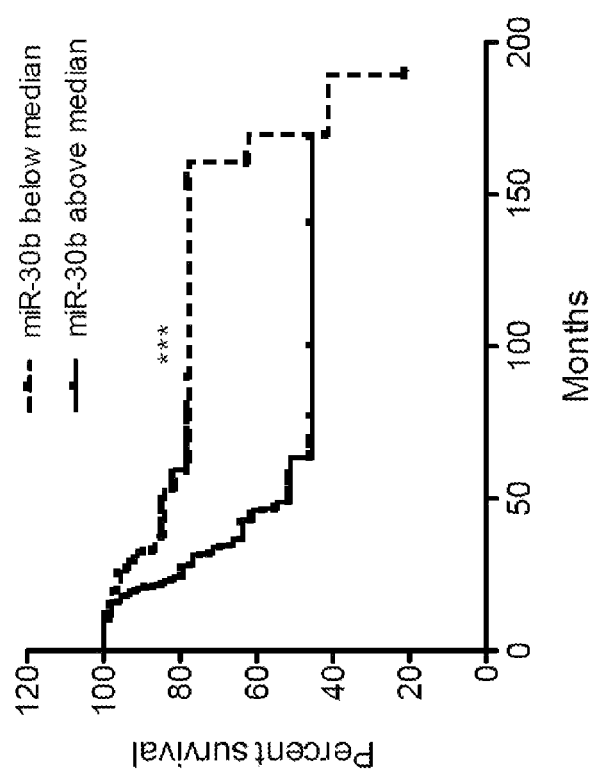

Expression of miR-30b and 30d in Human Melanoma Marks the Progression from Primary to Metastatic Tumors MiRNA array analysis of 59 metastatic melanoma tumor samples (Segura et al., 2010), followed by quantitative RT-PCR validation, revealed high expression levels of miR-30b and -30d. These two miRNAs form a cluster on 8q24, a common amplicon in melanoma (Ehlers et al., 2005). In a subset of 17 paired samples (primary tumor and a metastasis from the same patient), we found a statistically significant increase in expression of these miRNAs from the primary to the metastatic stage (p=0.0007 for miR-30b, p=0.026 for miR-30d) (FIG. 11A). A miRNA profile of primary melanomas (n=92) revealed that higher levels of miR-30b and -30d corresponded with increased tumor thickness (p=0.002 for miR-30b, p=0.0002 for 30d; FIG. 11B) and advancing stage (I to III) (p=0.004 for miR-30b, p=0.001 for 30d; FIG. 11C), suggesting an association between miR-30b/d expression and tumor progression. By histological subtype, the more invasive nodular melanomas (NM) had higher miR-30b/30d levels than superficial spreading melanomas (SSM) (p=0.015 for miR-30b, p=0.0189 for 30d FIG. 11D). Furthermore, the subgroup of primary melanomas that had metastasized (n=44) showed higher levels of miR-30b and -30d expression than those that had not spread (n=48) during a period of 24 months or more of follow-up (p=0.048 for miR-30b, p=0.037 for miR-30d; data not shown). Accordingly, miR-30b and miR-30d levels above the median correlated with shorter time to recurrence (p=0.04 for miR-30b and p=0.01 for miR-30d FIG. 11E) and lower overall survival of melanoma patients (with p=0.0004 for miR-30b and p=0.02 for miR-30d; FIG. 11F). Multivariate analysis using COX PH models indicated that the expression level of miR-30d is a statistically significant independent predictor for melanoma mortality (p=0.004) when adjusted for primary tumor thickness and ulceration status. The expression level of miR-30b is only marginally significant as an independent predictor for death with melanoma when adjusted for primary tumor thickness and ulceration (p=0.054). These data support an association between miR-30b/30d upregulation and increased melanoma aggressiveness, and suggest a potential use of these miRNAs as prognostic biomarkers.

Example 11

MiR-30b/30d Overexpression Correlates with Genomic Amplification in a Subset of Human Melanomasamples The miR-30b/30d cluster (8q24.22-8q24.23) is located in the vicinity of a genomic region containing the oncogene c-MYC (8q24.21), which is frequently amplified in multiple cancer types, including medulloblastoma (Lu et al., 2009); uveal melanoma (Ehlers et al., 2005); head, neck and cervical squamous cell carcinomas; bladder (Visapaa et al., 2003), lung and prostate cancer (Van DenBerg et al., 1995). c-MYC amplification is usually associated with tumor progression.

We found the miR-30b/30d genomic region amplified in 12 out of 33 metastatic melanoma tissues (36.4% of cases)), of which approximately half harbored concomitant c-MYC gene copy gains, suggesting that the miR-30b/30d gains are generally independent of c-MYC amplification. Interestingly, we noted a higher fraction of patients carrying the miR-30b/30d amplification died within the study period (data notshown), suggesting this genetic trait is associated with more aggressive disease.

Example 12

Figure 12A:
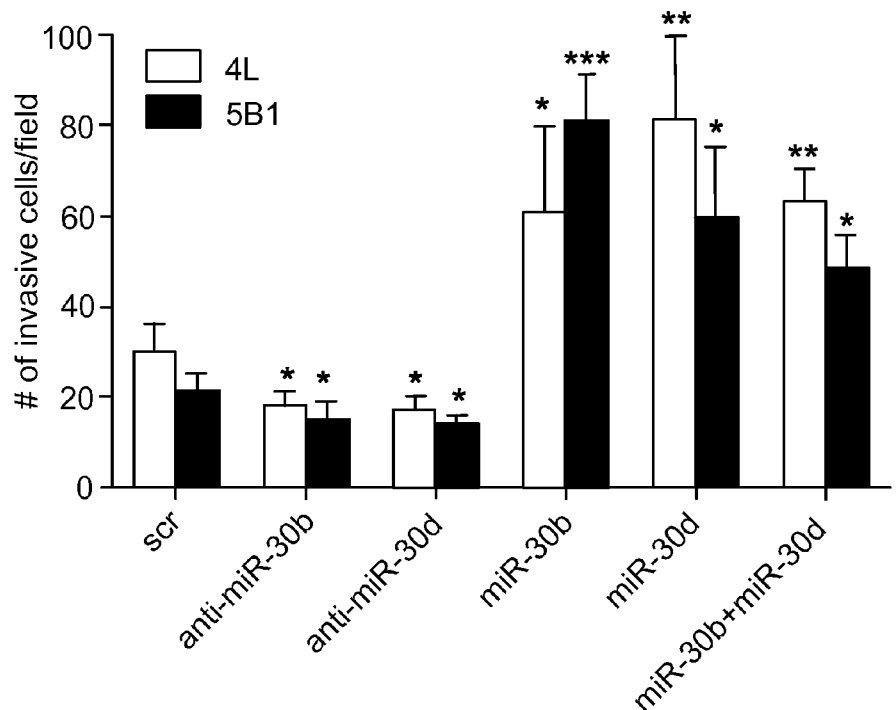
FIGS. 12A-12H. MiR-30b and miR-30d promote melanoma invasion and metastasis in vitro and in vivo. 12A. Transwell invasion assay of indicated cell lines with miR-30b, -30d, or both, either silenced or overexpressed (mean±SEM). scr=scrambled control. 12B-12C. In vivo metastasis assay with B16F10 mouse melanoma cells transiently transfected with scr, anti-miR-30d or miR-30d mimics injected through the lateral tail vein of C57BL/6J mice (n=10 per group). Histogram in (12B) shows that anti-miR-30d suppressed metastasis, while miR-30d increased metastatic behavior (12C). Right: macroscopic pictures of mouse lungs and H&E-stained sections of lung metastases at termination of the experiment. Scale bars represent 100 µm. Black dotted circles mark metastatic foci. 12D. Transwell invasion assay with 2 primary melanoma cell lines WM98 and WM35 transduced with scrambled control or miR-30d. 12E. In vivo metastasis assay with WM98 melanoma cells stably transduced with GIPZ-scr or GIPZ-miR-30d injected through the lateral tail vein of NOG/SCID mice (n=14 for scr and n=17 for miR-30d). Histogram show the percentage of mice that developed lung metastases in each cohort. Whisker plots show the distribution of the number of metastases per section. Representative micrographies of H&E-stained sections of lungs are shown. Scale bars represent 100 µm. Black dotted circles mark metastatic foci. 12F-12H. Pre-clinical model of human melanoma metastasis. 5B1 cells stably transduced with either scr (n=19) or miR-30d (n=19) vectors, were injected subcutaneously into the flanks of NOG/SCID mice, and tumors and organs collected 80 days post inoculation. 12F. H&E-stained sections show increased local invasion of miR-30d-transduced tumors (scale bar represents 100 µm). Histogram represents the percentage of mice in each cohort with primary tumors that invaded grossly into the leg. 12G-12H. Representative micrographies of H&E-stained sections of lungs (12G) or livers (12H) show increased number and size of metastases in the miR-30d cohort. Scale bars represent 100 µm. Histograms show the percentage of mice that developed lung or liver metastases in each cohort. Whisker plots show the distribution of the number or size (largest in each section) of metastasis per section. Bars represent the median value (*p<0.05; p<0.01; *p<0.001).

MiR-30b or miR-30d Modulation Alters the Invasive Potential of Melanoma Cells Without Affecting Cell Proliferation Since upregulation of miR-30b and 30d is associated with progression from primary to metastatic melanoma, we asked whether these miRNAs enhance the invasive behavior of melanoma cells. Using a fibronectin transwell invasion assay, we found that ectopic expression of miR-30b and 30d (FIG. 12A) strongly stimulated the invasive capacity of two metastatic melanoma cell lines, 113/6-4L (hereafter, 4L) and 131/4-5B1 (hereafter 5B1) (Cruz-Munoz et al., 2008) (FIG. 12A; p=0.037 and p=0.0002 for miR-30b and p=0.009 and p=0.011 for miR-30d in 4L and 5B1, respectively). In contrast, silencing of miR-30b or miR-30d by antisense oligonucleotide (anti-miR) transfection (FIG. 12A) suppressed cell migration (p=0.026 and p=0.032 for miR-30b; p=0.041 and p=0.044 for miR-30d in 4L and 5B1 respectively; FIG. 12A).

To determine whether the increase in invasive behavior could be explained, at least in part, by increased cell proliferation, we compared the growth rates of cells transduced with miR-30b or miR-30d or scrambled control. We found no statistically significant differences by means of trypan-blue exclusion or crystal violet staining (data not shown). Therefore, we conclude that miR-30b/30d increase melanoma cells' capacity to migrate through the extracellular matrix, an essential ability for metastasis.

Next, since miR-30b and miR-30d are co-expressed from the same cluster, we tested the effect of inducing both simultaneously. Neither additive nor synergistic effects were detected in the Boyden chamber assay (FIG. 12A), indicating that the two miRNAs have redundant pro-invasive functions. This is not surprising, since they share the same seed region and thus likely operate through common targets.

Figure 12B:
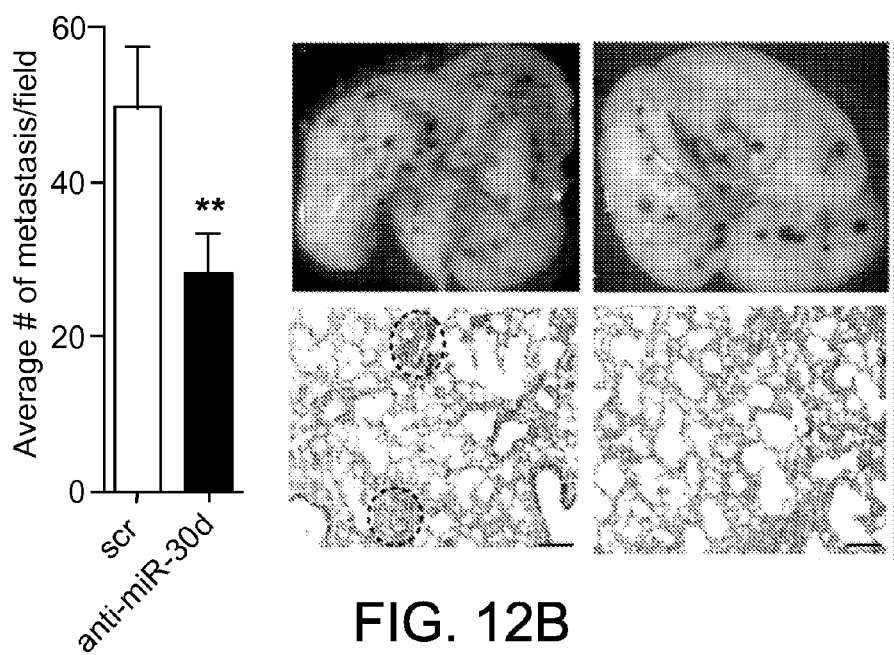
Figure 12C:
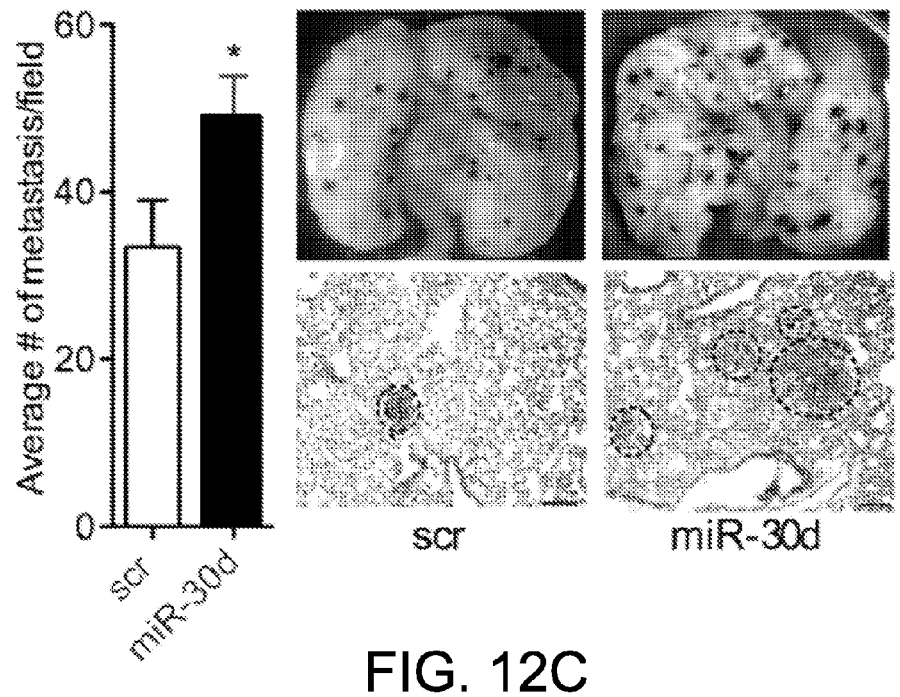
Figure 13A:
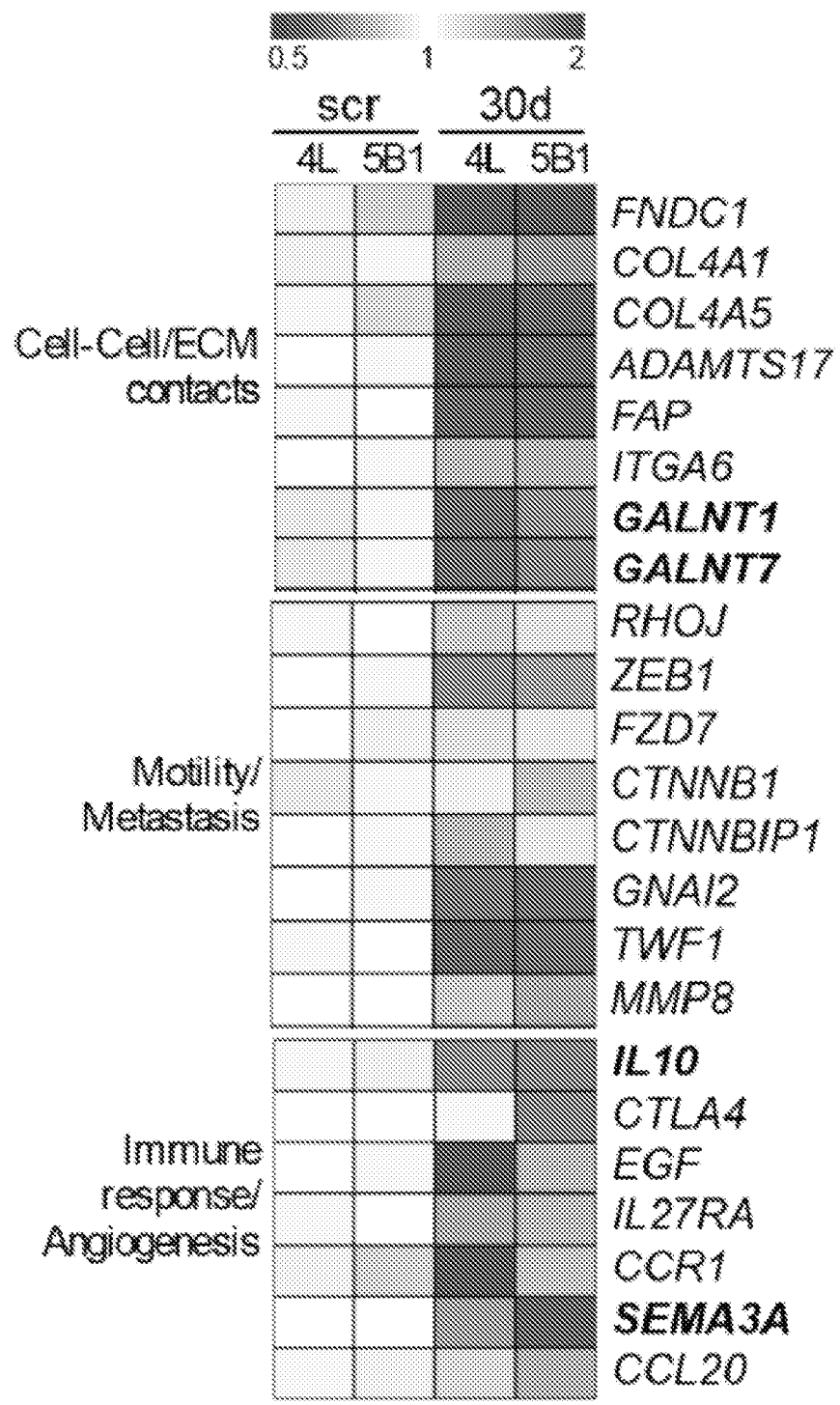
Figure 13B:
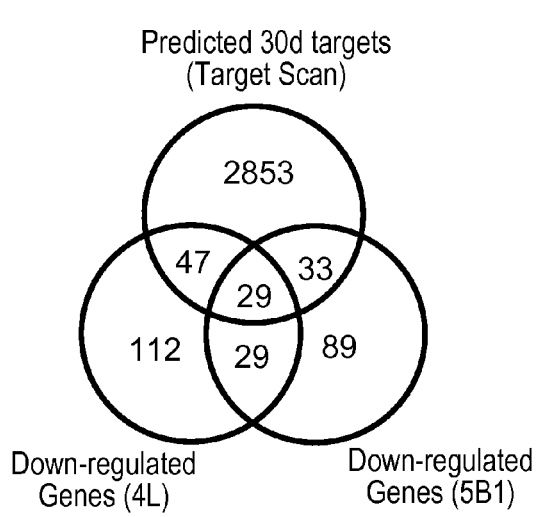
Figure 13C:
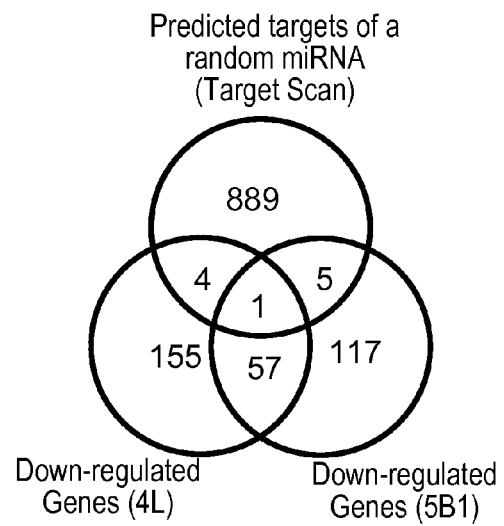

MiR-30d Overexpression Enhances Metastasis, Whereas its Silencing Represses Metastasis In Vivo Our in vitro results led us to study the impact of miR-30d downregulation in a classic in vivo model of lung metastasis: We transiently transduced B16F10 mouse melanoma cells in vitro with scrambled or anti-miR-30d oligonucleotide. (FIG. 12B) and injected them into the tail veins of immunocompetent mice 8 to 12 weeks of age. Eleven days post-injection we sacrificed the mice and dissected the lungs for macro- and microscopic histology. Lungs of B16F10/anti-miR-30d injected mice harbored significantly fewer micro- and macroscopic metastases than scramble control (p=0.0085; FIG. 12B). Conversely, mice injected with B16F10 cells transiently transduced with miR-30d mimic oligonucleotides generated more metastatic foci than control cells transfected with scrambled oligonucleotide (p=0.0218; FIG. 12C). Then, we compared the metastatic potential of B16 transiently transfected with miR-30b, miR-30d or combinations of miR-30b and 30d mimic oligonucleotides injected through the tail vein. MiR-30d and miR-30b had similar pro-metastatic effects and the combination of the two showed only a slight increase over miR-30d alone (FIG. 13A-C). Therefore, both our in vitro and in vivo results indicate that miR-30b and miR-30d have redundant effects on invasion and metastasis. Given this functional redundancy, we focused primarily on miR-30d in the following experiments.

Figure 12D:
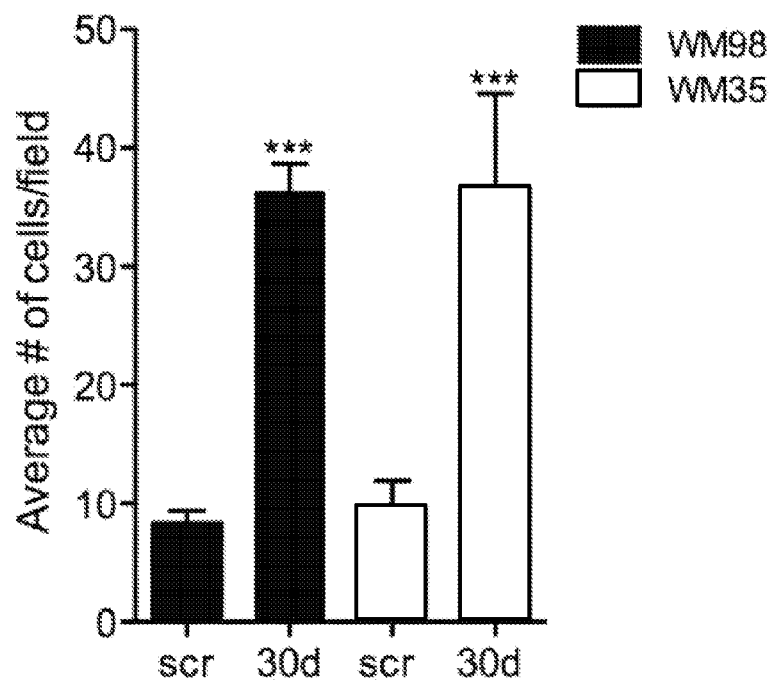
Figure 12E:
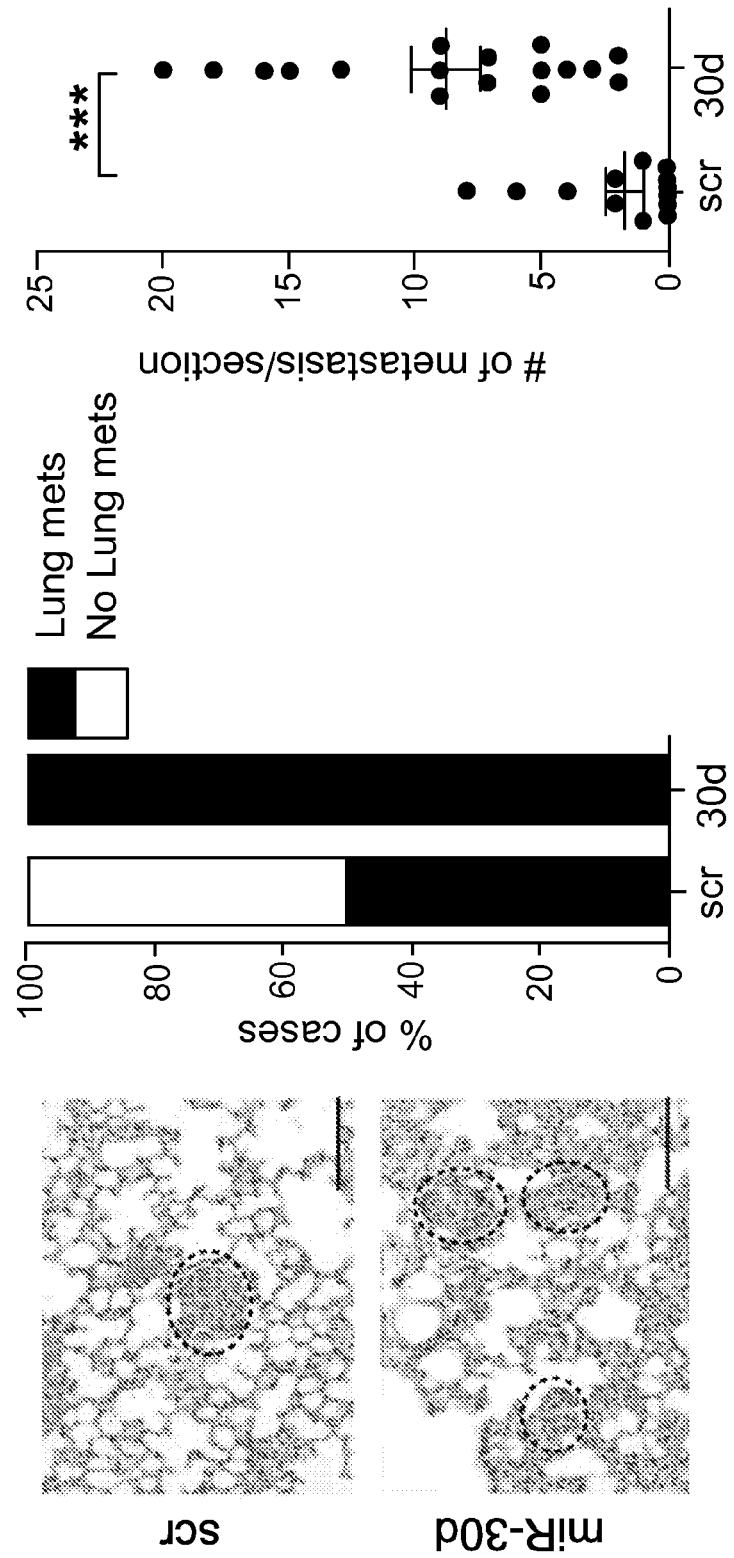

We asked whether miR-30d could confer metastatic potential to melanoma cells devoid of such ability, such as the primary melanoma cells WM35 and WM98. In vitro invasion assays revealed the ability of miR-30d to significantly enhance the invasive capacity of WM35 and WM98 primary human melanoma cells (FIG. 12D). In vivo, WM98 cells display very poor seeding and colonization of mouse lungs upon tail vein injection, but miR-30d upregulation dramatically increased both the incidence of lung metastasis and the total number of metastasis per lung section (FIG. 12E). These in vitro and in vivo results evidence the strong pro-metastatic potential of this miRNA.

Figure 12F:
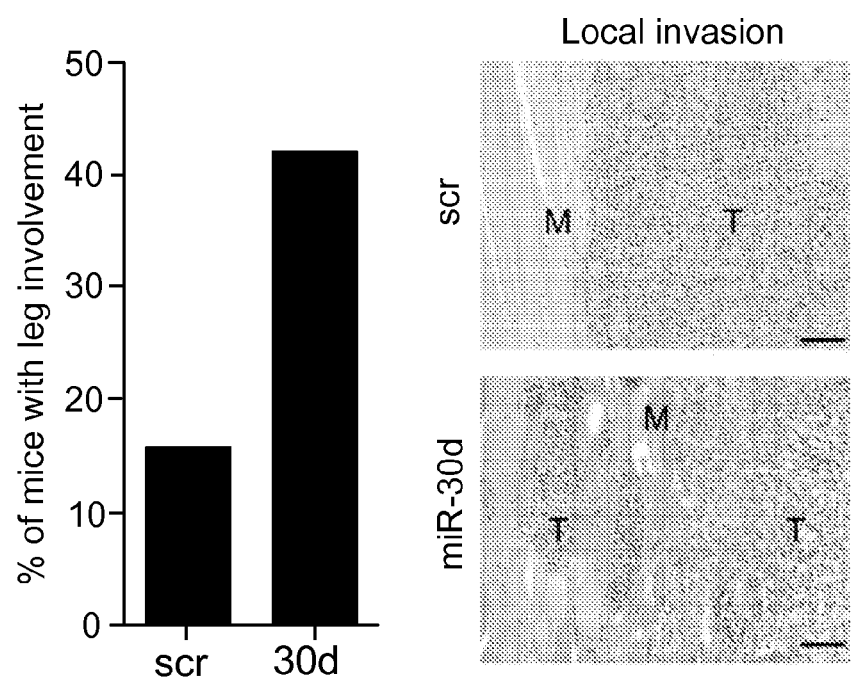
Figure 12G:
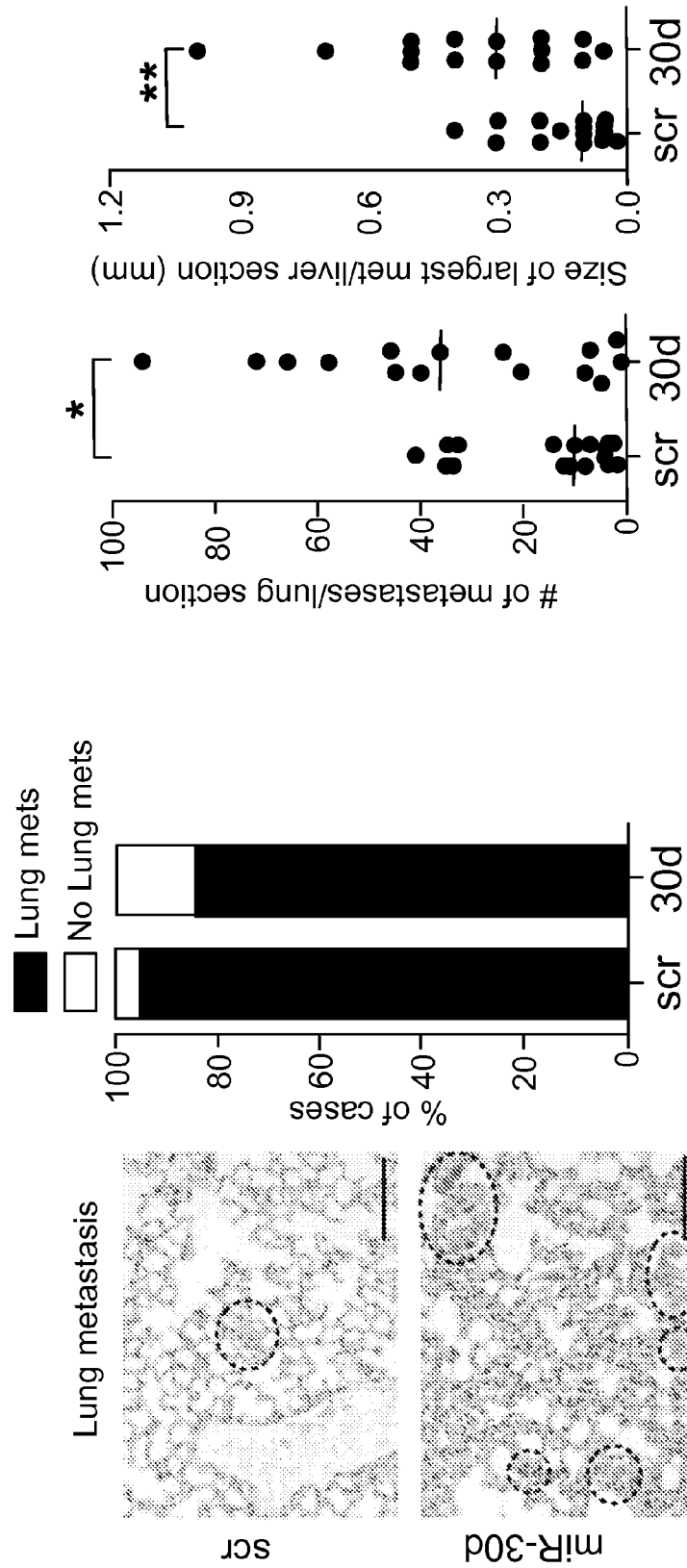
Figure 12H:
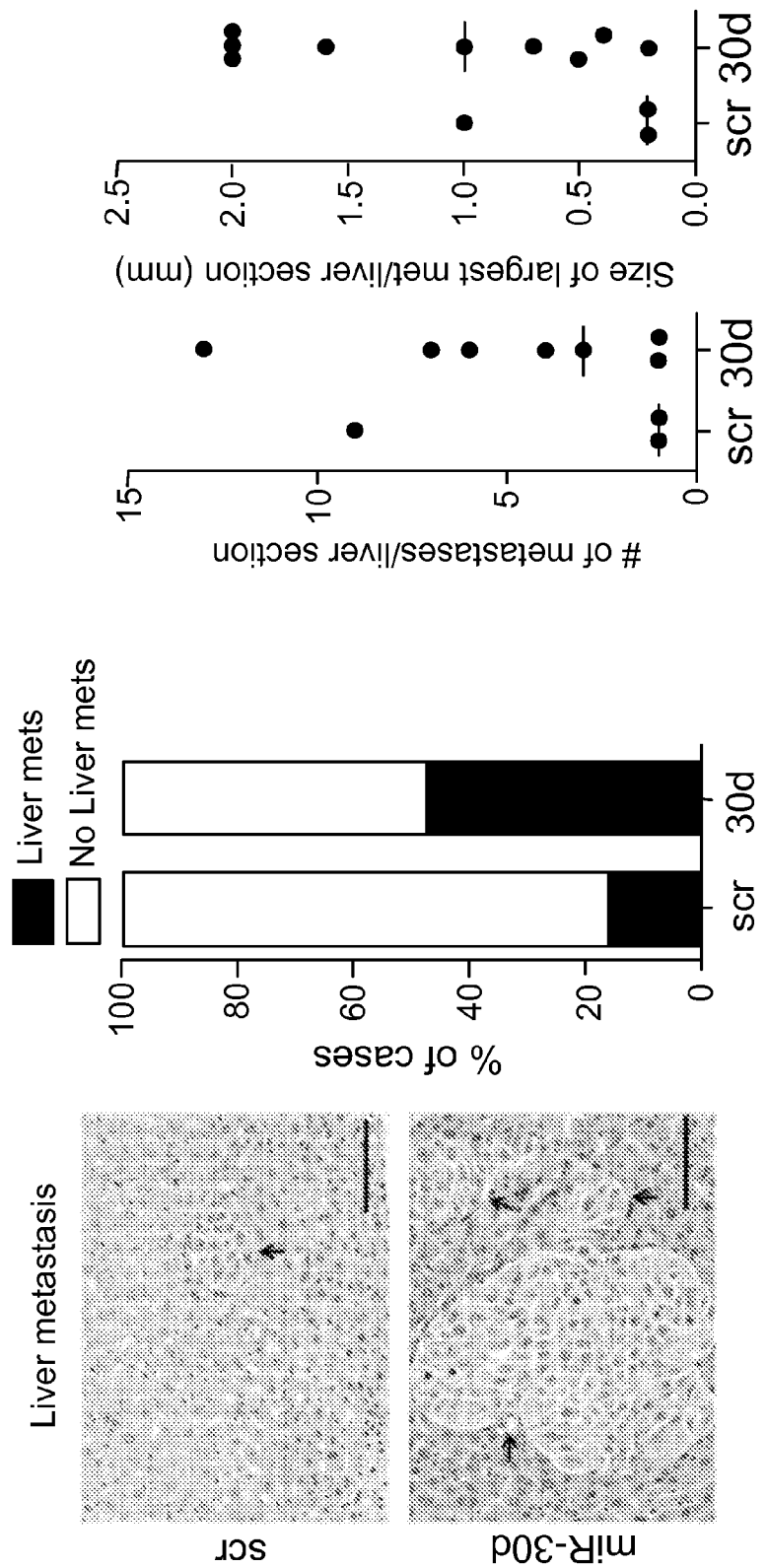

Given the limitations of tail vein injection models at recapitulating all the steps of metastasis, we decided to test the effects of miR-30d in a more preclinical system, in which human melanoma cells are injected in the flanks of immunocompromised mice. These mice form a tumor mass within about 2 weeks, from which cells migrate and reach the lungs in 8-10 weeks with occasional spread to the liver and other organs (Cruz-Munoz et al., 2008). 5B1 cells stably transduced with lentiviruses carrying pre-miR-30d (GIPZ/miR-30d) or a scrambled sequence (GIPZ/scr) were inoculated in the flanks of NOD/Shiscid/IL-2Rγnul (NOG/SCID) mice. Local muscle invasion involving the proximal leg was more commonly found among the GIPZ/miR-30d injected mice than in the GIPZ/scr group (FIG. 12F). Moreover, the proportion of mice that developed liver metastases at completion of the experiment was higher in the miR-30d cohort (9/19) than in the scramble (3/19) (FIG. 12H; p=0.038). Both the number and size of lung and liver micrometastases found 11 weeks after the initial injection were elevated in mice of the GIPZ/miR-30d cohort (FIG. 12G-H). These data demonstrate that miR-30d augments the ability of melanoma cells to either intravasate, extravasate, seed, and/or colonize a distant site.

Example 13

Figure 13D:
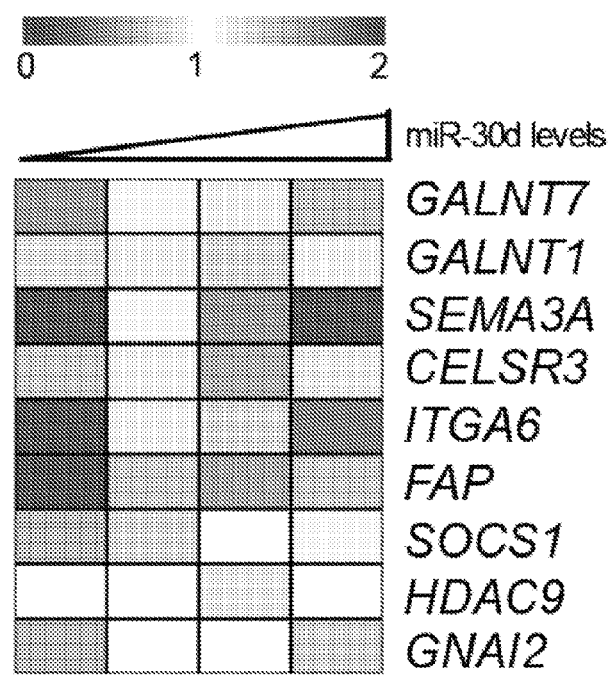
Figure 13G:
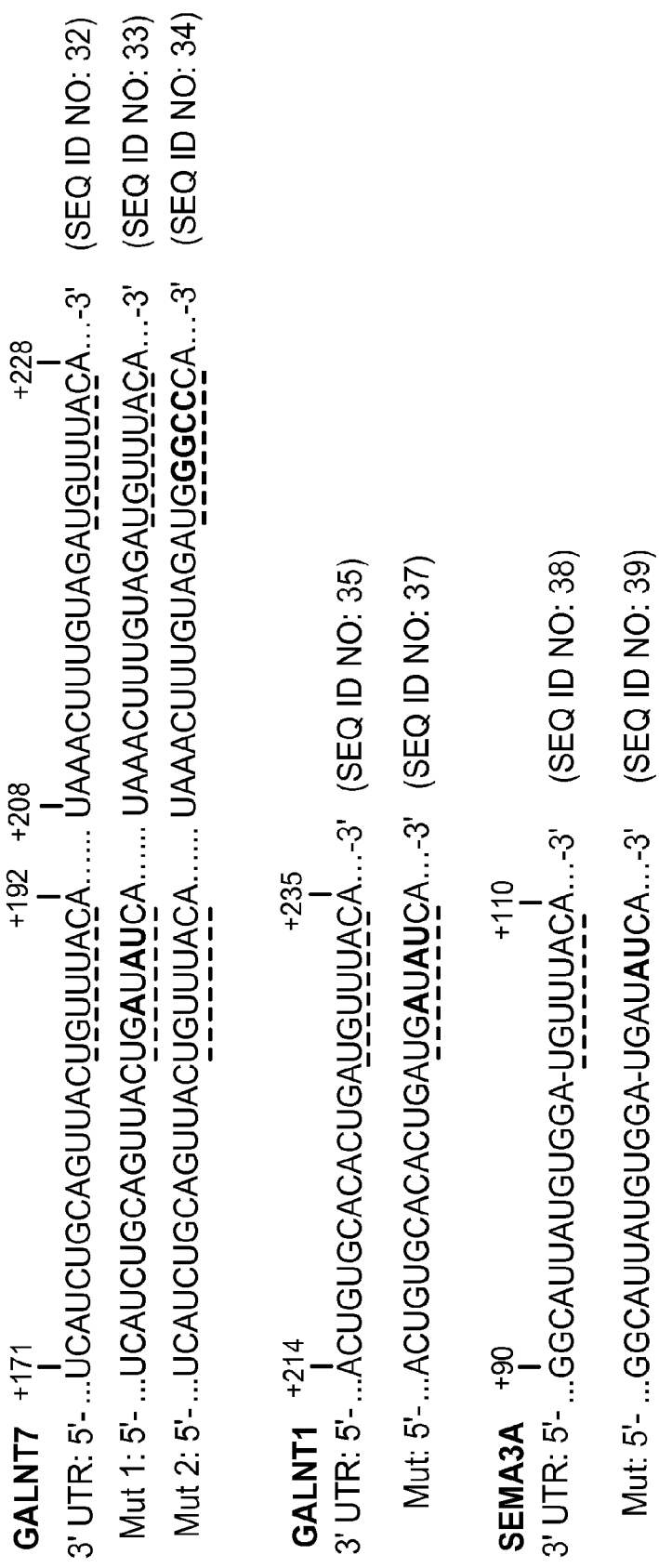
Figure 13H:
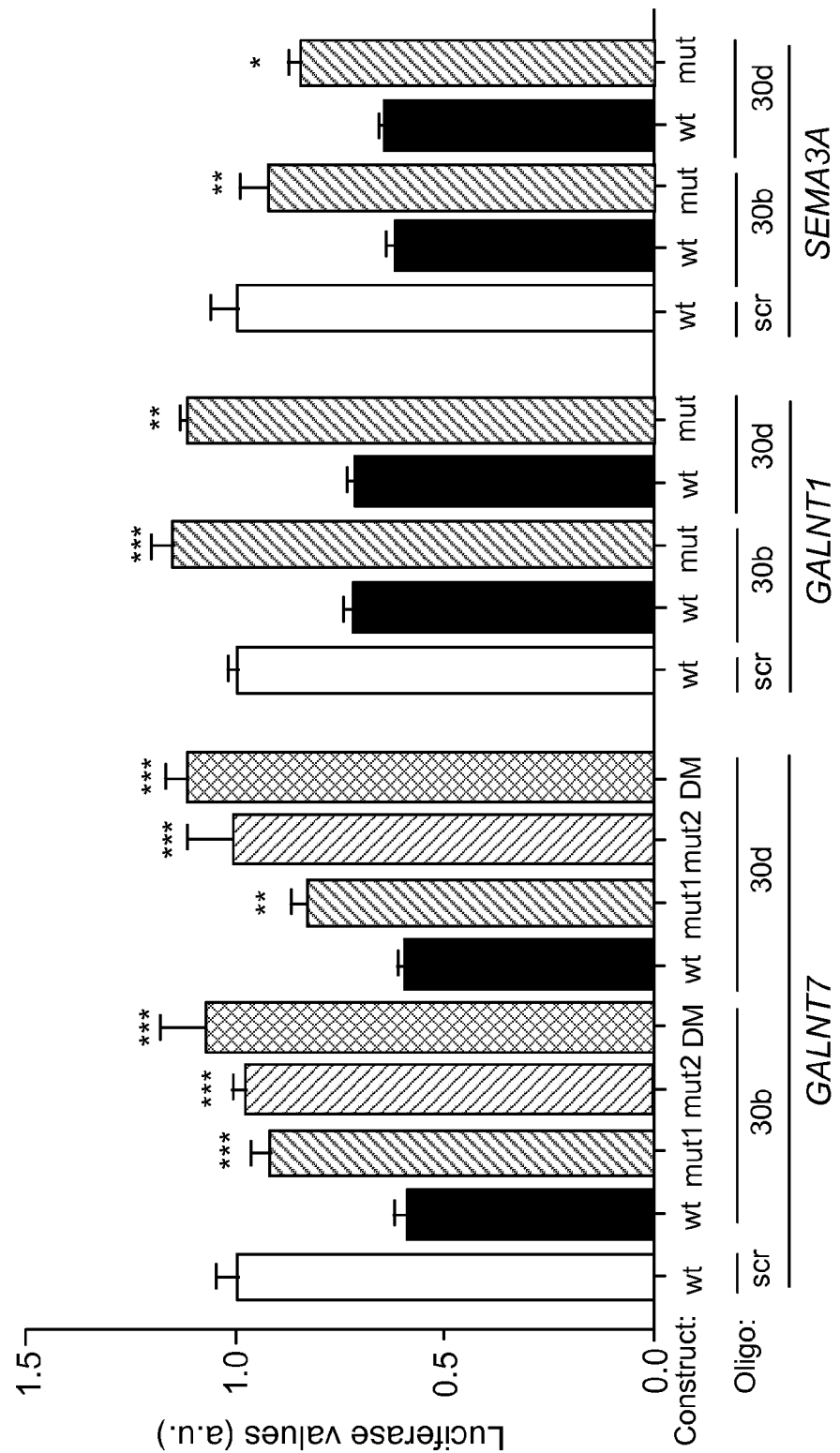

GALNT7, GALNT1, SEMA3, CELSR3 and TWF1 are miR-30b/30d Targets in Melanoma Cells To identify cellular pathways modulated by miR-30d upregulation and to define specific gene targets that might mediate its pro-metastatic effects, we conducted a global transcriptome analysis of 4L and 5B1 cells transduced with miR-30d or scrambled oligonucleotides using Affymetrix arrays. Using thresholds of a minimum fold change of 1.33 and a p value of <0.05, we found 784 genes to be differentially expressed by the two cell lines. Gene ontology analysis revealed candidate genes whose altered expression could contribute to the invasive phenotype induced by miR-30d (FIG. 13A). Of the 784 altered genes, we found 217 genes down-regulated in 4L, 180 downregulated in 5B1, and 58 downregulated in both lines. Nearly one-third of the downregulated genes were direct miR-30d targets predicted by public algorithms (TargetScan) (Lewis et al., 2005) (FIG. 13B), and included GNAI2, a validated miR-30d target (Yao et al., 2009). Meanwhile, the overlap with targets of a randomly selected miRNA was minimal (FIG. 13C). Interestingly, data mining of our previously published mRNA profile of human metastatic melanoma tissues (Bogunovic et al., 2009) revealed that miR-30d levels inversely correlate with expression of several targets identified in our array analysis, including SEMA3A, GALNT1, and GALNT7 (FIG. 13D), further supporting the physiological relevance of this regulatory mechanism. The expression levels of other GALNT family members, many of which carry recognition sites for miR-30d in their 3'-untranslated regions (3'-UTR), also inversely correlated with miR-30d levels in those tissues (data not shown). Using 3' UTR luciferase reporter assays and quantitative RT-PCR, we confirmed that GALNT7, GALNT1, SEMA3, CESLR3 and TWF1, are direct targets of miR-30b/30d (FIG. 13E, F). Mutations in the miRNA recognition sites (FIG. 13G) rendered the constructs unresponsive to miR-30b or miR-30d induction (FIG. 13H), further confirming that these are direct miR-30b/30d targets.

Example 14

GALNT7 is a Critical Mediator of miR-30d Pro-Invasive Effects In Vitro and Pro-Metastatic In Vivo Next, we investigated which, if any, miR-30d direct targets mediate the capacity for cellular invasion. Several candidates seemed appealing: CELSR3 is involved in contact-mediated cell-to-cell communication (Wu and Maniatis, 1999), TWF1 encodes for twinfilin (Palmgren et al., 2002) which regulates cell motility and Semaphorin 3A (SEMA3A) exerts antiangiogenic properties (Maione et al., 2009). GalNAc transferases (GalNAc-Ts) initiate mucin-type O-linked glycosylation in the Golgi apparatus by catalyzing the transfer of N-Acetylgalactosamine (GalNAc) to serine and threonine residues on target proteins. These post-translational modifications affect the structure of numerous transmembranal substrates, determining their functional interaction with the extracellular environment (Ten Hagen et al., 2003).

Figure 14A:
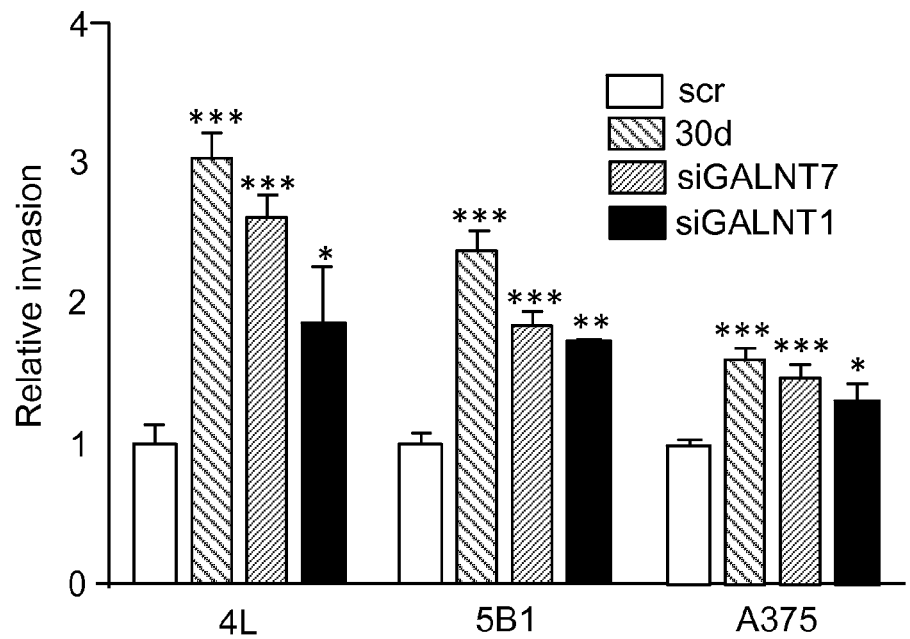
FIGS. 14A-14D GALNT modulation accounts for miR-30d pro-invasive effects in vitro and in vivo. 14A-14B. Transwell invasion assay of indicated cell lines transfected with scrambled control, miR-30d, siGALNT7, siGALNT1 (50 nM each and additional 5 µg/ml of empty vector), GALNT7 cDNA (5 µg/ml and 50 nM of scrambled oligo), or co-transfected with miR-30d (50 nM) and GALNT7 cDNA (5 µg/ml). 14C-14D. In vivo metastasis assay with B16F10 mouse melanoma cells. 14C. Cells were transiently transfected with scr, miR-30d mimics or siGALNT7 oligos and injected through the lateral tail vein of C57BL/6J mice (n=10 per group). Levels of knockdown or over expression are shown on the left. Histogram and macroscopic pictures depict the increase in metastatic behavior when miR-30d was over-expressed or when GALNT7 was downregulated. 14D. Cells were stably transduced with either pEIGW-Empty or pEIGW-mmu-GALNT7. 24 hours prior to injection, cells were transfected with either scr control or miR-30d oligonucleotides. Cells were injected through the lateral tail vein of NOG/SCID mice (n=10 per group). Levels of overexpression are shown on the left. Histogram and macroscopic pictures depict the increase in metastatic behavior when miR-30d was over-expressed, but co-expression of GALNT7 reduced the cells' metastatic potential to their basal levels (empty+scr condition). (mean±SEM; *p<0.05; p<0.01; *p<0.001).
Figure 14B:
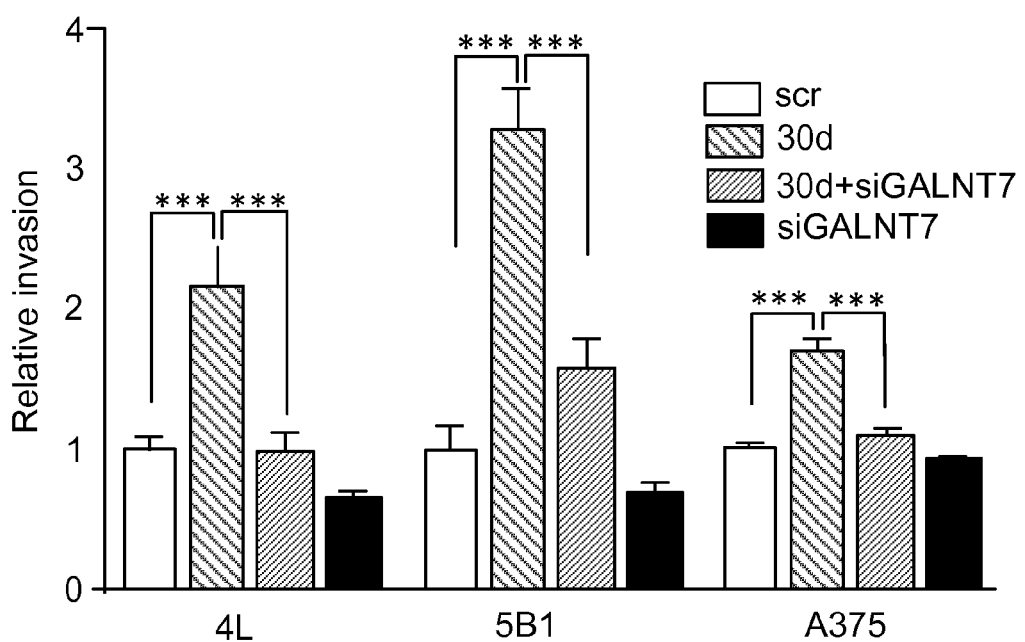

Given their described roles, all these molecules seemed plausible candidates to shape the pro metastatic influence of miR-30b/30d. To determine whether any of them were critical mediators of miR-30d's role in cellular invasion, we silenced each of them using RNA interference (RNAi) in melanoma cell lines. While downregulating SEMA3A, CELSR3 and TWF1 did not enhance invasion, repression of GALNT7, and to a lesser extent GALNT1, recapitulated the pro-invasive effects of miR-30d (p<0.0001 for GALNT7; p=0.004 for 5B1 and 0.01 for A375 for GALNT1; FIG. 14A). Moreover, coexpression of a GALNT7 cDNA lacking the 3'UTR was able to suppress miR-30d promotion of cell invasion, indicating that GALNT7 silencing critically mediates miR-30d's pro-migratory effects in melanoma (p<0.0001; FIG. 14B).

Figure 14C:
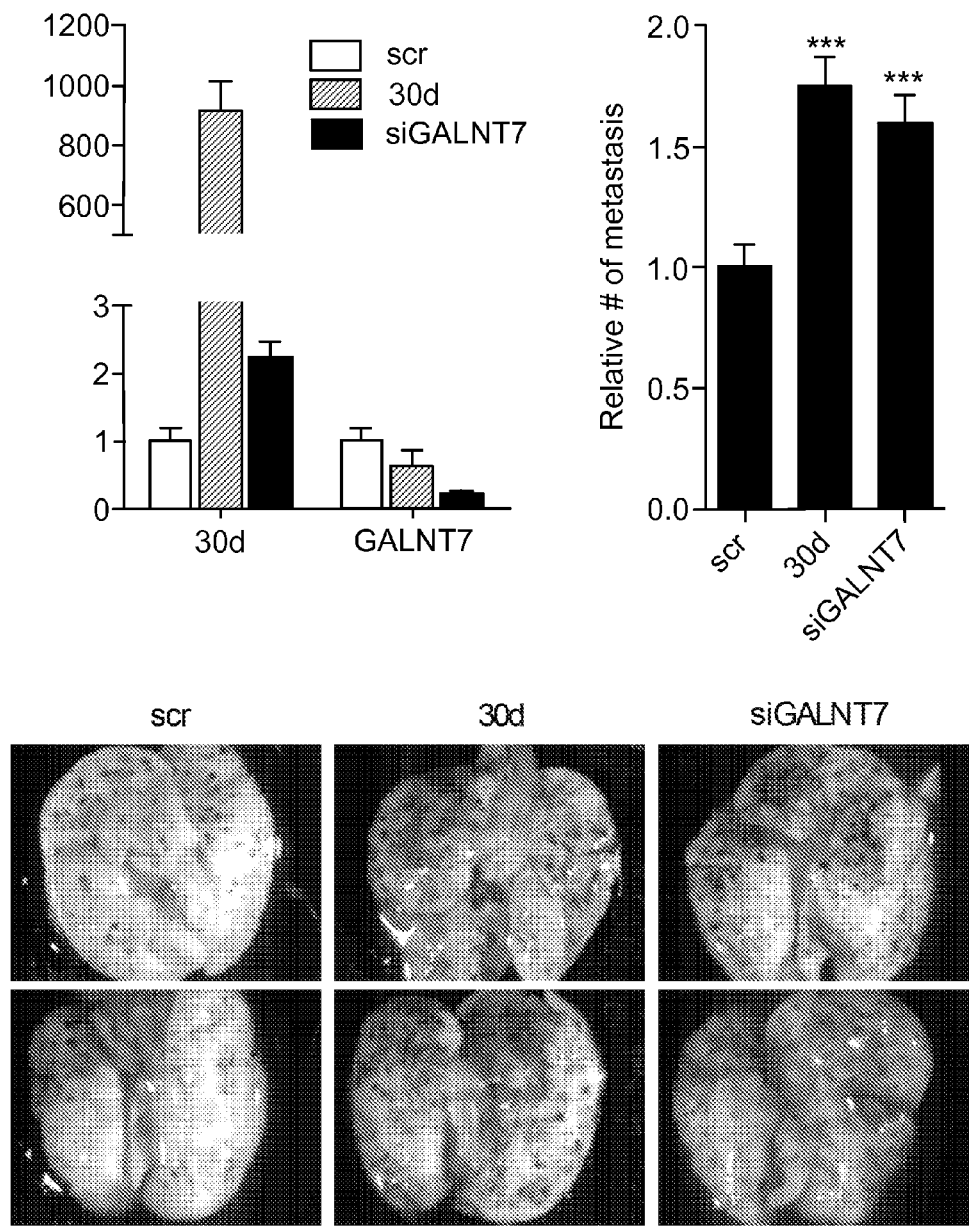
Figure 14D:
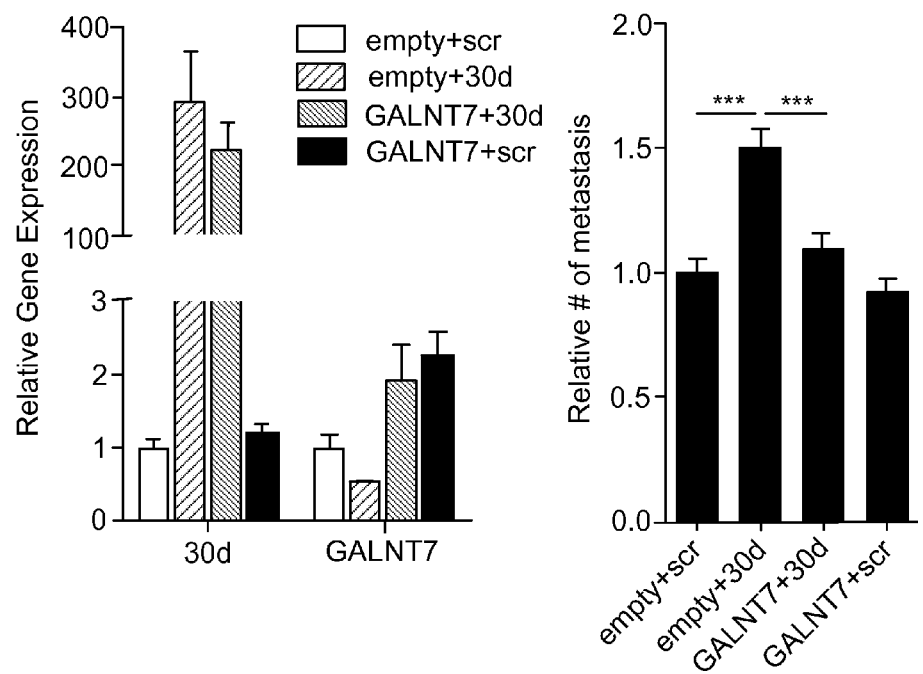
Figure 14D:
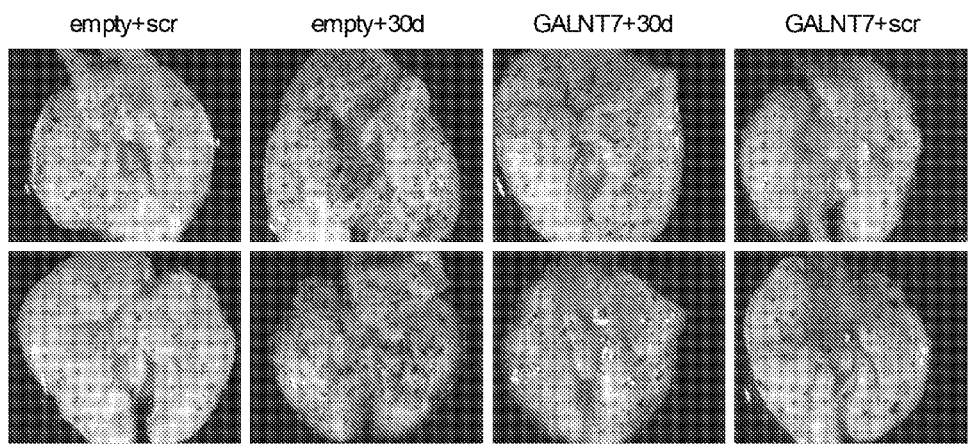

GALNT7 silencing by siRNA oligonucleotides was able to mirror miR-30d's promotion of B16F10 metastatic capacity upon tail vein injection (p=0.0006; FIG. 14C). Finally, we compared the metastatic potential of B16F10 cells transduced with miR-30d oligonucleotides and either an empty lentiviral vector or one expressing the murine GALNT7 cDNA. Concomitant ectopic expression of GALNT7 with miR-30d abolished miR-30d' pro-metastatic effect (p=0.0002; FIG. 14D). Overall, our in vitro and in vivo data support GALNT7 inhibition as a key contributor of miR-30d's pro-metastatic effects in melanoma cells.

Example 15

Figure 15A:
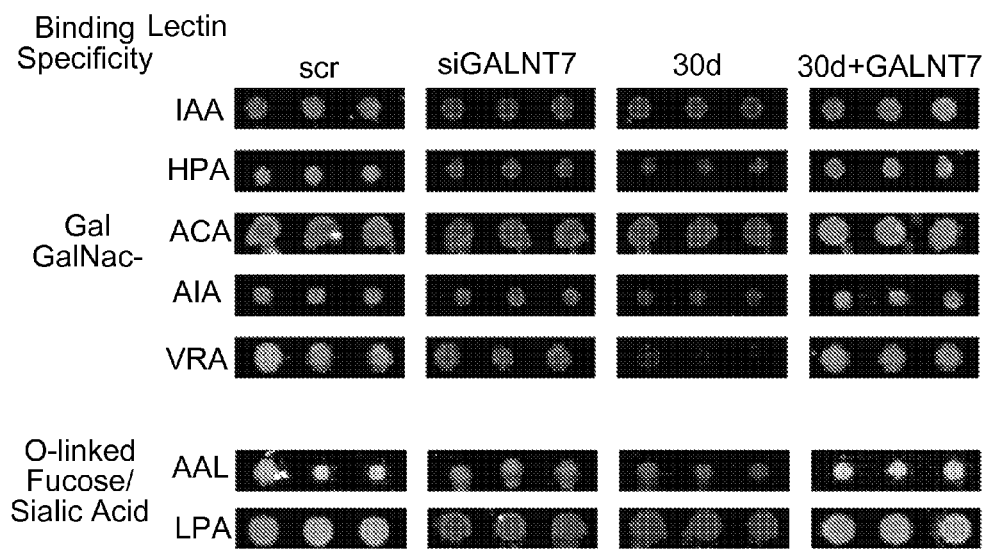
FIGS. 15A-15B GALNT modulation accounts for miR-30d-mediated alterations in membranous O-linked glycans. 15A-15B. Lectin microarray analysis of 5B1 cells transiently transfected with scrambled control, miR-30d, siGALNT7, or co-transfected with both miR-30d and GALNT7 cDNA (as described in 15A).
Figure 15A:
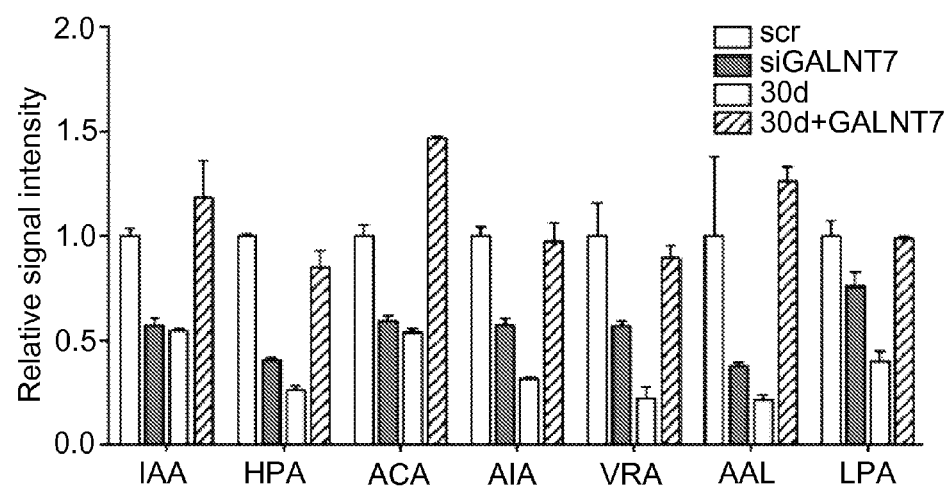
Figure 15B:
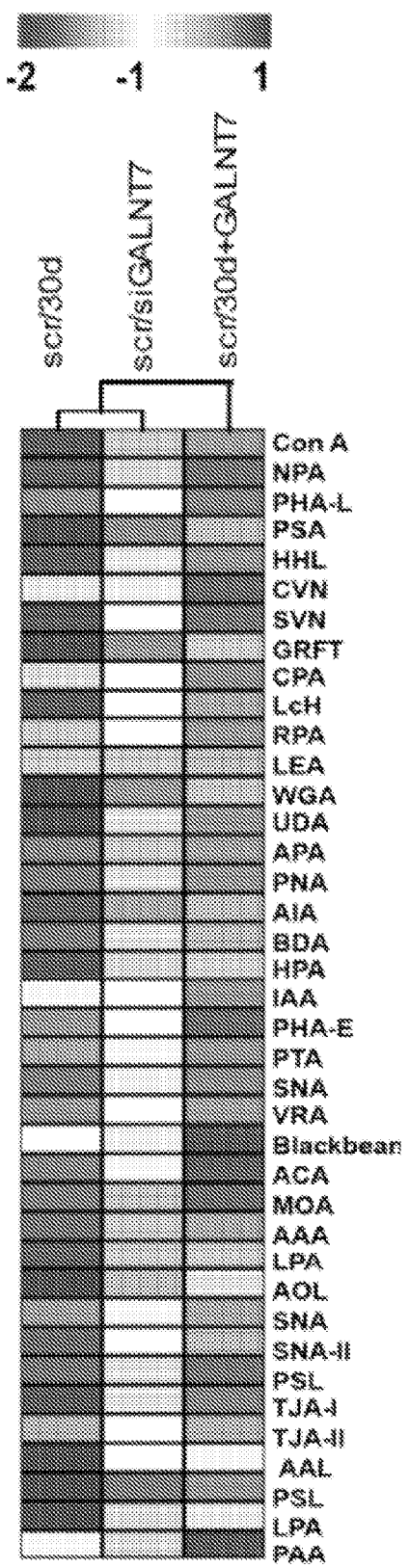

MiR-30d Overexpression and GALNT7 Inhibition Produce Similar Glycomic Changes, Which are Rescued by GALNT7 Ectopic Expression We hypothesized that inhibiting GALNT7 could promote cell invasion by modifying the O-glycosylation patterns of membrane proteins that interact with the extracellular matrix and cells of the tumor microenvironment. To test this hypothesis, we obtained glycomic profiles of melanoma cells transfected with miR-30d only, siGALNT7 only, miR-30d together with GALNT7 cDNA, and scrambled control miRNA, using lectin microarrays consisting of 84 discrete carbohydrate-binding proteins (Krishnamoorthy et al., 2009). We analyzed cellular micellae from isolated cell membranes, which previous work has shown to contain both glycoproteins and glycolipids representative of the cell surface (Pilobello et al., 2007). Our lectin microarray analysis revealed an overall decrease in glycosylation in both siGALNT7 and miR30d-transduced cells relative to scrambled control, affecting both N- and O-linked glycosylation (data not shown). The most pronounced conserved effects across both miR-30d and siGALNT7, based on single color array data, were on secondary modifications such as fucose and sialic acid as well as terminal GalNAc, confirming a predominant effect on O-linked glycosylation (FIG. 11 5A). Importantly, co-transfection of GALNT7 cDNA rescued these glycosylation defects for both N— and Olinked glycans (FIG. 15A). To facilitate direct comparisons among samples, we utilized a more sensitive ratiometric two-color approach (Krishnamoorthy et al., 2009) in which cell membrane micellae from scrambled-transduced cells served as a common biological reference. These data confirmed the observed general reduction in both N- and O-linked glycosylation (FIG. 15B). Similar but not completely overlapping changes were induced by siGALNT1 (data not shown). That similar glycosylation changes are induced by both miR-30d upregulation and siGALNT7, and are restored by re-expressing GALNT7, supports the key contribution of GALNT7 repression to miR-30d-associated phenotypes. It is likely that those modified glycosylation patterns act as direct or indirect mediators of miR-30d's pro-metastatic role.

In order to determine the contribution of chemokine receptors signaling to the pro-metastatic role of miR-30d, we investigated the effects of blocking intracellular signaling by incubating the melanoma cells with Pertussis toxin (PTX), which is known to catalyze the ADP-ribosylation of the α subunits of the heterotrimeric G protein, and prevents G1 proteins from interacting with G-protein coupled receptors on the cell membrane. Pretreatment of melanoma cells with PTX (100 ng/ml; 24 h) had little to no effect on miR-30d's pro-metastatic potential in a tail vein injection experiment (data not shown). This suggests that G1-dependent chemokine signaling does not contribute significantly to the effects of miR-30d or GALNT7 on extravasation, seeding or colonization, but we cannot rule out a G1-independent chemokine signaling.

Example 16

MiR-30d Stimulates the Expression of the Immunosuppressive Cytokine IL-10 by Repressing GALNT7

Figure 16A:
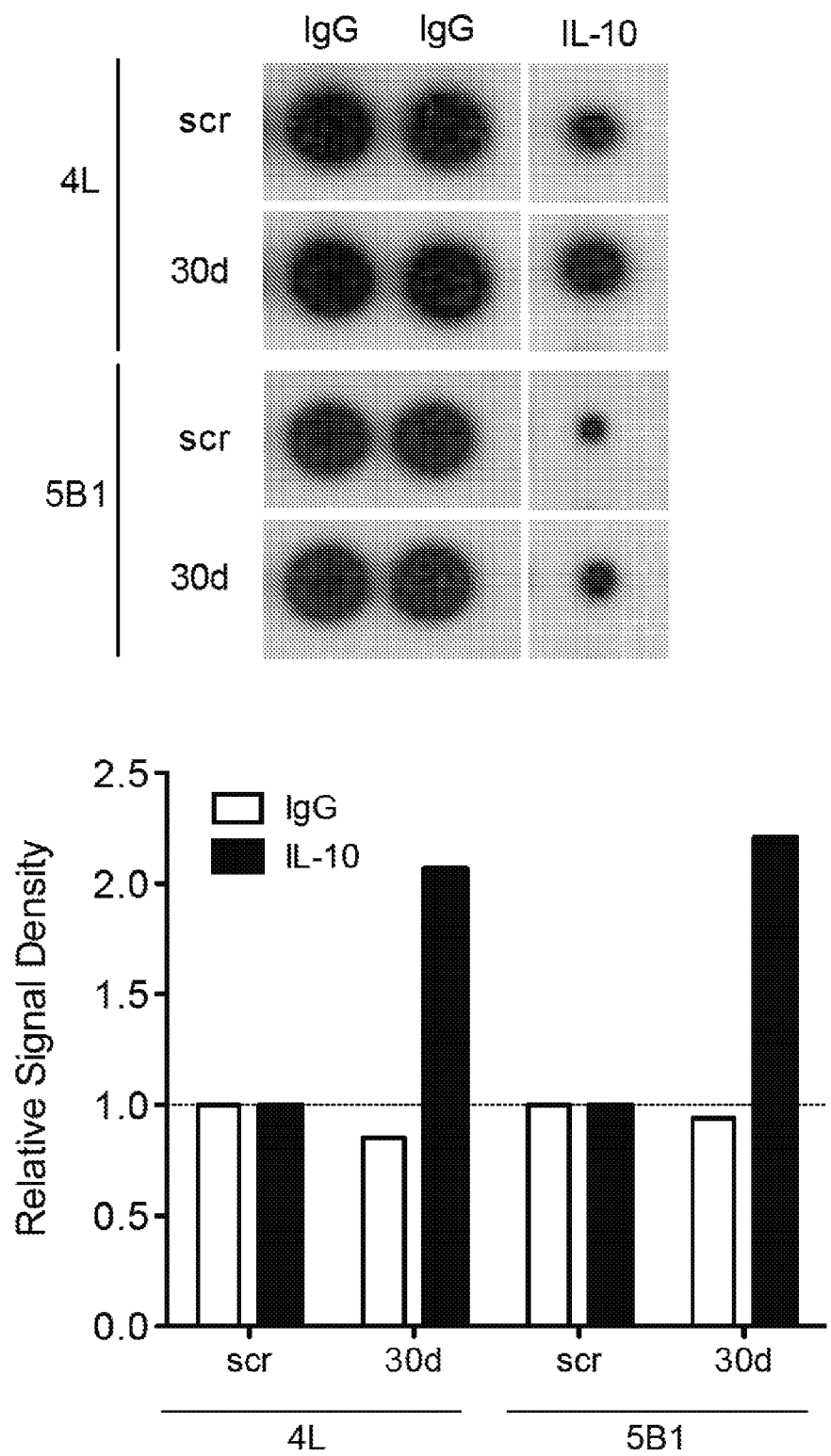
FIGS. 16A-16F MiR-30d promotes IL-10 secretion by suppressing GALNT7. 16A. Elevated levels of IL-10 in melanoma cells transduced with miR-30d relative to scrambled (src) control (50 nM) measured by cytokine array. Quantification of signal density is presented on the right. B. Levels of phosphorylation of proteins that might explain the increase in IL-10 secretion from miR-30d-transfected cells as measured by solid phase ELISA in indicated cell lines. Inset: levels of IL-10 secreted from the cells, quantified by ELISA. 16C. Western blot validated increased phospho-STAT3 levels in miR-30d-transfected cells with no change to total STAT3 in A375 cells transfected with scr or miR-30d mimic oligonucleotides. Tubulin served as loading control. 16D. Elevated IL-10 mRNA levels in siGALNT7-transfected melanoma cell lines 4L and 5B1 relative to scr control measured by quantitative PCR. 16E. Increased secretion of IL-10 to the supernatant of siGALNT7-transfected melanoma cell lines 4L and 5B1 as compared to scr-transfected cells, measured by ELISA. 16F. Re-expression of GALNT7 in miR-30d-transfected cells reversed the increase in IL-10 mRNA levels in indicated melanoma cells transfected with scr, GALNT7 cDNA, or co-transfected with both miR-30d and GALNT7. (*p<0.05)
Figure 19A:
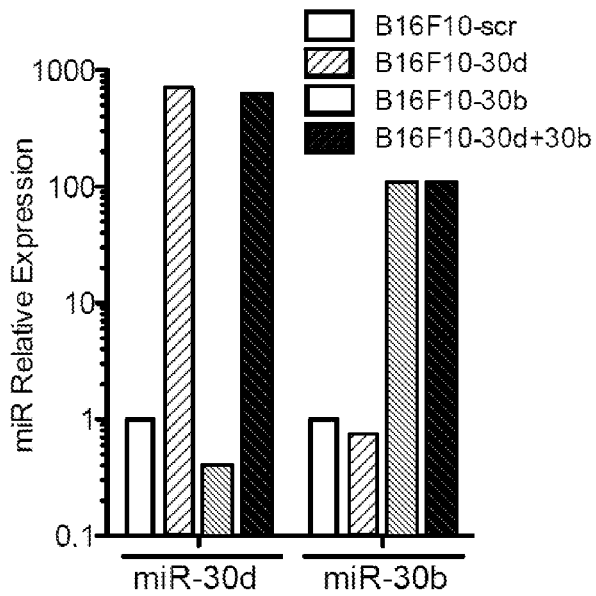
FIGS. 19A-19D MiR-30b recapitulates miR-30d effects on melanoma metastasis in vitro and in vivo and IL-10 expression in vitro. A-C. In vivo metastasis assay with B16F10 mouse melanoma cells transiently transfected with scr, miR-30d, miR-30b or both miR-30d and miR-30b mimics injected through the lateral tail vein of C57BL/6J mice (150 nM; n=10 per group). A. Histogram shows the levels of miR expression in each treatment group. B. Histogram shows that both miR-30b and miR-30d increase metastatic behavior with no additive or synergistic effects of their concomitant ectopic expression. C. Histogram shows the average number of micrometastases per treatment in 3 lung sections per specimen. D. Histogram represents the relative expression of IL-10 as determined by qRT-PCR. The ectopic expression of both miR-30b or miR-30d increased the expression of IL-10 in 5B1 melanoma cells. The increase in IL-10 is neutralized when GALNT7 cDNA is concomitantly introduced in the cells.
Figure 19B:
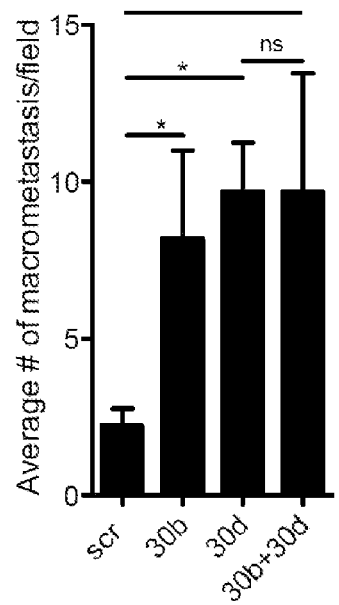
Figure 19C:
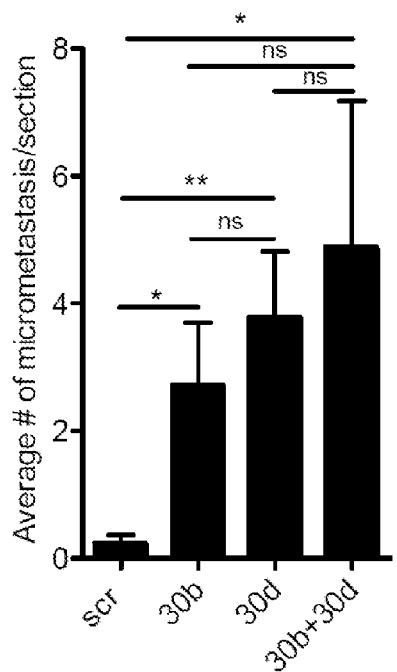
Figure 19D:
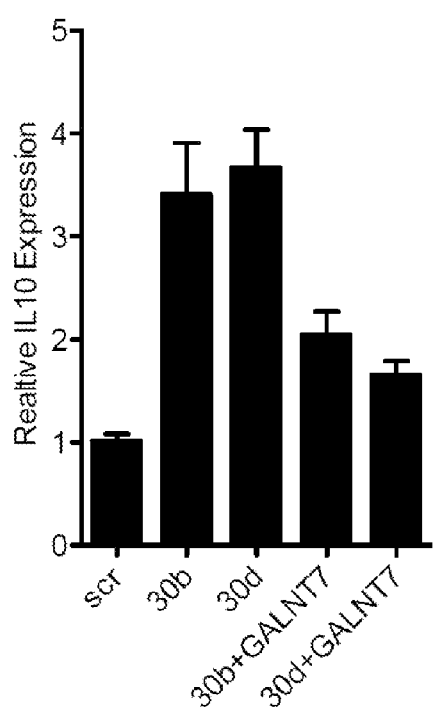

Our microarray analyses in two independent cell lines revealed that miR-30d ectopic expression results in mRNA upregulation of some immune modulators, among them the immunosuppressive immunoglobulin CTLA4 and the immunosuppressive cytokine interleukin-10 (IL-10) (FIG. 19A). Using human cytokine antibody arrays and ELISA, we confirmed that melanoma cells transfected with miR-30d and 30b mimics secrete significantly more IL-10 than scrambled controls (FIGS. 16A and 19D).

Figure 16B:
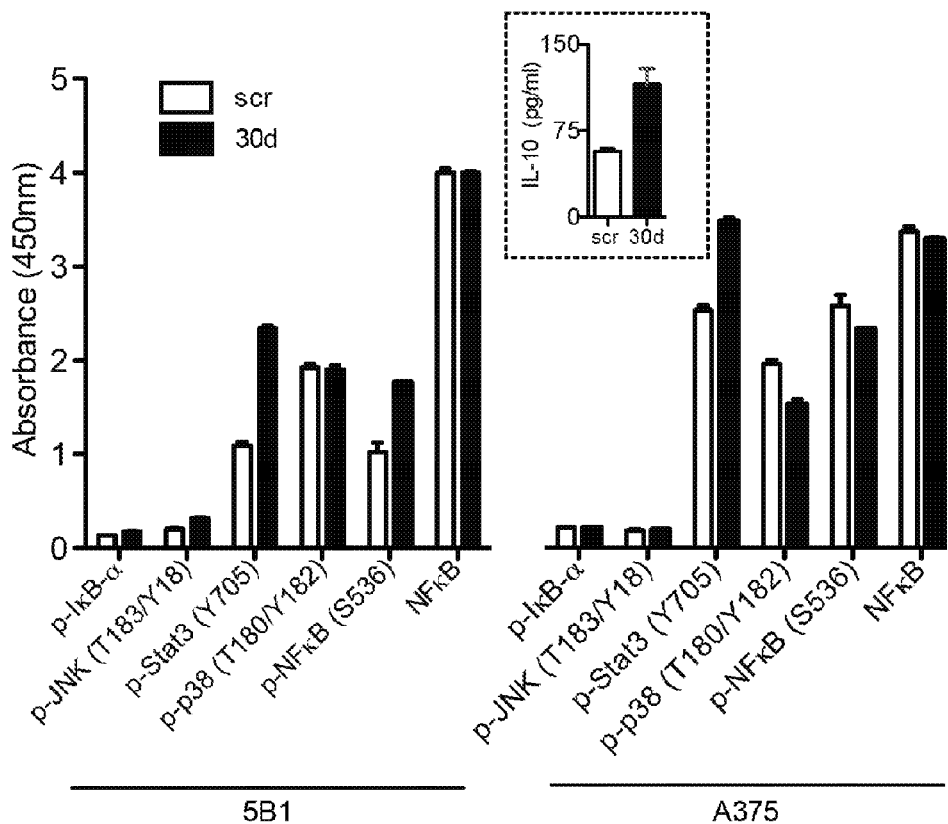
Figure 16C:
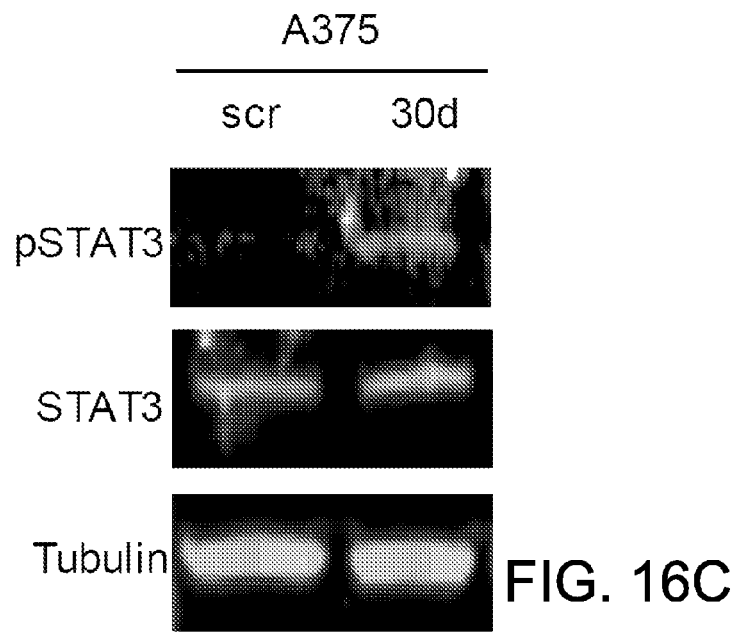
Figure 16F:
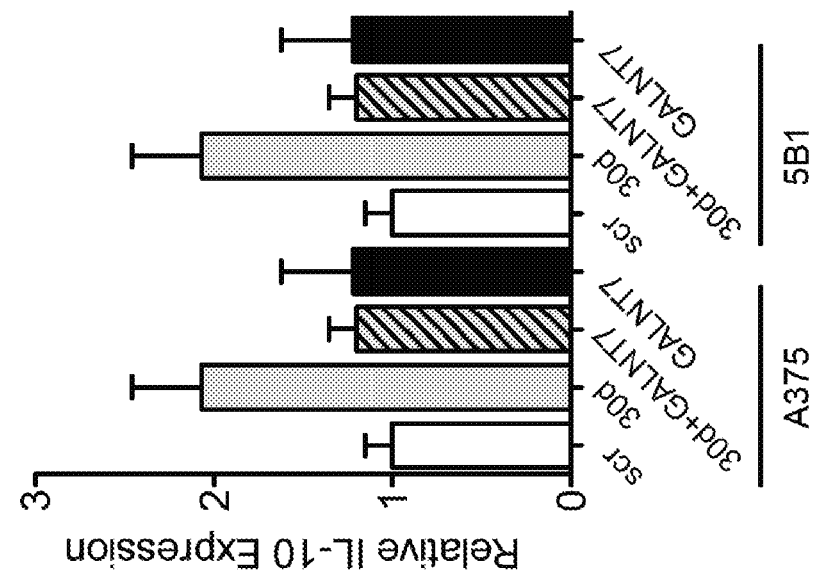
Figure 16E:
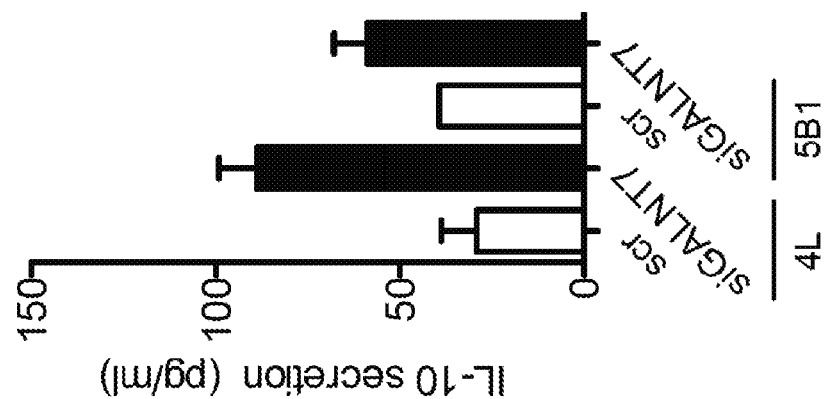
Figure 16D:
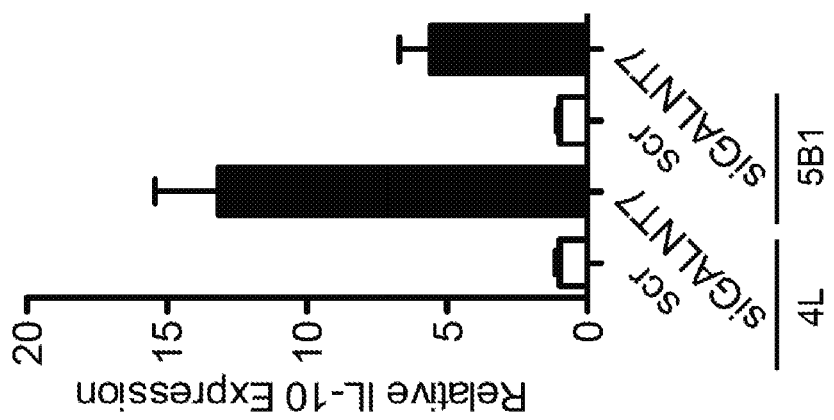

In search of a mechanism accounting for miR-30d-mediated induction of IL-10, we tested the effect of miR-30d on the major signaling pathways known to modulate IL-10 levels (i.e., PI3K, STAT3, NF-κB, p38MAPK, JNK). Melanoma cells that overexpress miR-30d displayed increased levels of phospho-Tyr705-STAT3 (FIG. 16B-16C), which is known to transcriptionally activate IL-10 as well as numerous prometastatic genes (Yu et al., 2009). Although STAT3 activation could partially explain the elevated IL-10 expression, we asked whether any of our identified miR-30d direct targets could contribute to it. Surprisingly, we found that GALNT7 silencing is sufficient to induce IL-10 synthesis and secretion to levels comparable to those induced by miR-30d (FIG. 16D-16E) or miR-30b (FIG. 19 D), and that GALNT7 overexpression counteracts miR-30d (FIG. 16F) or miR-30b-mediated (FIG. 19D) IL-10 upregulation. These results suggest that miR-30d/30b induce IL-10 at least in part by repressing GALNT7, revealing an unexpected role for a single GalNAc transferase in linking tumor cell invasion and immune modulation.

Example 17

Figure 17D:
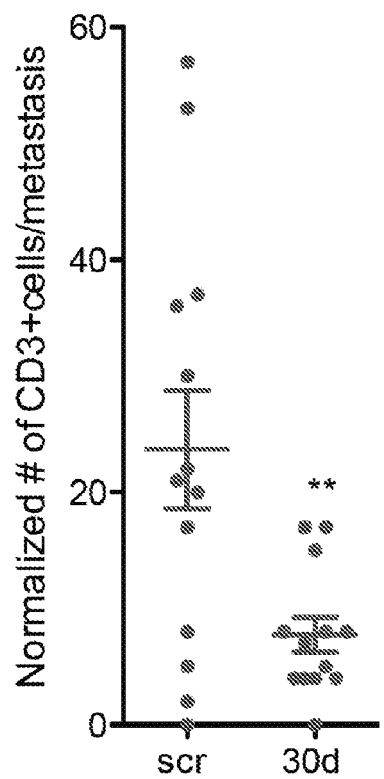
Figure 17D:
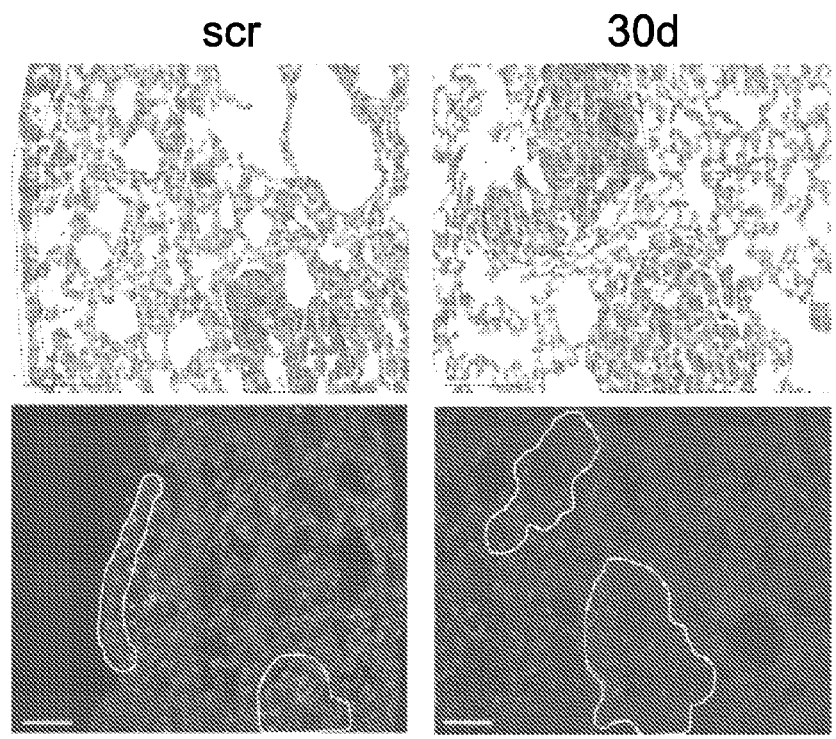
Figure 17E:
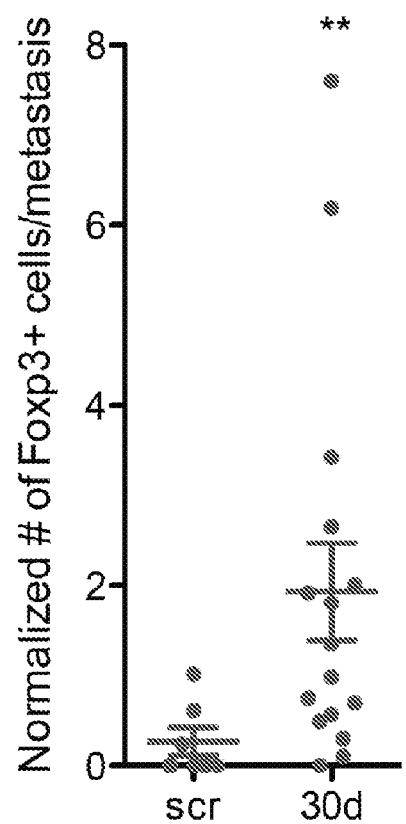
Figure 17E:
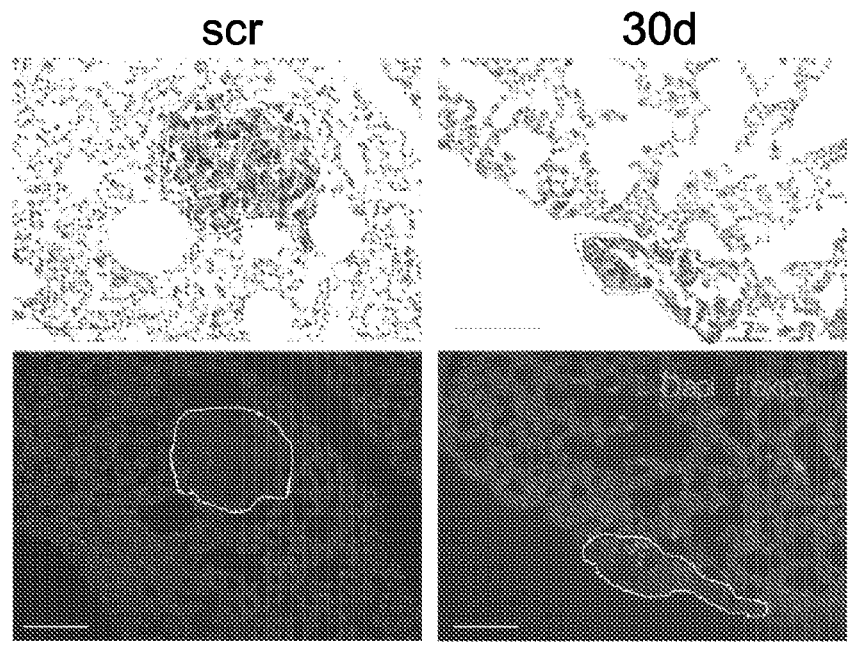
Figure 20B:
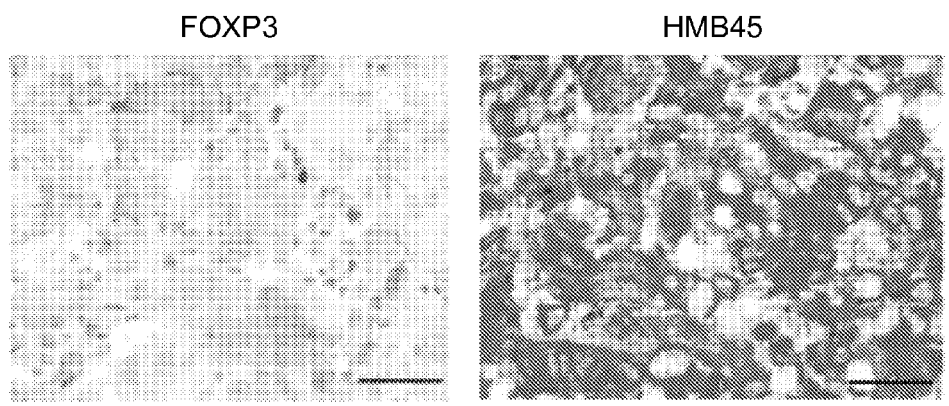
Figure 21:
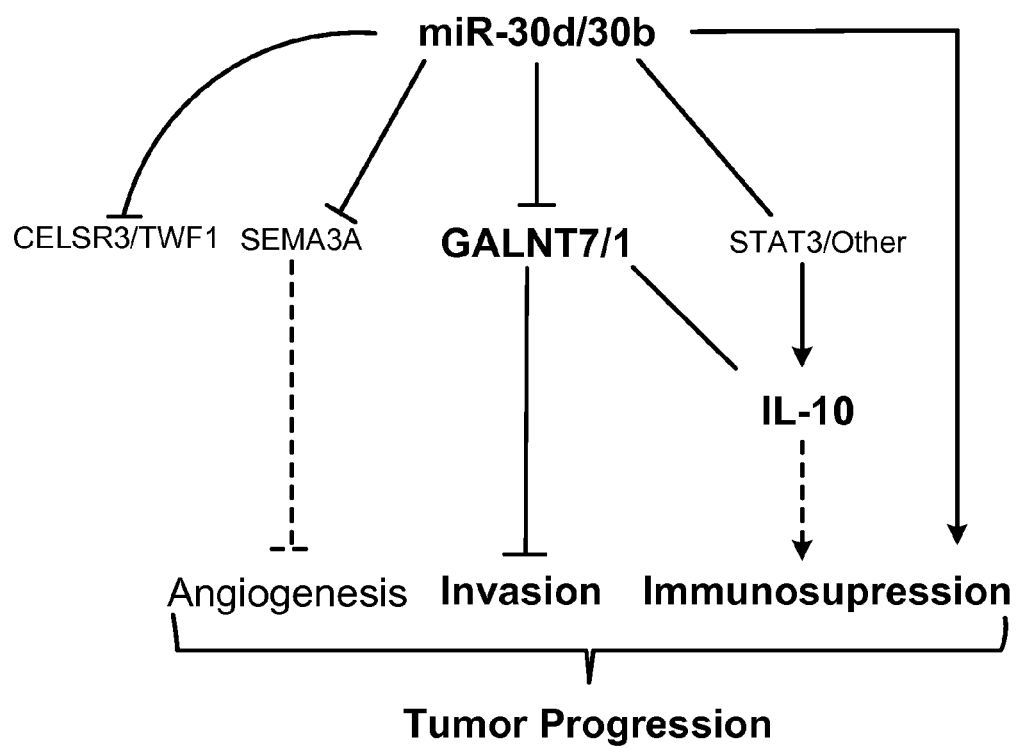
FIG. 21A model depicting miR-30b/30d-mediated prometastatic functions. MiR-30b/30d are upregulated during metastasis and associate with patients poor survival and shorter time to recurrence. miR-30b/30d increase cancer cells' invasiveness and metastatic potential mainly via the down-regulation of their direct target GALNT7. Additionally these miRNAs may contribute to tumor progression by eliciting immune evasion that is partially mediated by the immunosuppressive cytokine IL-10. Other pro-tumorigenic effects that may occur by the silencing of other direct targets remain to be explored.

MiR-30b/30d Upregulation Triggers Immunosuppressive Properties at the Metastatic Site To determine whether aberrant miR-30d expression is able to promote an immunosuppressive environment in vivo, we compared the recruitment of T cells (CD3+), regulatory T-cells (Tregs CD4+CD25+Foxp3+), activated dendritic cells (DCs, MHCII+F480-CD86+), and myeloid-derived suppressor cells (MDSCs, CD11b+Gr1+) in the lungs of immunocompetent mice injected with B16F10/scr or B16F10/miR-30d cells through the tail vein. FACS analysis showed that lungs of B16F10/miR-30d injected mice contain significantly more Tregs (p=0.03; FIG. 17A) than the equivalent scrambled controls, with moderate changes in activated DCs and no significant changes in MDSCs (data not shown). Differences were more prominent when individually macro-dissected metastases were analyzed; we note that metastases from mice injected with B16F10/miR-30d displayed lower local levels of CD4 mRNA (p=0.039; FIG. 17B) and higher levels of Foxp3 mRNA (normalized to CD4 levels in the tissue; p<0.01; FIG. 17C) than those from mice injected with B16F10/scr cells Immunofluorescence stainings confirmed both the reduction in T-cell accrual (FIG. 17D) and the increased recruitment of Tregs to the metastases of B16F10/miR-30d cells (FIG. 17E). In accordance, immunohistochemistry analysis of human metastatic melanomas (n=32) revealed some association between miR-30d levels and FOXP3 expression in infiltrating lymphocytes (p=0.11; data not shown). Interestingly, we found a significant correlation between FOXP3 expression and miR-30d levels in the tumor cells themselves (n=45; p=0.02; FIG. 20). To confirm that FOXP3 is indeed expressed by melanoma cells, we conducted HMBA-45 immunohistochemistry stainings in consecutive tissue sections (FIG. 20B). Overall, these results suggest that miR-30d might contribute to metastasis not only by promoting migration but also by suppressing immune surveillance.

Figures 18A, 18B:
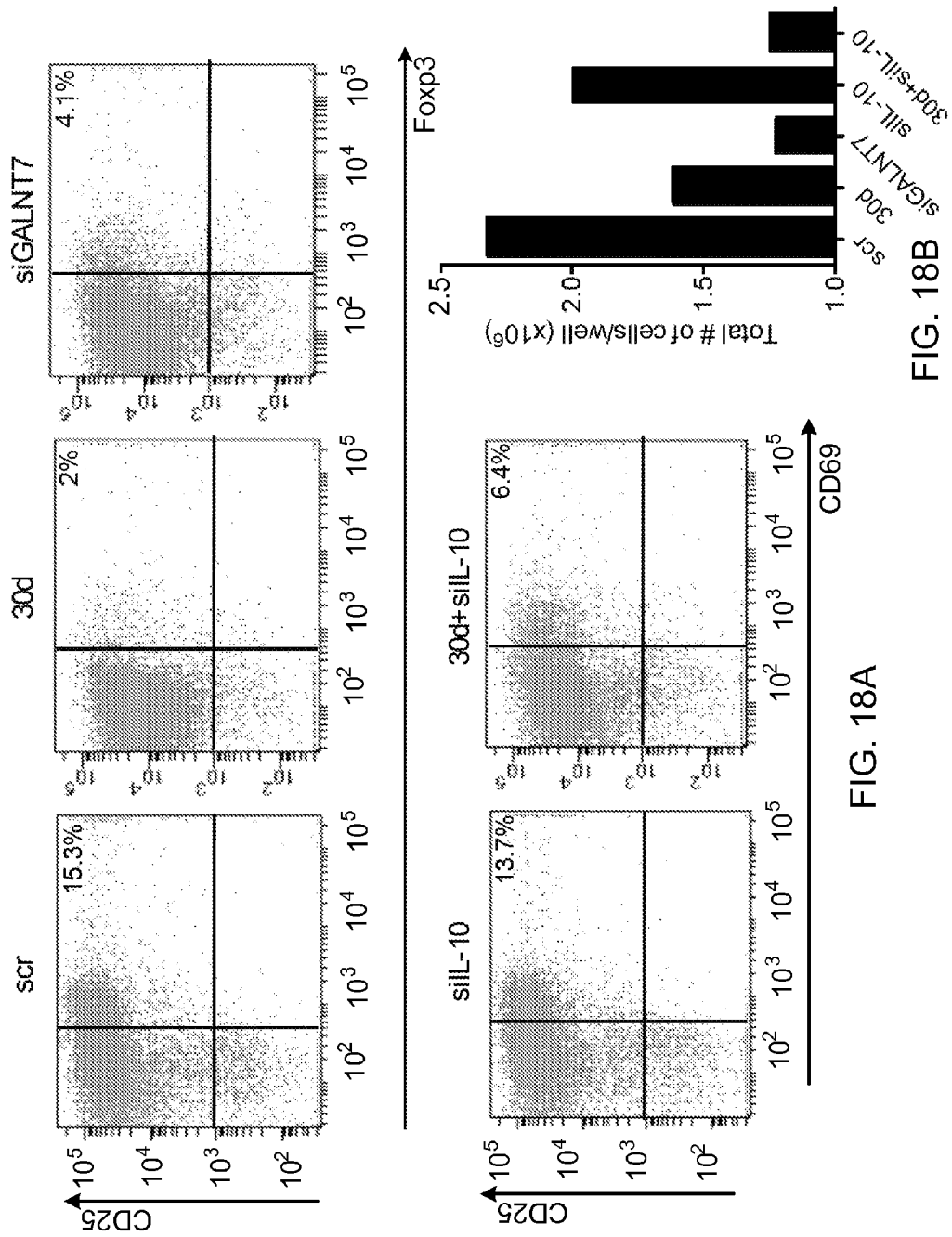
FIGS. 18A-18D GALNT modulation accounts for miR-30d-mediated immunosupressive effects ex vivo. 18A. FACS analysis of activated (CD25+CD69+ gated on CD4+) T lymphocyes isolated from spleens of Foxp3-GFP mice, stimulated by CD28 and CD3 antibodies and incubated for 72 h in the presence of supernatants from A375 melanoma cells transfected with scr, miR-30d, siGALNT7, siIL10 and miR-30d+siIL-10. Note the decrease in T-cell activation in the miR-30d and siGALNT7 treatment groups compared to scr. The silencing of IL-10 in the presence of miR-30d only partially restores the levels of T-cell activation. 18B. Total number of T cells at conclusion of the experiment was lower in the miR-30d and siGALNT7 treatment groups (representative experiment, n=3). 18C. FACS analysis of activated (CD25+ CD69+CD4+) T lymphocyes isolated from spleens of Foxp3-GFP mice, stimulated by CD28 and CD3 antibodies and incubated for 72 h in the presence of supernatants from 5B1 melanoma cells transfected with scr+pcDNA3-Empty (scr), miR-30d+pcDNA3-Empty (30d), scr+pCMV-GALNT7 (GALNT7) and miR-30d+pCMV-GALNT7 (30d+ GALNT7). The decrease in T-cell activation in miR-30d treatment group was rescued by the ectopic expression of GALNT7. 18D. Total number of T cells at conclusion of the experiment was lower in the miR-30d and was rescued when GALNT7 was co-expressed (representative experiment, n=2).
Figure 18D:
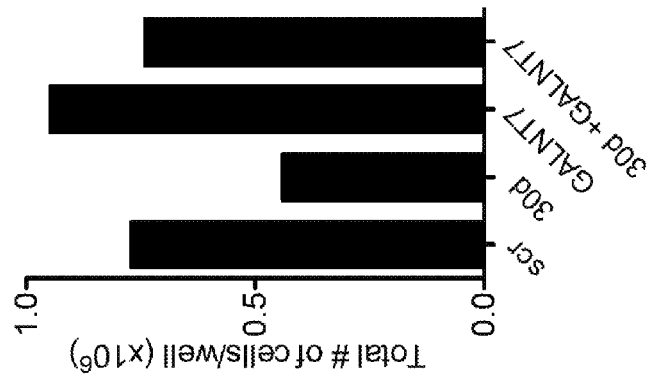
Figure 18C:
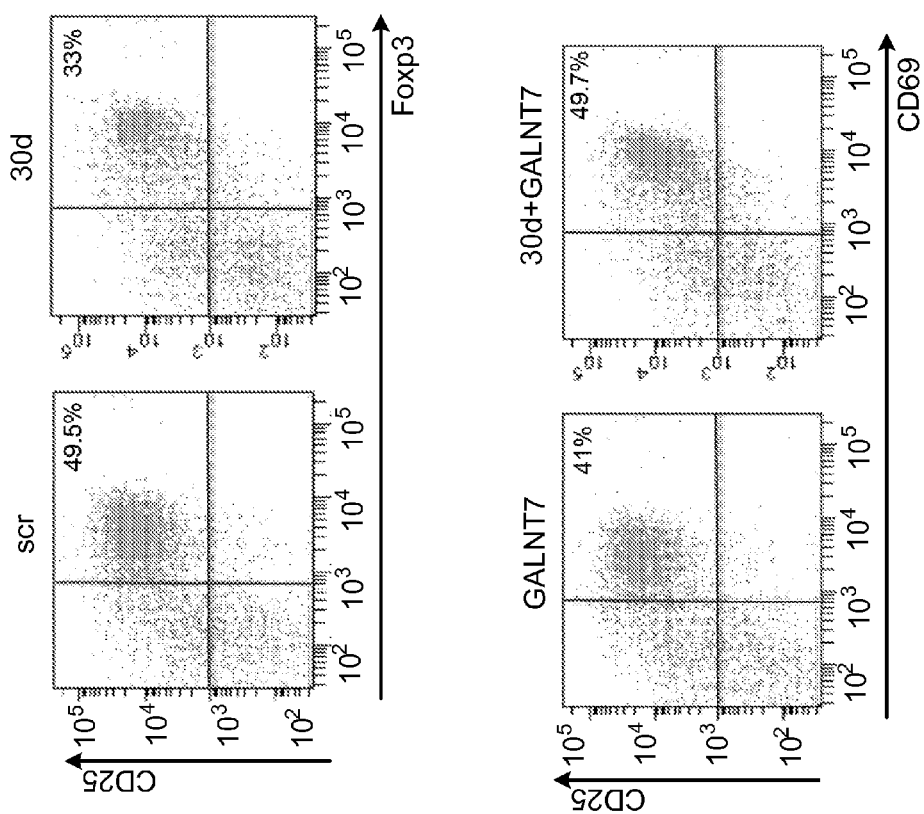

In order to explore the mechanism of immune modulation by miR-30d, we tested the ability of miR-30d upregulation or GALNT7 silencing to alter the secretion of immunomodulatory molecules by melanoma cells. For that, CD4+ splenocytes isolated from FoxP3-GFP mice (Bettelli et al., 2006) were activated ex vivo with CD28 and CD3 antibodies and then incubated in the presence of supernatants from scrambled, miR-30d, or siGALNT7-transfected A375 melanoma cells. We observed that supernatants from miR-30d or siGALNT7 display increased ability to suppress T cell activation (assessed by expression of surface markers CD25 and CD69) (FIG. 18A), and total T cell number (data not shown) than those from scrambled-transfected cells. Importantly, these effects of miR-30d were reversed by co-expression of GALNT7 cDNA in 5B1 melanoma cells (data not shown). In addition, supernatants from miR-30d and siGALNT7 promoted T cell differentiation into regulatory T cells (Tregs), as indicated by the number of CD25+GFP+ (Foxp3+) cells (FIG. 19C). Moreover, we found that concomitant silencing of IL-10 by siRNA only partially counteracted miR-30d immunosuppressive activities (FIGS. 18A, 18B and 20C). Therefore, our data suggest that IL-10 is one of multiple immunomodulatory molecules in miR-30d's regulated cellular secretome.

DISCUSSION

We have demonstrated that miR-30d/30b overexpression enhances the invasive capacity of melanoma cells in vitro and increases their metastatic potential in vivo, predominantly by suppressing GALNT7. Downregulation of miR-30d/b produced the opposite effects, while direct silencing of GALNT7 replicated most effects of miR-30d/b overexpression. Changes in glycosylation patterns have been associated with tumor progression for some time (Dennis et al., 1999), yet the specific molecular mechanisms underlying abnormal glycosylation and the downstream processes directly or indirectly contributing to metastasis remain poorly characterized. Strikingly, aberrant miRNA-mediated regulation of a GalNAc transferase promoted both cell motility and immunosuppressive mechanisms, which could synergize during metastasis.

Glycosylation in Tumor Progression

Our lectin arrays revealed that GALNT7 silencing or miR-30d upregulation have specific effects on O-glycans and, to a lesser extent, on N-glycosylated substrates. Alterations in O-glycans have many biological consequences in cancer, because potential ligands responsible for interactions between cancer cells and their microenvironment are changed. This influences the growth and survival of the cell and its interactions with lectins and cell-surface receptors on neighboring cells or immune cells, all of which are important for its ability to metastasize (Brockhausen, 2006). GalNAc transferases (GalNAc-Ts) initiate mucin-type O-linked glycosylation in the Golgi apparatus by catalyzing the transfer of GalNAc to serine and threonine residues on target proteins (Ten Hagen et al., 2003). GalNAc-Ts have different but overlapping substrate specificities and patterns of expression. Our glycomic analysis revealed that GALNT7 silencing has broad effects on the glycosylation of melanoma cells beyond its known transferase activity. These effects could be moderated through mislocalization of other enzymes in the pathway due to loss of the transferase, or there could be alterations in protein localization and stability that influence the general glycosylation phenotype. Regardless, the glycomic signature is clearly rescued by overexpression of GALNT7, indicating that the effects are specific to this enzyme. This modified glycocode might, at least partially, account for miR-30d/ siGALNT7 phenotype, even though the direct effectors (i.e. glycans, signaling pathways) of their pro-invasive and immunomodulatory actions could not be elucidated at this time. Pre-incubation with pertussis toxin did not affect miR-30d's pro-metastatic effects, suggesting that G1-dependent chemokine signaling is not a key player, at least under those experimental conditions.

We have shown that expression of GALNT7 and GALNT1 is controlled by miR-30b/30d levels, which increase during melanoma tumor progression in parallel with advancing stage and metastatic potential at the time of diagnosis. Intriguingly, in addition to GALNT1 and GALNT7, other GalNAc-T family members carry miR-30d recognition sites and we found that the expression of many of them inversely correlated with miR-30d levels in human samples, suggesting that this miRNA might coordinately regulate the entire GALNT family. Not much is known about the regulation of the GALNT family, though GALNT7 has also been shown to be modulated by another miRNA, miR-378, with a potential effect in osteoblast differentiation (Kahai et al., 2009).

It is interesting to note that a pro-metastatic role for miR-30d has also been recently shown in hepatocellular carcinoma (Yao et al., 2009), and that miR-30d levels in the sera of lung cancer patients correlate with poor prognosis (Hu et al., 2010). Together, these studies indicate that this miRNA cluster (and possibly GALNT suppression) might exert a common pro-metastatic effect in various cancers. The pleiotropic effects (immunosuppressive and pro-invasive) of miR-30d described here for melanoma mostly mediated by GalNAc-T suppression might thus be relevant in other tumor types. In fact, metastatic clones derived from colorectal cancer cells have altered expression of various GalNAc-Ts in comparison with their non-metastatic parental counterparts (Kato et al., 2010).

Curiously, miR-30e, which shares a seed region with miR-30b/d but is located in a separate genomic location, has shown an anti-metastatic role in breast cancer (Yu et al., 2010). A plausible explanation for this apparent paradox is that whereas O-glycosylation of specific substrates, particularly of mucins, promotes breast or colon cancer progression (Brockhausen, 2006), the expression of mucins and their contribution to metastasis in melanoma is known to be limited (Bhavanandan, 1991). In addition, the cell-type specific repertoire of GalNAc-Ts, which vary with cellular differentiation and malignant transformation (Mandel et al., 1999), could account for the opposing outcomes of miR-30e and miR-30b/30d induction in different tumors. These observations underscore the context-dependence of miRNA functions in cancer.

In addition to the GALNT family, we validated other miR-30d targets such as SEMA3A, which exerts anti-angiogenic functions (Maione et al., 2009; Serini et al., 2003), and CESLR3 and TWFJ, which are involved in cell-to-cell interactions and migration. Downregulation of these genes, however, failed to promote melanoma cell invasion through a fibronectin coat. They may nevertheless mediate other metastatic abilities not tested here, such as vascularization, adhesion or motility.

Immune Modulation in Melanoma

Melanoma is a paradigmatically immunogenic tumor, with abundant inflammatory infiltrates in both cutaneous and metastatic lesions, yet it manages to evade this upregulated host immune response (Lee et al., 2005; Real et al., 2001; Redondo et al., 2003). The mechanisms underlying melanomaassociated immunosuppression are poorly understood, but they could explain the discrepancy between the induction of systemic immunity by anti-melanoma vaccines and their modest effects in the clinic (Bhardwaj, 2007). We found that miR-30d overexpression correlates with reduced CD3+ T cells recruitment and accumulation of Tregs at the metastatic site in vivo. Consistently, we demonstrated that miR-30d upregulation alters melanoma cells' secretome such that it suppresses T cell activation and favors Treg induction ex vivo. These effects can be partially mediated by increased IL-10 secretion, which results from GALNT7 suppression. This miR-30b/30d-GALNT7-IL-10 axis could provide a mechanistic explanation for the immunosuppressive behavior of some metastatic melanomas. We observed some association between higher miR-30d expression and more FOXP3-positive lymphocytes (putative Tregs) in human metastatic samples. Surprisingly, high 30d levels significantly correlated with FOXP3 expression in the tumor cells themselves. The expression of FOXP3 by tumor cells was already reported in several cancer types (Hinz et al., 2007; Merlo et al., 2009), including melanoma (Ebert et al., 2008). It has been proposed that tumor cells expressing FOXP3 share immunosuppressive effects with Tregs (Martin et al., 2010) which might represent a new mechanism of immune evasion in melanoma. Both cell and non-cell autonomous mechanisms, potentially exerted by miR-30d, could cooperate to restrain the host antitumoral response. MiR-30d pro-metastatic effects, critically mediated by GALNT7 suppression, are prominent even in the absence of a functional host immune system, as indicated by our experiments conducted in NOG/SCID mice. However, our results in immunocompetent mice reveal notable immunosuppressive effects associated with miR-30d upregulation, which might synergize with its proinvasive properties during metastasis.

The control of immuno-stimulant or immuno-suppressive molecules by miRNAs in the context of tumor formation and progression is largely unexplored. MiR-21, a miRNA with established tumorigenic role (Esquela-Kerscher and Slack, 2006), has been shown to negatively regulate TLR4 via targeting the proinflammatory tumor suppressor PDCD4 (Sheedy et al., 2010), but the contribution of this mechanism to the tumorigenic activities of miR-21 remains unknown. Evidence of another miRNA directly targeting IL-10, miR-106a, has been recently reported (Sharma et al., 2009). It is interesting to note in this context that we found reduced miR-106a levels in miR-30d transduced cells (data not shown), which suggests a possible miRNA network converging on the modulation of IL-10 levels.

A recent report showed that Snail-mediated induction of epithelial to mesenchymal transition induces an immunosuppressive response in melanoma cells mainly by inducing the cytokine TSP1 (Kudo-Saito et al., 2009). These data and our current results reveal that cell migration and immune evasion are intimately connected during metastasis, and our findings suggest that GalNAc transferases can serve as a link between the two.

In sum, this study is the first to show that a single miRNA can exert both pro-invasive and immunomodulatory effects, and that both actions could be critically mediated by one target, GALNT7. Our data could have important prognostic implications: higher miR-30d expression correlates with advanced melanoma, aggressive biological behavior, and is a predictor of time to death with melanoma, independent of thickness. Moreover, miR-30d targeting represents a plausible therapeutic approach: targeting miR-30d in tumor cells with chemically modified oligonucleotides or artificial decoys [reviewed in (Tong and Nemunaitis, 2008) and (Valastyan and Weinberg, 2009)] could de-repress the endogenous GALNT7 levels, simultaneously counteracting both its pro-invasive and immunosuppressive effects.

REFERENCES

Bettelli, E., Carrier, Y., Gao, W., Korn, T., Strom, T. B., Oukka, M., Weiner, H. L., and Kuchroo, V. K. (2006). Reciprocal developmental pathways for the generation of pathogenic effector TH17 and regulatory T cells. Nature 441, 235-238.

Bhardwaj, N. (2007). Harnessing the immune system to treat cancer. J Clin Invest 117, 1130-1136.

Bhavanandan, V. P. (1991). Cancer-associated mucins and mucin-type glycoproteins. Glycobiology 1, 493-503.

Bogunovic, D., O'Neill, D. W., Belitskaya-Levy, I., Vacic, V., Yu, Y. L., Adams, S., Darvishian, F., Berman, R., Shapiro, R., Pavlick, A. C., et al. (2009) Immune profile and mitotic index of metastatic melanoma lesions enhance clinical staging in predicting patient survival. Proc Natl Acad Sci USA 106, 20429-20434.

Brockhausen, I. (2006). Mucin-type O-glycans in human colon and breast cancer: glycodynamics and functions. EMBO Rep 7, 599-604.

Calin, G. A., and Croce, C. M. (2006). MicroRNA signatures in human cancers. Nat Rev Cancer 6, 857-866.

Croce, C. M., and Calin, G. A. (2005). miRNAs, cancer, and stem cell division. Cell 122, 6-7. Cruz-Munoz, W., Man, S., Xu, P., and Kerbel, R. S. (2008). Development of a preclinical model of spontaneous human melanoma central nervous system metastasis. Cancer Res 68, 4500-4505.

Dennis, J. W., Granovsky, M., and Warren, C. E. (1999). Glycoprotein glycosylation and cancer progression. Biochim Biophys Acta 1473, 21-34.

Ebert, L. M., Tan, B. S., Browning, J., Svobodova, S., Russell, S. E., Kirkpatrick, N., Gedye, C., Moss, D., Ng, S. P., MacGregor, D., et al. (2008). The regulatory T cell-associated transcription factor FoxP3 is expressed by tumor cells. Cancer Res 68, 3001-3009.

Ehlers, J. P., Worley, L., Onken, M. D., and Harbour, J. W. (2005). DDEF1 is located in an amplified region of chromosome 8q and is overexpressed in uveal melanoma. Clin Cancer Res 11, 3609-3613.

Esquela-Kerscher, A., and Slack, F. J. (2006). Oncomirs—microRNAs with a role in cancer. Nat Rev Cancer 6, 259-269.

Gupta, G. P., and Massague, J. (2006). Cancer metastasis: building a framework. Cell 127, 679-695.

Gupta, P. B., Mani, S., Yang, J., Hartwell, K., and Weinberg, R. A. (2005). The evolving portrait of cancer metastasis. Cold Spring Harb Symp Quant Biol 70, 291-297.

Hinz, S., Pagerols-Raluy, L., Oberg, H. H., Ammerpohl, O., Grussel, S., Sipos, B., Grutzmann, R., Pilarsky, C., Ungefroren, H., Saeger, H. D., et al. (2007). Foxp3 expression in pancreatic carcinoma cells as a novel mechanism of immune evasion in cancer. Cancer Res 67, 8344-8350.

Hu, Z., Chen, X., Zhao, Y., Tian, T., Jin, G., Shu, Y., Chen, Y., Xu, L., Zen, K., Zhang, C., and Shen, H. (2010). Serum microRNA signatures identified in a genome-wide serum microRNA expression profiling predict survival of non-small-cell lung cancer. J Clin Oncol 28, 1721-1726.

Huang da, W., Sherman, B. T., and Lempicki, R. A. (2009). Systematic and integrative analysis of large gene lists using DAVID bioinformatics resources. Nat Protoc 4, 44-57. Irizarry, R. A., Bolstad, B. M., Collin, F., Cope, L. M., Hobbs, B., and Speed, T. P. (2003). Summaries of Affymetrix GeneChip probe level data. Nucleic Acids Res 31, e15.

Kahai, S., Lee, S. C., Lee, D. Y., Yang, J., Li, M., Wang, C. H., Jiang, Z., Zhang, Y., Peng, C., and Yang, B. B. (2009). MicroRNA miR-378 regulates nephronectin expression modulating osteoblast differentiation by targeting GalNT-7. PLoS ONE 4, e7535.

Kato, K., Takeuchi, H., Kanoh, A., Miyahara, N., Nemoto-Sasaki, Y., Morimoto-Tomita, M., Matsubara, A., Ohashi, Y., Waki, M., Usami, K., et al. (2010). Loss of UDPGalNAc: polypeptide N-acetylgalactosaminyltransferase 3 and reduced O-glycosylation in colon carcinoma cells selected for hepatic metastasis. Glycoconj J 27, 267-276.

Kudo-Saito, C., Shirako, H., Takeuchi, T., and Kawakami, Y. (2009). Cancer metastasis is accelerated through immunosuppression during Snail-induced EMT of cancer cells. Cancer Cell 15, 195-206.

Lee, J. H., Torisu-Itakara, H., Cochran, A. J., Kadison, A., Huynh, Y., Morton, D. L., and Essner, R. (2005). Quantitative analysis of melanoma-induced cytokine-mediated immunosuppression in melanoma sentinel nodes. Clin Cancer Res 11, 107-112.

Lewis, B. P., Burge, C. B., and Bartel, D. P. (2005). Conserved seed pairing, often flanked by adenosines, indicates that thousands of human genes are microRNA targets. *Cell* 120, 15-20.

Lu, Y., Ryan, S. L., Elliott, D. J., Bignell, G. R., Futreal, P. A., Ellison, D. W., Bailey, S., and Clifford, S. C. (2009). Amplification and overexpression of Hsa-miR-30b, Hsa-miR-30d and KHDRBS3 at 8q24.22-q24.23 in medulloblastoma. PLoS ONE 4, e6159.

Ma, L., Teruya-Feldstein, J., and Weinberg, R. A. (2007). Tumour invasion and metastasis initiated by microRNA-10b in breast cancer. Nature 449, 682-688.

Ma, L., Young, J., Prabhala, H., Pan, E., Mestdagh, P., Muth, D., Teruya-Feldstein, J., Reinhardt, F., Onder, T. T., Valastyan, S., et al. miR-9, a MYC/MYCN-activated microRNA, regulates Ecadherin and cancer metastasis. Nat Cell Biol 12, 247-256.

Maione, F., Molla, F., Meda, C., Latini, R., Zentilin, L., Giacca, M., Seano, G., Serini, G., Bussolino, F., and Giraudo, E. (2009). Semaphorin 3A is an endogenous angiogenesis inhibitor that blocks tumor growth and normalizes tumor vasculature in transgenic mouse models. J Clin Invest 119, 3356-3372.

Mandel, U., Hassan, H., Therkildsen, M. H., Rygaard, J., Jakobsen, M. H., Juhl, B. R., Dabelsteen, E., and Clausen, H. (1999). Expression of polypeptide GalNAc-transferases in stratified epithelia and squamous cell carcinomas: immunohistological evaluation using monoclonal antibodies to three members of the GalNAc-transferase family. Glycobiology 9, 43-52.

Martin, F., Ladoire, S., Mignot, G., Apetoh, L., and Ghiringhelli, F. (2010). Human FOXP3 and cancer. Oncogene 29, 4121-4129.

Merlo, A., Casalini, P., Carcangiu, M. L., Malventano, C., Triulzi, T., Menard, S., Tagliabue, E., and Balsari, A. (2009). FOXP3 expression and overall survival in breast cancer. J Clin Oncol 27, 1746-1752.

Palmgren, S., Vartiainen, M., and Lappalainen, P. (2002). Twinfilin, a molecular mailman for actin monomers. J Cell Sci 115, 881-886.

Real, L. M., Jimenez, P., Kirkin, A., Serrano, A., Garcia, A., Canton, J., Zeuthen, J., Gamido, F., and Ruiz-Cabello, F. (2001). Multiple mechanisms of immune evasion can coexist in melanoma tumor cell lines derived from the same patient. Cancer Immunol Immunother 49, 621-628.

Redondo, P., Sanchez-Carpintero, I., Bauza, A., Idoate, M., Solano, T., and Mihm, M. C., Jr. (2003). Immunologic escape and angiogenesis in human malignant melanoma. J Am Acad Dermatol 49, 255-263.

Rozen, S., and Skaletsky, H. (2000). Primer3 on the WWW for general users and for biologist programmers. Methods Mol Biol 132, 365-386.

Scheel, C., Onder, T., Karnoub, A., and Weinberg, R. A. (2007). Adaptation versus selection: the origins of metastatic behavior. Cancer Res 67, 11476-11479; discussion 11479-11480.

Segura, M. F., Belitskaya-Levy, I., Rose, A. E., Zakrzewski, J., Gaziel, A., Hanniford, D., Darvishian, F., Berman, R. S., Shapiro, R. L., Pavlick, A. C., et al. (2010). Melanoma MicroRNA Signature Predicts Post-Recurrence Survival. Clin Cancer Res 16, 1577-1586.

Segura, M. F., Hanniford, D., Menendez, S., Reavie, L., Zou, X., Alvarez-Diaz, S., Zakrzewski, J., Blochin, E., Rose, A., Bogunovic, D., et al. (2009). Aberrant miR-182 expression promotes melanoma metastasis by repressing FOXO3 and microphthalmia-associated transcription factor. Proc Natl Acad Sci USA 106, 1814-1819.

Serini, G., Valdembri, D., Zanivan, S., Morterra, G., Burkhardt, C., Caccavari, F., Zammataro, L., Primo, L., Tamagnone, L., Logan, M., et al. (2003). Class 3 semaphorins control vascular morphogenesis by inhibiting integrin function. Nature 424, 391-397.

Sharma, A., Kumar, M., Aich, J., Hariharan, M., Brahmachari, S. K., Agrawal, A., and Ghosh, B. (2009). Posttranscriptional regulation of interleukin-10 expression by hsa-miR-106a. Proc Natl Acad Sci USA 106, 5761-5766.

Sheedy, F. J., Palsson-McDermott, E., Hennessy, E. J., Martin, C., O'Leary, J. J., Ruan, Q., Johnson, D. S., Chen, Y., and O'Neill, L. A. (2010). Negative regulation of TLR4 via targeting of the proinflammatory tumor suppressor PDCD4 by the microRNA miR-21. Nat Immunol 11, 141-147.

Subramanian, S., Lui, W. O., Lee, C. H., Espinosa, I., Nielsen, T. O., Heinrich, M. C., Corless, C. L., Fire, A. Z., and van de Rijn, M. (2008). MicroRNA expression signature of human sarcomas. Oncogene 27, 2015-2026.

Talmadge, J. E. (2007). Clonal selection of metastasis within the life history of a tumor. Cancer Res 67, 11471-11475.

Tavazoie, S. F., Alarcon, C., Oskarsson, T., Padua, D., Wang, Q., Bos, P. D., Gerald, W. L., and Massague, J. (2008). Endogenous human microRNAs that suppress breast cancer metastasis. Nature 451, 147-152.

Ten Hagen, K. G., Fritz, T. A., and Tabak, L. A. (2003). All in the family: the UDPGalNAc: polypeptide N-acetylgalactosaminyltransferases. Glycobiology 13, 1R-16R.

Tong, A. W., and Nemunaitis, J. (2008). Modulation of miRNA activity in human cancer: a new paradigm for cancer gene therapy? Cancer Gene Ther 15, 341-355.

Valastyan, S., and Weinberg, R. A. (2009). Assaying microRNA loss-of-function phenotypes in mammalian cells: emerging tools and their potential therapeutic utility. RNA Biol 6, 541-545.

Van Den Berg, C., Guan, X. Y., Von Hoff, D., Jenkins, R., Bittner, Griffin, C., Kallioniemi, O., Visakorpi, McGill, Herath, J., and et al. (1995). DNA sequence amplification in human prostate cancer identified by chromosome microdissection: potential prognostic implications. Clin Cancer Res 1, 11-18.

Visapaa, H., Seligson, D., Eeva, M., Gaber, F., Rao, J., Belldegrun, A., and Palotie, A. (2003).

8q24 amplification in transitional cell carcinoma of bladder. Appl Immunohistochem Mol Morphol 11, 33-36.

Wu, Q., and Maniatis, T. (1999). A striking organization of a large family of human neural cadherin-like cell adhesion genes. Cell 97, 779-790.

Yao, J., Liang, L., Huang, S., Ding, J., Tan, N., Zhao, Y., Yan, M., Ge, C., Zhang, Z., Chen, T., et al. (2009). MicroRNA-30d promotes tumor invasion and metastasis by targeting Galphai2 in hepatocellular carcinoma. Hepatology 51, 846-856.

Yu, F., Deng, H., Yao, H., Liu, Q., Su, F., and Song, E. (2010). Mir-30 reduction maintains selfrenewal and inhibits apoptosis in breast tumor-initiating cells. Oncogene 29, 4194-4204.

Yu, H., Pardoll, D., and Jove, R. (2009). STATs in cancer inflammation and immunity: a leading role for STAT3. Nat Rev Cancer 9, 798-809.

The present invention is not to be limited in scope by the specific embodiments described herein. Indeed, various modifications of the invention in addition to those described herein will become apparent to those skilled in the art form the foregoing description and the accompanying figures. Such modifications are intended to fall within the scope of the appended claims.

It is to be understood that all base sizes or amino acid sizes, all synthetic concentrations and all molecular weight or molecular mass values, are approximate, and are provided for description.

All patents, applications, publications, test methods, literature, and other materials cited herein are hereby incorporated by reference in their entirety.

The invention claimed is:

1. A method for treating melanoma comprising administering to a subject in need thereof an amount effective to treat melanoma of a composition comprising an agent which inhibits the expression of a nucleic acid sequence selected from the group consisting of: SEQ ID NOS: 9, 11 and 9+11 and a pharmaceutically acceptable carrier, wherein administration of the composition inhibits the growth and viability of melanoma cells in said subject.

2. The method of claim 1, wherein the nucleic acid is a modified oligonucleotide.

3. The method of claim 1, wherein the melanoma is metastatic melanoma.

4. The method of claim 3, wherein the metastatic melanoma is melanoma brain metastases.

5. The method of claim 1, wherein the composition is administered by a method selected from the group consisting of intratumoral administration, chemoembolization, subcutaneous administration and intravenous administration.

6. The method of claim 5, wherein said intratumoral administration is delivered through the blood brain barrier by a method selected from the group consisting of:
   (a) disruption of the blood brain barrier by osmotic means,
   (b) use of vasoactive substances, selected from the group consisting of bradykinin,
   (c) exposure to high intensity focused ultrasound,
   (d) use of endogenous transport systems, selected from the group consisting of carrier-mediated glucose transporters and carrier-mediated amino acid carriers;
   (e) use of receptor-mediated transcytosis, selected from the group consisting of receptor-mediated transcytosis of insulin and receptor-mediated transcytosis of transferrin;
   (f) blocking of active efflux transporters selected from the group consisting of p-glycoprotein;
   (g) intracerebral implantation,
   (h) convection-enhanced distribution, and
   (i) use of an infusion pump.

7. The method of claim 1, further comprising administering at least one additional therapy.

8. The method of claim 7, wherein the at least one additional therapy is a chemotherapeutic agent.

9. The method of claim 8, wherein said chemotherapeutic agent is selected from the group consisting of dacarbazine (DTIC), hydroxylurea, temozolomide, cisplatin, carboplatin, camptothecins, doxorubicin, cyclophosphamide, etoposide, vinblastine, Actinomycin D and cloposide.

10. The method of claim 1, wherein the administering results in one or more of:
   (a) inhibition of melanoma metastases,
   (b) reduction in melanoma metastases size,
   (c) reduction in melanoma metastases number,
   (d) reduction of number of melanoma cells,
   (e) reduction of melanoma cell viability, and
   (f) inhibition of melanoma cell growth.

* * * * *